United States Patent
Dunn et al.

(10) Patent No.: US 6,167,766 B1
(45) Date of Patent: Jan. 2, 2001

(54) PROGRAMMABLE ATMOSPHERIC SAMPLING SYSTEMS AND METHODS

(75) Inventors: David L. Dunn, Aiken, SC (US); Russell K. Huffmann, Martinez, GA (US); Bryan Bushart, Martinez, GA (US); Donald J. Pak, Martinez, GA (US); David M. Immel, Augusta, GA (US)

(73) Assignee: Westinghouse Savannah River Company, Aiken, SC (US)

( * ) Notice: Under 35 U.S.C. 154(b), the term of this patent shall be extended for 0 days.

(21) Appl. No.: 08/953,114

(22) Filed: Oct. 17, 1997

Related U.S. Application Data

(60) Provisional application No. 60/028,971, filed on Oct. 18, 1996.

(51) Int. Cl.[7] ................................................. G01N 1/00
(52) U.S. Cl. ............................................... 73/863.01
(58) Field of Search ........................... 73/863.31, 863.01, 73/864.34

(56) References Cited

U.S. PATENT DOCUMENTS

| | | | | |
|---|---|---|---|---|
| 4,245,499 | * | 1/1981 | Nguyen et al. | 73/863.01 |
| 4,521,857 | | 6/1985 | Reynolds, III | 379/88.17 |
| 4,800,763 | * | 1/1989 | Hakkers et al. | 73/863.31 |
| 4,864,877 | * | 9/1989 | Ortiz et al. | 73/863.31 |
| 4,896,548 | | 1/1990 | Lalin et al. | 73/863.03 |
| 4,910,692 | | 3/1990 | Outram et al. | 73/579 |
| 4,937,732 | | 6/1990 | Brundisini | 700/16 |
| 4,942,770 | * | 7/1990 | Seifert et al. | 73/864.34 |
| 5,016,196 | | 5/1991 | Nelson et al. | 73/170.17 |
| 5,262,936 | | 11/1993 | Faris et al. | 364/140 |
| 5,275,042 | | 1/1994 | Carson et al. | 73/216 |
| 5,297,421 | * | 3/1994 | Hosonuma et al. | 73/863.31 |
| 5,299,141 | | 3/1994 | Hungerford et al. | 73/863.01 |
| 5,303,598 | * | 4/1994 | Binder et al. | 73/863.01 |
| 5,381,331 | | 1/1995 | Mock et al. | 364/145 |
| 5,404,763 | * | 4/1995 | Guggenheim | 73/863.31 |
| 5,410,918 | * | 5/1995 | Zimmerman | 73/863.31 |
| 5,428,358 | | 6/1995 | Gardner | 73/170.16 |
| 5,481,904 | | 1/1996 | Fleck, Sr. et al. | 73/61.51 |
| 5,517,193 | | 5/1996 | Allison et al. | 324/26 |
| 5,551,311 | * | 9/1996 | Ogden et al. | 73/863.31 |
| 5,553,508 | * | 9/1996 | Dabberdt et al. | 73/863.31 |

FOREIGN PATENT DOCUMENTS 0 622 623 A2  11/1994  (EP) .
0 726 454 A2  8/1996  (EP) .

* cited by examiner

*Primary Examiner*—Robert Raevis
(74) *Attorney, Agent, or Firm*—Dean W. Russell; Kyle M. Globerman; Kilpatrick Stockton LLP

(57) ABSTRACT

A sampling system controller includes a control unit for interfacing with a collection chamber module having a plurality of sampling chambers. The control unit controls the times at which the sampling chambers acquire samples of a fluid flow and control flow rates into the sampling chambers. The timing of the sampling chambers and the flow rates may be programmed by a user and downloaded into the control unit through an interface. The control unit measures the flow rate of the fluid flow to be sampled and controls the flow rate through each sampling chambers in order to achieve a desired and known rate through the sampling chambers. The flow rates through the fluid flow and through the sampling chambers are recorded on a data module. The control unit may be equipped with a portable weather station for monitoring weather conditions and with a global positioning system for determining a geographic position of the sampling chambers. The weather and location information may be recorded on the data module. The flow rates through the sampling chambers are controlled by a flow assembly that is easily removed and replaced. The flow assembly has a set of jumpers which specify the flow range of the assembly and which is read by the control unit. A hand-held service module is used to program the sampling system. The service module has a keypad for receiving inputs from a user and has a switch for toggling between an RS232 output or an RS485 output.

31 Claims, 31 Drawing Sheets

PROGRAMMABLE ATMOSPHERIC SAMPLING SYSTEMS AND METHODS

This application claims the benefit of U.S. Provisional No. 60/028,971 filed Oct. 18, 1996.

FIELD OF THE INVENTION

This invention generally relates to systems and methods for sampling flow streams and, more particularly, to programmable sampling systems and methods for use in environmental or process monitoring.

BACKGROUND OF THE INVENTION

For various reasons, industries are often required to monitor air and water based pollutant emissions. For instance, industries must monitor their emissions to ensure the releases fall within acceptable limits specified by Federal, state, and local entities. In addition to compliance concerns, industries often desire to monitor emissions to ensure optimum process efficiency is achieved. Additionally Federal, state, and local entities often monitor air quality for general regions to ensure public health is not endangered. In all of the cases, it is often necessary or desirable to acquire samples, as opposed to real-time monitoring through active sensors, for subsequent analysis.

In general, conventional sampling systems are designed for process or emission specific monitoring applications. The conventional systems are tailored to the specific effluent to be monitored in terms of sample collection design, pumping system and flow regulation design, and peripheral sensor measurements. In cases where commercially manufactured equipment is not available for specific sampling applications, the user must design specific sampling equipment unique to the user's needs.

Conventional sampling systems have numerous disadvantages. Some of the disadvantages of conventional systems are that they have fixed flow systems with limited operating ranges, have limited or no sensor acquisition ability, have limited or no data retention, have limited or no sequential sampling capability, are designed to operate a single flow system as opposed to multiple flow systems concurrently, are unable or have limited ability to recover from power failures and loss of flow conditions, and are unable to sample diverse media, such as water and air media, stack or ambient conditions. With conventional sampling systems, the user must purchase a specific sampler for each sampling need or configure a sampler from available materials. The operating conditions of the conventional sampling system is typically fixed and cannot be altered. Additionally, when conventional sampling devices are used in hazardous areas, the entire sampling apparatus often can not easily be reused due to contamination of the equipment and the inability to remove contaminated components. With conventional sampling equipment, the entire equipment must periodically be removed from service in order to recalibrate the key components, such as a flow regulation mechanism.

A need therefore exists for systems or methods which can easily be adapted to the sampling of stack effluents, ambient air, or water. A need also exists for systems or methods of sampling that will allow for efficient exchange of the pumping and flow regulation media.

An example of a conventional sampling system is comprised of seven collection canister modules (CCMs) with one being used for each day of a week. Each CCM includes a solenoid to enable gas flow to the associated chamber and an asorbate material in the chamber for acquiring a material of interest. Each CCM has a pump for extracting process gas and for drawing the gas through the CCM where the asorbate material would acquire the material. A control unit having a timer would cycle through the CCMs so that each chamber in the CCM acquired a sample for a twenty four hour period.

The conventional sampling system has numerous disadvantages. The flow rate through the CCM is an assumed rate and the pump is only calibrated at periodic intervals. Since the flow rates into the chambers are not exact, the samples acquired in the CCMs do not accurately represent the actual flows through the facility. As a result, the actual amount of a pollutant or other material may actually be higher or lower than that estimated through the sampling. Without accurate information, the process occurring within the facility may not operate at an optimal level or the facility may be forced to take unnecessary costly measures to combat the emission of the detected material.

The conventional sampling system is generally unable to recover from an error or failure. For instance, if the pump fails, the control unit having the timer cycles through the remaining CCM chambers thereby rendering all of the collected samples invalid. Thus, data for an entire week may be totally worthless simply because of a single event. It is therefore a problem in the industry to obtain samples in a reliable manner.

The conventional sampling system is also rather rigid and inflexible. The flow rates through the chambers and the interval at which the control unit cycles through the chambers are fixed. If a change is desired in either the flow rate or the interval at which the chambers are cycled, the system must be rewired or the electronics in the system must be replaced. It is therefore rather difficult to adapt the conventional sampling system to a new flow rate or cycle interval. Further, the conventional sampling system is configured for a specific process and must be reconfigured if used outside of that process.

A need therefore exists for systems or methods of sampling effluents which can respond to emergency situations to ensure the integrity of samples. A need also exists for systems or methods of sampling which can be easily changed to have a different sampling rate or a different sampling interval. A need further exists for systems or methods for sampling which are not permanently attached to one facility but which can be transported to another facility.

SUMMARY OF THE INVENTION

A sampling system according to one aspect of the invention has a flow rate which may be programmed by the user. The sampling system includes an interface for receiving the programmed rate and a central processor for receiving the rate. A flow controller has its flow rate set by the central processor and control a pump so that it passes fluid into a sampling chamber at the programmed rate. The sampling system preferably monitors fluid flow through a process so that the flow through the sampling chamber can be adjusted to equal a desired rate. The sampling system may receive the programmed rate directly from a keypad or keyboard connected to the central processor or from an external computer. This external computer, moreover, may be interfaced directly with the sampling system or the sampling system may have a modem for communicating with a remote computer.

The sampling system may have a plurality of sensor inputs. One of these inputs, as discussed above, may be used to detect a rate at which a process fluid is flowing and another one of these inputs is preferably used to detect a temperature of the sampling system. Other inputs may be used to calibrate the sampling system, to receive weather data, or to receive position information.

The sampling system is preferably used with a collection canister module (CCM) having a plurality of sampling chambers. Each sampling chamber in the CCM has an associated solenoid valve for controlling fluid flow through the sampling chamber. The sampling system has a set of relays and at least one relay controller for activating the solenoid valves so that the sampling chambers obtain samples at desired times and in a desired order. The sampling system is not limited to just one CCM but instead may be coupled to two or more CCMs. The set of relays and relay controller are also used by the sampling system to control the sequencing of the CCMs.

The flow controller in the sampling system is preferably a removable flow assembly. The flow controller is mounted along with a pump on a mounting member which has guides for permitting the flow controller assembly to be easily inserted and removed from the sampling system. The flow controller assembly furthermore has a set of flow connectors for allowing quick connect and disconnect to the CCMs and a set of electrical connectors for coupling the flow controller and pump to the sampling system. To identify the range of a particular flow assembly, the flow assembly has a set of jumpers that can be read by the sampling system.

The sampling system can advantageously be programmed with a hand-held service module. The service module has a keypad for receiving user input and a display. The user can enter a desired set of programming information into the service module and connect the service module to an interface on the sampling system. The service module can therefore be used, for instance, to program sampling times, number of sampling chambers, number of modules, number of flow controllers, or flow ranges. The service module may be used for other purposes as well, such as calibrating the sampling system or reading data from a data module.

BRIEF DESCRIPTION OF THE DRAWINGS

The accompanying drawings, which are incorporated in and form a part of the specification, illustrate preferred embodiments of the present invention and, together with the description, serve to explain the principles of the invention. In the drawings.

DETAILED DESCRIPTION

Figure 1:
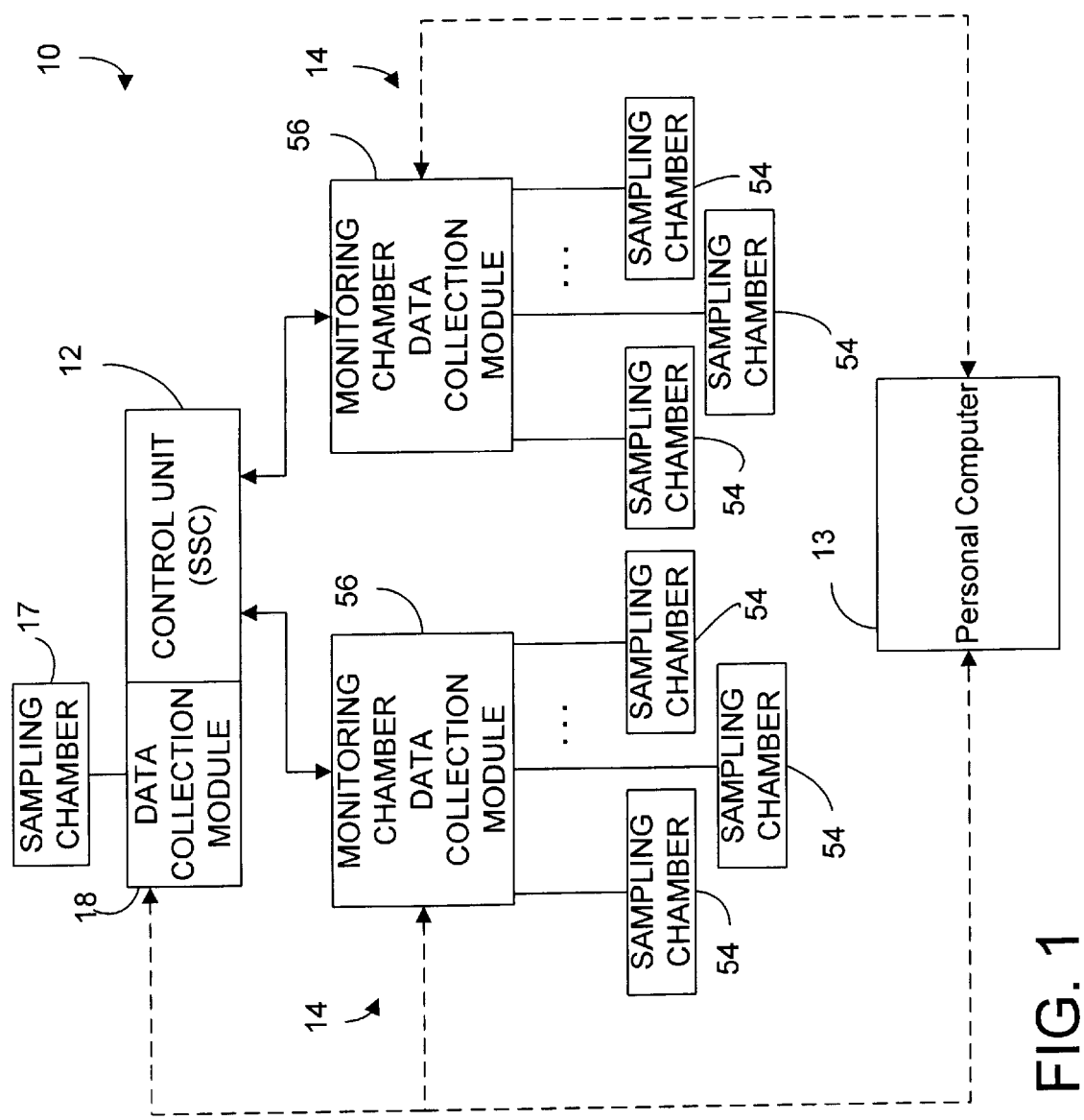
FIG. 1 is an overall block diagram of a sampling system according to a preferred embodiment of the invention.

Reference will now be made in detail to preferred embodiments of the invention, non-limiting examples of which are illustrated in the accompanying drawings.

I. SSC

A Programmable Sampling System Controller (SSC) 10 according to a first embodiment of the invention accurately controls air sampling in support of an environmental or process monitoring activity. The SSC 10 is comprised of a control unit 12 and two collection canister modules (CCM) 14, each CCM 14 containing seven sampling chambers 54. A side stream of air is diverted through a CCM 14 containing a specific absorption material. The CCM 14 is returned to the laboratory where the absorption material is processed to determine exposure to the analyte of interest. Each chamber of the CCM 14 is exposed to the side stream of air for twenty-four hours. Thus, the SSC 10 can run uninterrupted for two weeks during normal operation. The SSC 10 regulates the flow rate of extracted air steam through the CCM 14 and records this information to a temporary file in the control unit 12 as well as to a data collection module 56. At the end of twenty four hours, the SSC 10 is responsible for switching air flow to the next chamber 54 in the CCM 14 and, at the end of seven days, to the next CCM 14.

In order to determine the total analyte of interest present in the process system, it is necessary to know the flow rate through a given CCM 14 as well as the total flow through the process gas system. For this reason, the SSC 10, at a predetermined rate, periodically samples the CCM flow rate and the monitored air system total flow rate. The SSC 10 records this information to the CCM 14 as well as to a temporary file in the control unit 12. The following additional information is also recorded to both locations: SSC cabinet temperature, day, hour, and minute when the data was taken, CCM chamber number, and any abnormal conditions that were present when the measurement was taken.

A. Basic Operation

Prior to starting the SSC 10, the operator must first initialize the CCM data module 14 with the program "CCM-SET." "CCMSET" is designed to be run on any standard PC 13. A cable supplies power to the CCM data module 14 and interfaces the module 14 with an available serial port on the PC 13.

When "CCMSET" is run, the control unit 12 will prompt the user to connect the CCM 14 to the PC 13. The control unit 12 will read the ID of the CCM data module 14 and will prompt the user if they wish to change the CCM ID. If the user chooses to, they may enter any number in the range of 100 to 32,000 for the module ID. The control unit 12 will next display the default CCM data collection rate. Any value greater than or equal to 6.0 minutes per sample is valid. Values less than 6.0 minutes per sample should be used for testing only. Values less than 0.1 minutes per sample are preferably not used. The control unit 12 will display the default CCM flow rate. Any value greater than or equal to 0.5 standard liters per minute or less than or equal to 2.0 standard liters per minute is valid. The flow range of 0.5 to 2 liters per minute is just an example of a flow range for a particular flow controller and the SSC 10 may encompass other flow ranges. To accept any default values, the user should press "ENTER." The control unit 12 will display messages telling the user it is writing the clear flag, ID, flow rate, and sample rate to the CCM data module 14. The clear flag is used to tell the control unit 12 that the CCM 14 has been reset since the last time data has been written to the control unit 12.

After the "CCMSET" program has been run on one or two collection units, the operator is ready to connect the CCMs 14 to the control unit 12 and begin normal operation. Each CCM module 14 is connected to the control unit 12 by a cable terminated on both ends with, for instances, 19 pin Bendix style connectors. The connectors are preferably keyed and must be rotated to the correct orientation before they will seat in the mating plug. Each CCM 14 has an air line between the control unit 12 and the CCM 14. The electrical connections and air hose connections for a given CCM 14 are paired on the left and right side of the control unit 12. It is not necessary to have both CCMs 14 connected to the control unit 12 to begin operation nor is it necessary to have a single CCM 14 connected to the "CCM1" connectors on the control unit 12. When the SSC 10 begins operation, it will seek out the first available CCM 14, beginning with "CCM1," and begin operation. In the event the "CCM1" 14 unit cannot be used or is not connected, the control unit 12 will roll over to the "CCM2" unit 14.

Upon startup, the control unit 12 initializes its components, verifies the status of both CCM data modules 14, sets the active CCM flow path, starts the pump and enters an approximate 1 minute delay before beginning normal operation. This delay is desirable to ensure the SSC 10 has reached normal operating conditions before data sampling begins. During normal operation a front panel START switch will not be illuminated and STOP and RESET switches will be illuminated. The STOP and RESET switches are not illuminated during time intervals when data is being written to the CCM data modules 14. The extinguished lights inform the operator that the control unit 12 is unable to respond to the switches during this time interval. A red CCM light associated with the active CCM will be illuminated and the SSC display will indicate any error messages as well as the current collection chamber in use within the CCM 14. The STOP switch is used to terminate the operations of the control unit 12 and should not be used during normal operation. The RESET switch is used to verify the status of a connected CCM unit 14 that is not currently in use and to reset any alarm conditions.

At the end of seven days, the CCM 14 in use should be exhausted and the SSC 10 will switch to the next available CCM 14. The operator should verify this by examining the CCM lights. The CCM light on the front panel of the control unit 12 should indicate the SSC 10 has switched to the next available CCM 14. The operator should unplug the used CCM 14 and reconnect an unused CCM 14. The operator should press the RESET button to verify the new CCM 14 is operable. Although an operator need not press the RESET button when changing CCMs 14, the operator preferably presses the RESET button since the RESET function will verify the CCM 14 can be used when it is needed. If the new CCM 14 is good, the SSC 10 will display a message telling the operator the CCM module checkout is complete, otherwise an error message will be displayed.

If any alarm conditions occur during operation, a control room or other central location will receive the alarm. The alarm is preferably only cleared at the SSC 10 by removing the alarm condition and pressing the RESET button or by turning off power to the SSC 10. Once an alarm condition has occurred, removal of the alarm condition will not clear the alarm unless the RESET button if pressed on the control unit 12.

To retrieve data from a used CCM 14, the operator connects the CCM 14 to a cable supplying power to the CCM data module 56, as discussed below with reference to FIG. 3, and connects the data module 56 to a serial port on the host PC 13. The utility "CCMREAD" is used to extract data from the data module 56. The user will be asked to enter in a file name to store the information in, which preferably adheres to the DOS format. The data file is preferably a tab delimited text file and can be read by a Microsoft EXCEL program once the data is extracted or by other suitable programs. The data format is preferably as follows: Day, Hour, Minute, Stack Flow, Unit Flow, Cabinet Temperature, Canister Chamber Number, and Error Code, although other formats may be used. Each error code is one character with a maximum of four error codes possible: U—Controller Unit Flow Failure, S—Stack flow Reading Failure, T—High Controller Cabinet Temperature, C—No Collection Canister Units available. If an invalid file name is entered at the beginning of the program, the program 12 will abort operations. If after two successive tries, the operator is unable to read the data module's data, the operator should recover the data using the RECOVER utility on the SSC 10.

B. Hardware

1. Stack Flow and Temperature Measurement

Figure 2:
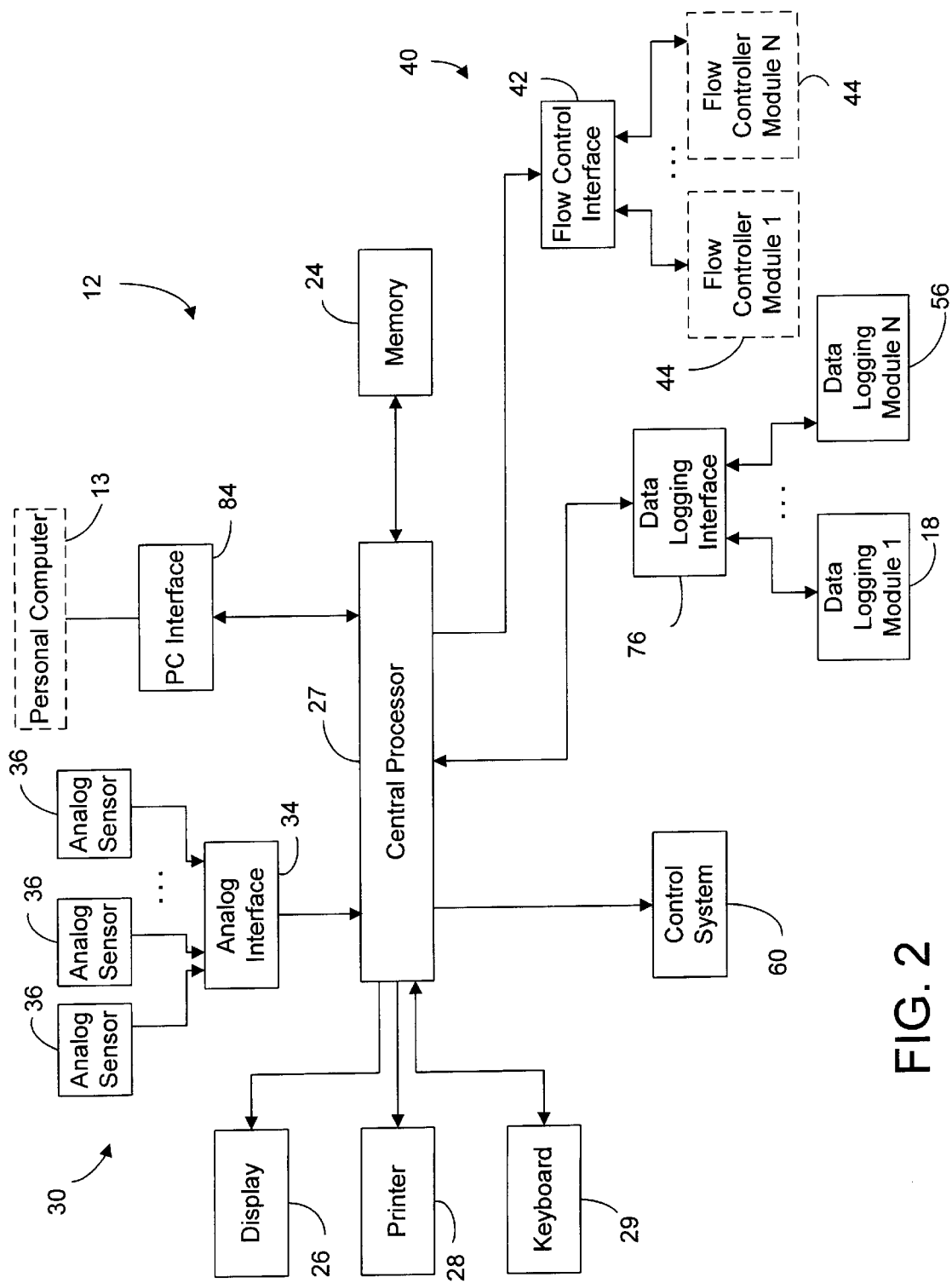
FIG. 2 is a more detailed block diagram of a control unit in the sampling system of FIG. 1.

An example of the control unit 12 is shown in more detail in FIG. 2. The control unit 12 includes a central processor 27, memory 24, a display 26, a printer 28, and a keypad or keyboard 29. The stack flow and temperature are measured by an analog input system 30 connected to the central processor 27. The analog input system 30 includes an analog interface 34 preferably comprised of a Sensoray card and a 7419 card, both of which are manufactured by WinSystems Inc. of Arlington, Tex. The analog interface 34 has onboard temperature reading devices to compensate for variations in cabinet conditions.

The analog input system 30 receives signals from analog sensors 36 which can produce a variety of signals, such as 0 to 5 volt signal or a 4 to 20 milliamp signal. The sensors 36 may comprise any type of sensor 36, such as thermistors, thermocouples, load cells, and other common analog measurement devices. The sensors 36 in the SSC 10, for instance, preferably include a thermocouple for measuring stack flow temperature and 4–20 loop for determining cabinet temperature.

The analog interface 34 includes resistors for converting current signals into voltage signals. For instance, a 4–20 milliamp signal fed from the process flow meter is converted to a voltage by a 249 Ohm 1% resistor installed at the input connection. Rather than a 250 Ohm component, a wire wound 249 1% resistor may be used which has an actual value greater than or equal to 249.5 Ohms but less than 250.5 Ohms. The use of this resistor produces an error on the 4–20 milliamp loop less than or equal to ±0.1 milliamp over the 4–20 milliamp range. Other inputs to the analog interface 34 may also include resistors or other circuitry for converting current signals to voltage signals or, alternatively, for converting voltage signals to current signals. The analog interface 34 preferably includes at least one input which does not contain a resistor. This input allows the analog input system 30 to be calibrated, even though the calibration of the analog system 30 should be sufficient for most applications of the SSC 10.

One of the inputs to the analog interface 34 is preferably connected to an internal thermocouple 36. The internal thermocouple 36 monitors internal cabinet temperature and displays a high temperature warning on display 26 if the temperature exceeds 45 degrees Centigrade. Other thermocouples 36 connected to the analog interface 36 may be used to monitor or track other temperatures, either internal or external. Furthermore, the internal thermocouple 36 may be replaced by an external temperature sensor.

2. SSC Gas Flow Regulation

The control unit 12 also includes a system 40 for regulating flow rates. The flow rate system 40 is preferably performed with calibrated flow controllers 44 manufactured by Sierra Monitor Corp. of Milpitas, Calif. Each flow controller 44 receives the desired flow control rate from the central processor 27 via an RS485 communication link. When requested, the flow controller 44 reports the actual flow control rate back to the central processor 27 over the same RS485 communication link. As shown in the figure, the control unit 12 includes a flow control interface 42 between the flow controller 44 and the central processor 27.

The flow controller 44 uses a PID algorithm for adjusting the flow control to the desired setpoint. The PID algorithm causes the output gain of the flow controller 44 to increase more rapidly as the deviation from the desired setpoint increases. As the error decreases, the gain decreases at a faster rate in order to avoid overshoot. The PID algorithm results in small deviation during normal operation while maintaining fast response to larger errors between the desired setpoint and actual flow control rate.

The central processor 27 comprises at least a x386 processor and preferably includes two serial channels. The central processor 27 has two serial communications links and either one or both links can be configured for RS485 communication. In this example, the first link is used for RS485 communications and the second serial link is an RS232 communication link that terminates at the rear of the control unit 12.

3. SSC Gas Flow Control

An explanation of the gas flow will now be described with reference to FIG. 3. The SSC 10 pulls a regulated amount of process gas from the process system, passes the process gas through a reactive agent chamber 54, and then returns the gas to the process. The components involved in performing these functions are the CCMs 14, CCM selection solenoid valves 48 which are internal to the control unit 12, the flow controllers 44, and SSC process gas pumps 46.

Each CCM 14, in the example shown, contains seven process gas chambers 54 each associated with a solenoid valve 52. The process gas passes into the CCM 14 and is routed to all seven solenoid valves 52. The solenoid valve 52 activated under control of the central processor 22 allows air flow through its associated chamber 54 while the inactive solenoid valves 52 disable the remaining chambers 54.

Figure 4:
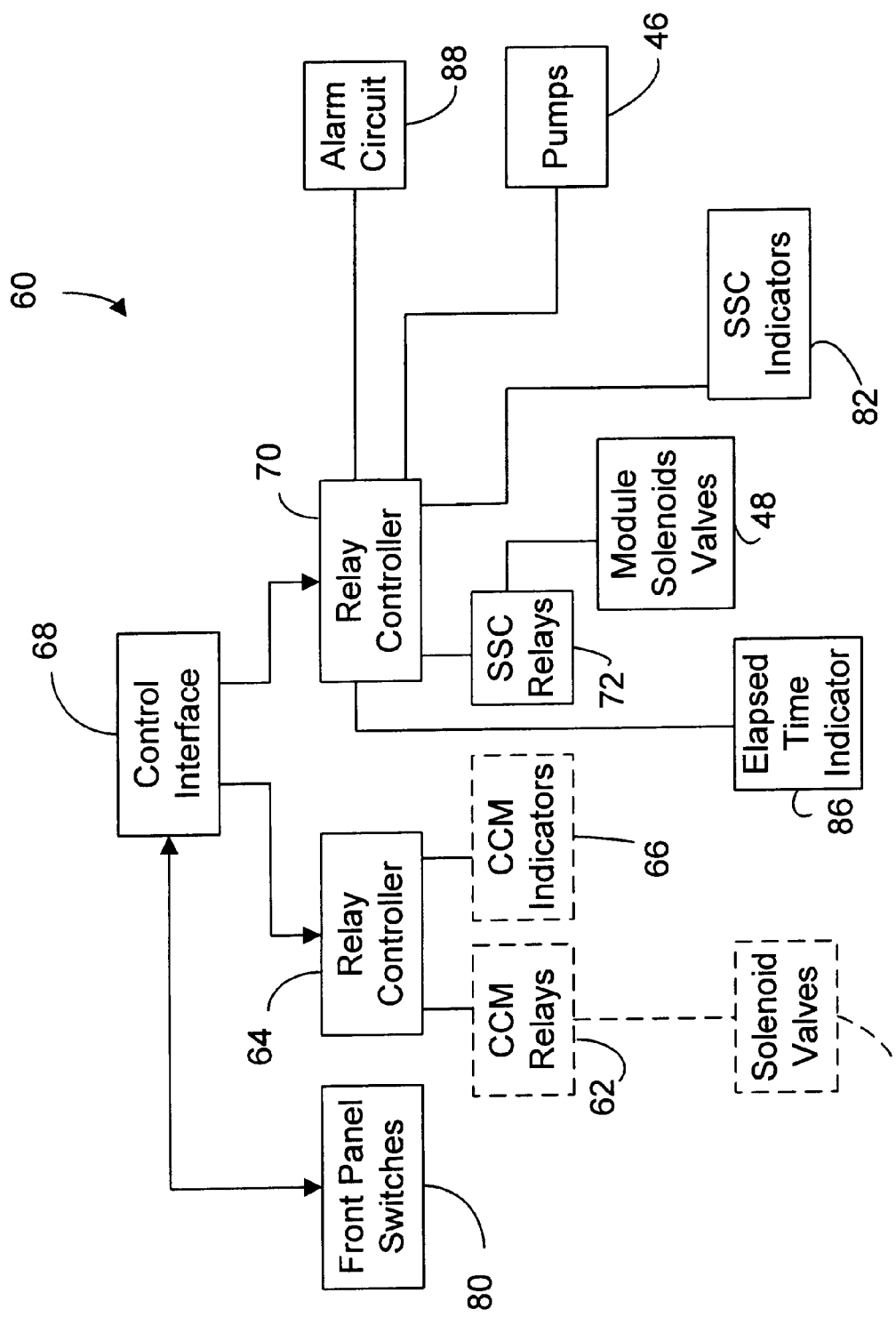
FIG. 4 is a block diagram of a control system in the sampling system of FIG. 1.
Figure 5A:
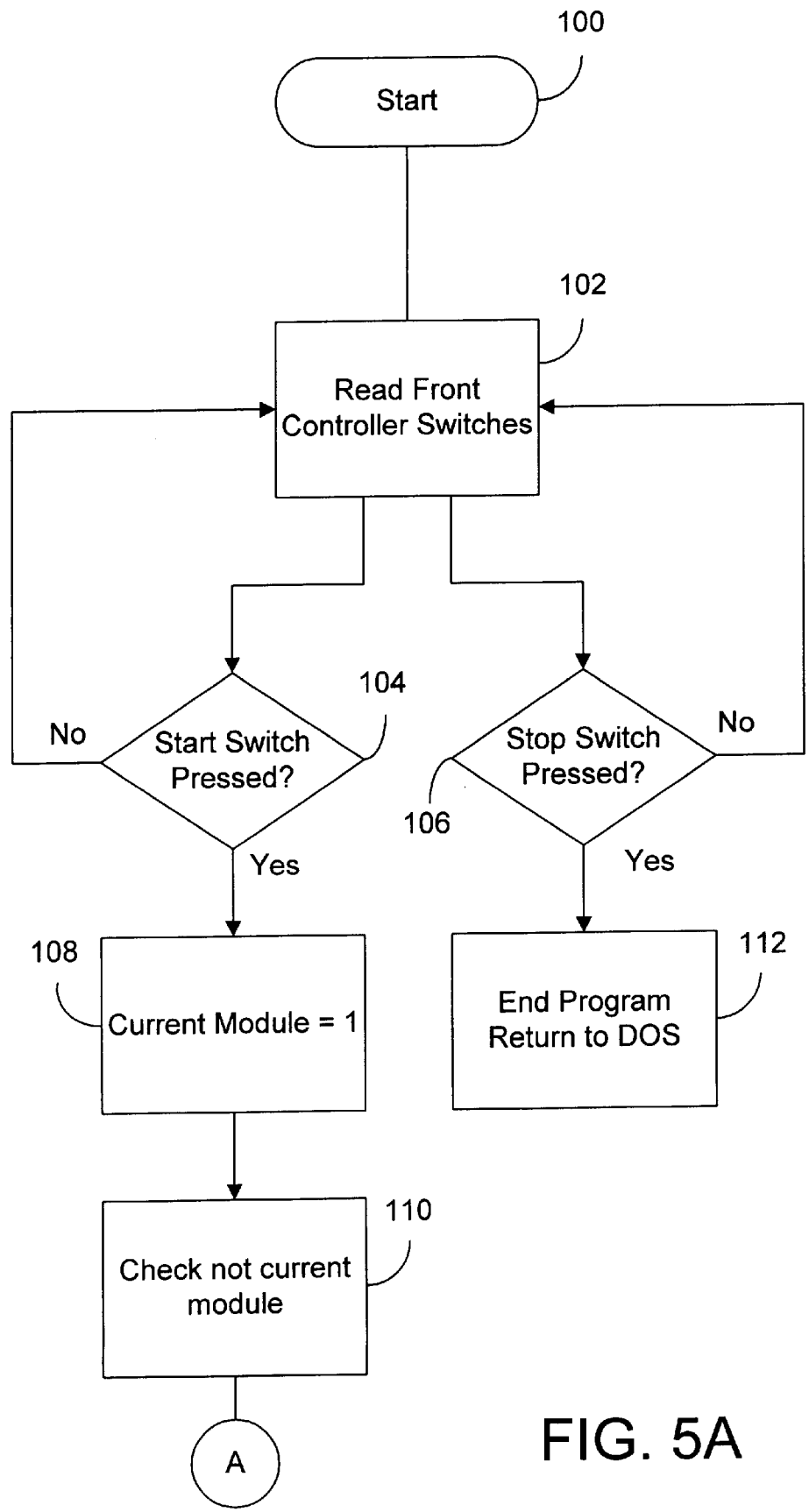
FIGS. 5A to 5E are flow charts depicting a main processing loop of the sampling system of FIG. 1.
Figure 5B:
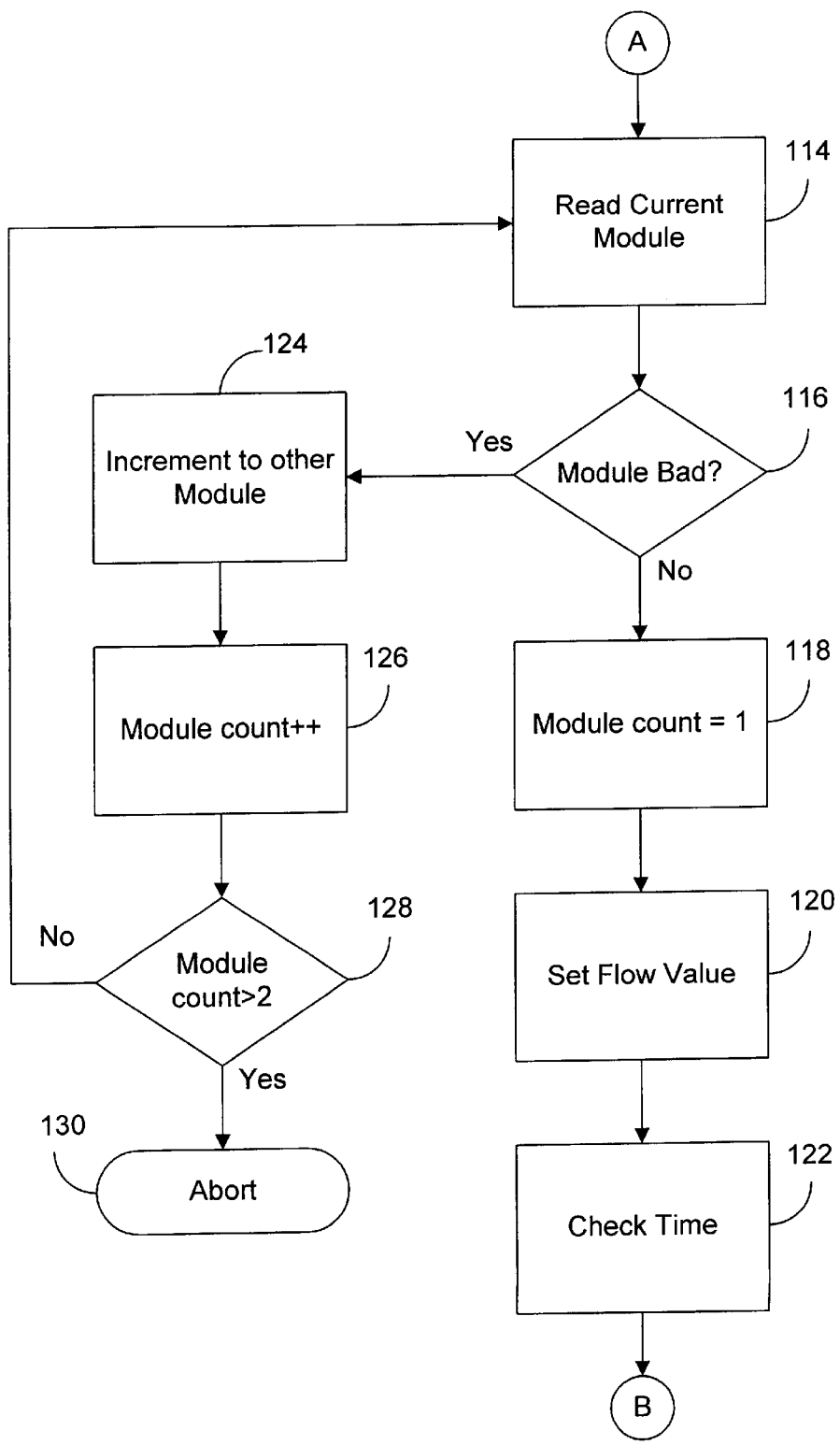
Figure 5C:
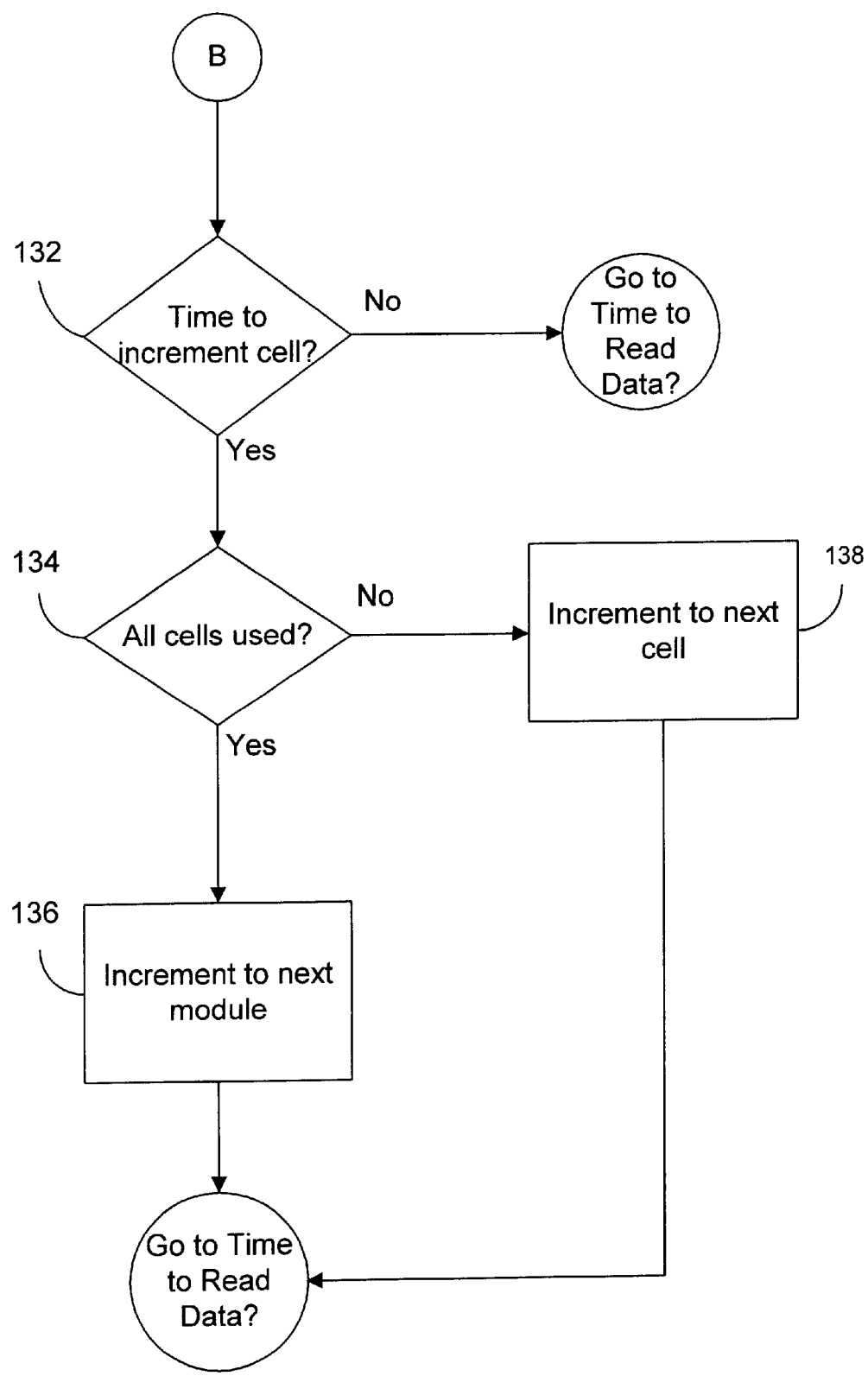
Figure 5D:
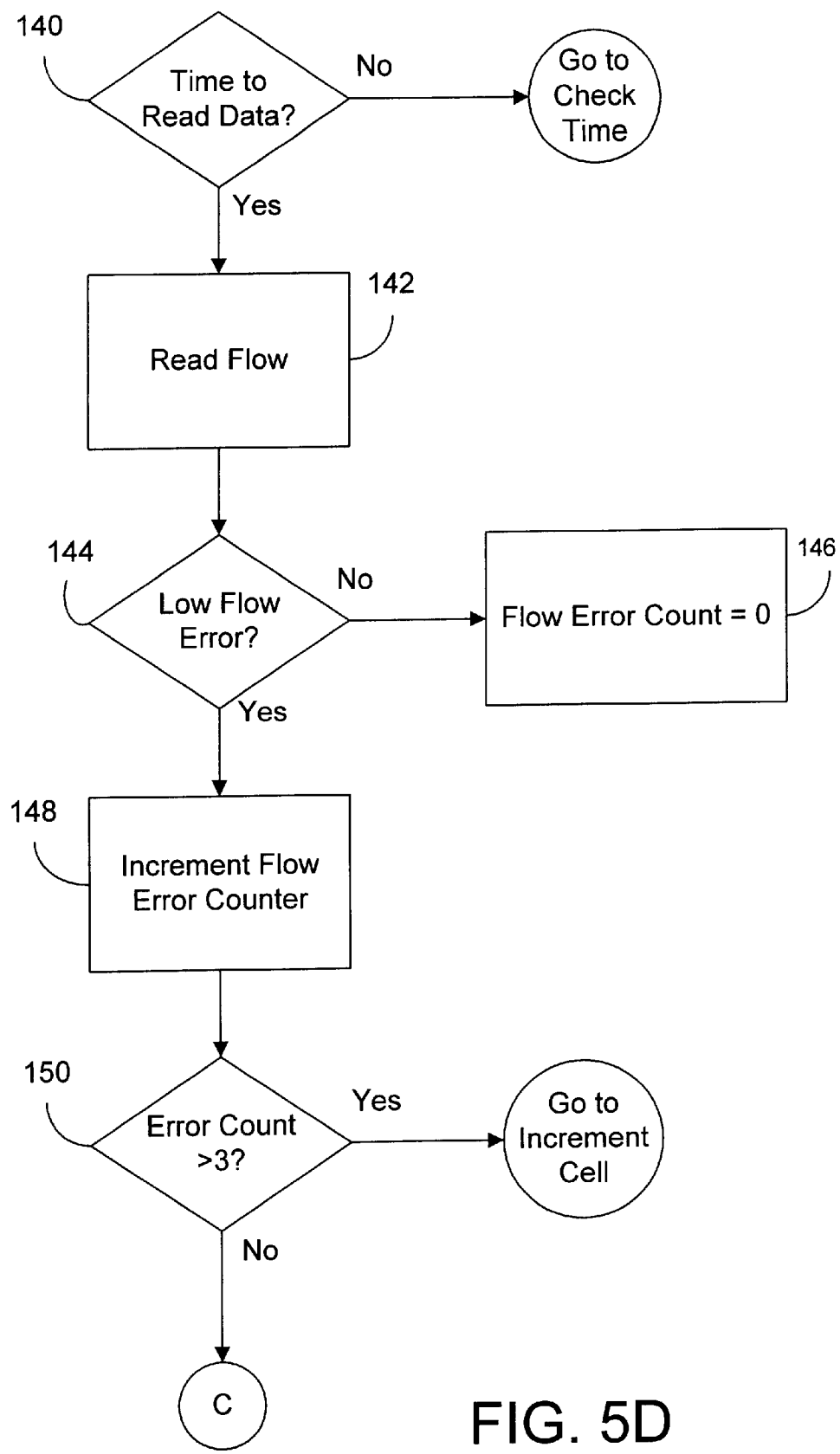
Figure 5E:
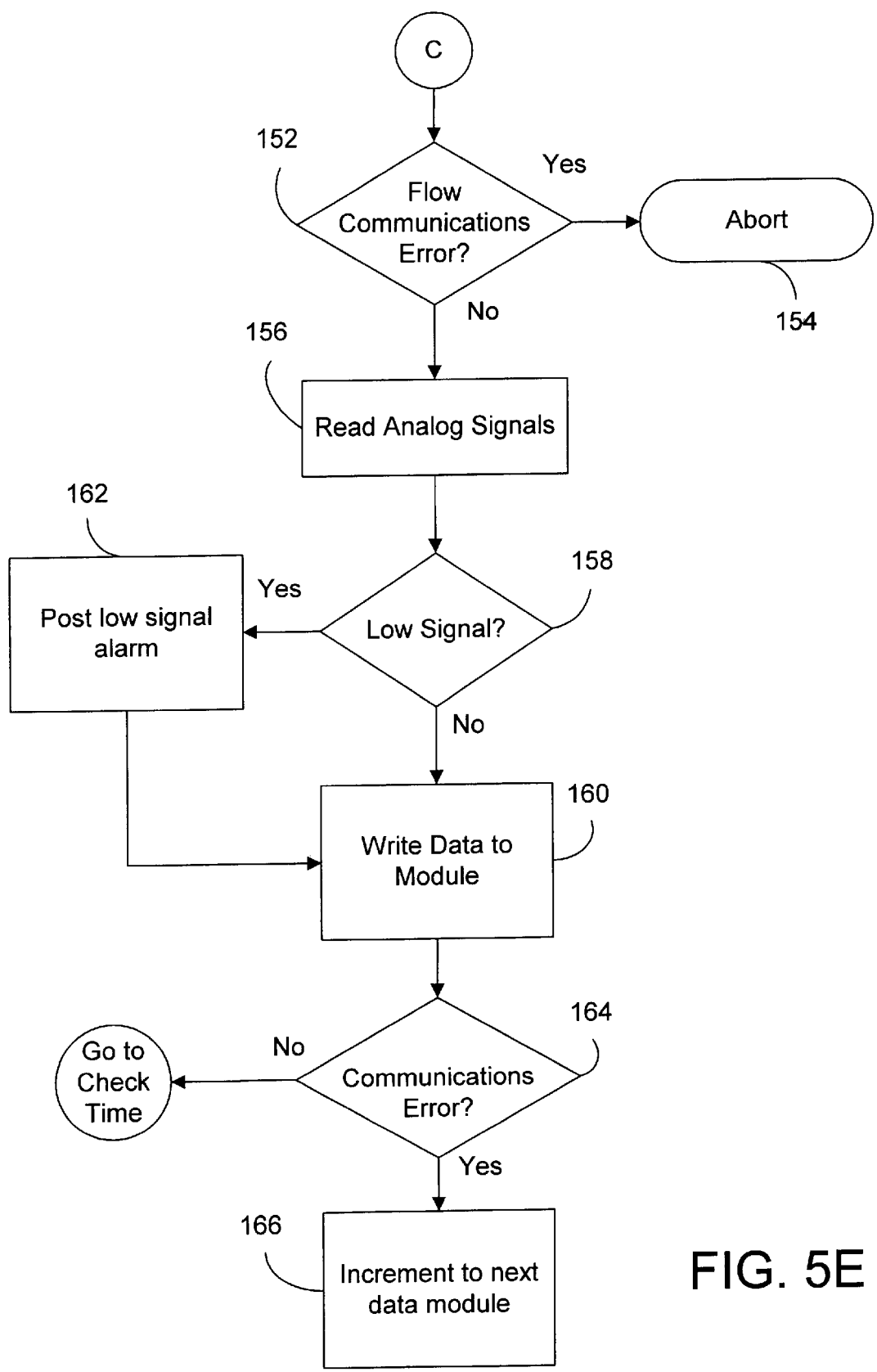

With reference to FIG. 4, the solenoid valves 48 within the control unit 12 are activated through a set of relays 72 and a relay controller 70, which in the preferred embodiment is manufactured by WinSystems Inc. The control unit 12 also includes a second relay controller 64 responsible for control of all CCM solenoid values 52. The relay controllers 64 and 70 are, in turn, controlled by a control interface 68, such as a digital control card also manufactured by WinSystems Inc. A wiper for each relay controller 64 and 70 is connected to a 24 Volt power bus. The normally open contact for each output of the controllers 64 and 70 is preferably connected to one end of a silicon "fly back" diode with the other end of each "fly back" diode being connected to ground.

After passing through the CCM 14, the gas passes through one of the two CCM selections solenoid valves 48 internal to the control unit 12. Suitable air inlet front panel connectors on the control unit 12 are each routed to an internal CCM selection solenoid valve 48. The solenoid valve 48 associated with the active CCM 14 is energized while the other solenoid valve 48 is inactive. The process gas is drawn through the flow regulator 44 and into the process gas pump 46. The process gas pump is energized through a relay 72, such as a 120 VAC relay, which is controlled by the relay controller 70.

Air is exhausted from the pump 46 and leaves the control unit 12 of the SCC 10 through a rear panel exhaust jack. The exhaust jack is preferably a ⅜" female Swagelok connector and is normally closed. In order for the SSC 10 to operate properly, the rear exhaust connector should have a mating connector installed to facilitate air flow through the SSC 10.

4. CCM Data Module

Figure 3:
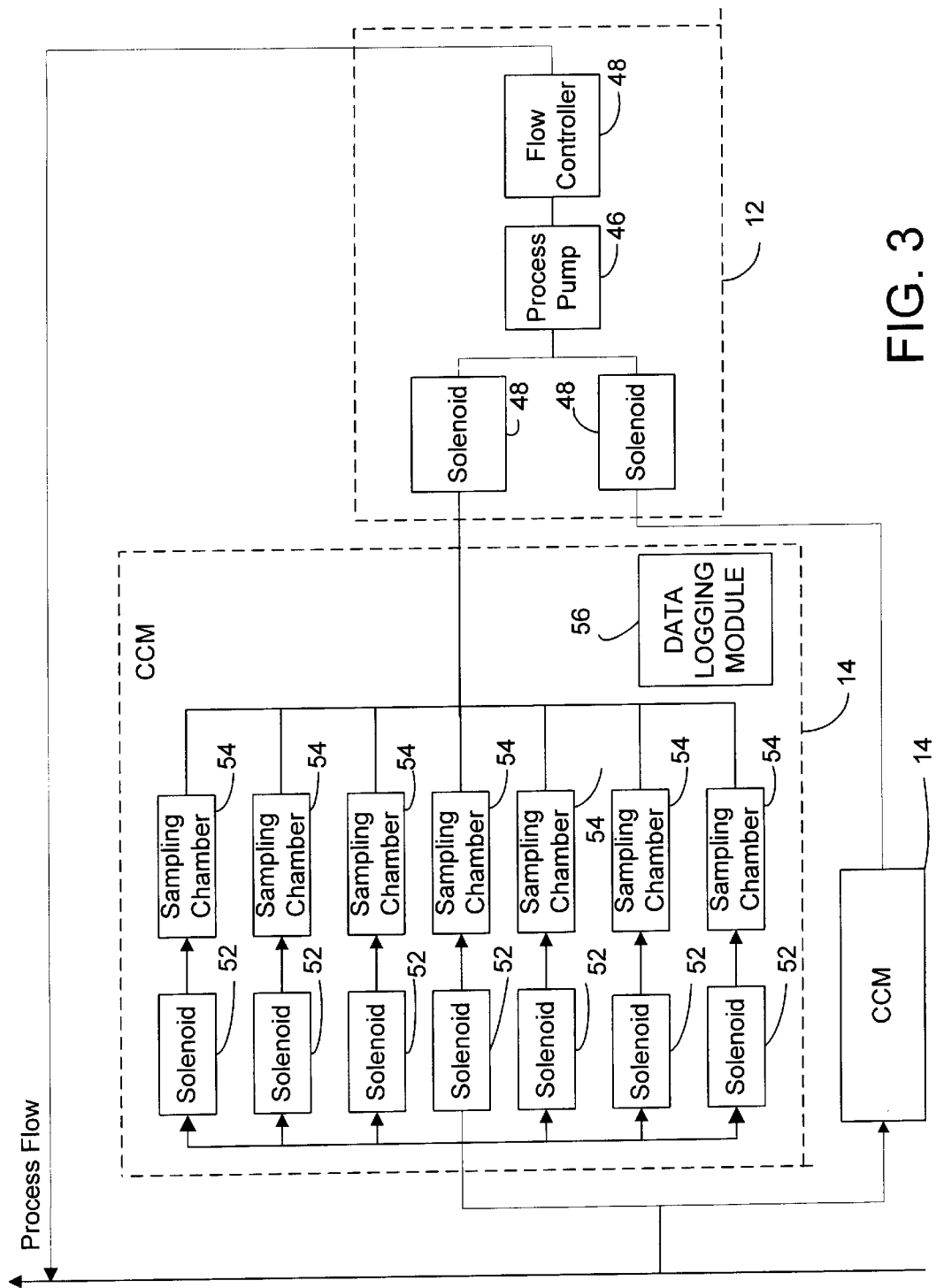
FIG. 3 is a gas flow block diagram of the sampling system of FIG. 1.

Each CCM 14, as shown in FIG. 3, includes a data logging module 56. In the preferred embodiment, the data module 56 is a Blue Earth brand BE-OIE data logging model with RS232 communications. The central processor 27 of the SSC 10 communicates with each data logging module 56 through a data logging interface 76, which is preferably a standard RS232 serial interface.

5. Cabinet Temperature

The thermocouple 36 for monitoring the internal cabinet temperature is preferably an Omega "E" type thermocouple, Omega part number CO1-E. The internal cabinet temperature is a reference only measurement used to indicate potential failures in an SSC cooling fan, other SSC equipment failures or a failure of the heating/cooling system of the SSC equipment room. If desired, the internal thermocouple 36 can be disconnected and an external thermocouple on the SSC 10 can alternatively be used.

6. Front Panel Controls

The control unit 12 also includes front panel controls including front panel switches 80 and indicators 82. The controls preferably include three lighted switches 80 for Start, Stop, and Reset, the flat panel display 26, and indicators 66 for the CCMs 14, such as two CCM indicator lights. Other accessible operator controls on the SSC 10 include a power ON/OFF switch located on the rear of the control unit 12.

The front panel lighted switches 80 are used to start and stop operation of the control unit 12 through a main SSC program, "TSC.EXE," and are used to verify unused CCM 14 status and clear alarm conditions. When the rear panel power switch on the SSC 10 is turned to the ON position, the control unit 12 automatically enters the main sampling operation. The user presses the "START" to begin normal operation of the SSC 10. If the user does not wish to being sampling operations, pressing the STOP switch will exit the program and place the operator at the DOS operating prompt on the SSC 10. One the START switch has been pressed, the front panel switches 80 extinguish while the SSC 10 verifies the presence of at least one usable CCM 14. During normal operation, the STOP and RESET switches 80 are illuminated, but not the START switch 80, indicating the SSC 10 will respond to either the STOP or RESET switch command. The STOP and RESET lights 82 will momentarily extinguish when the SSC 10 writes information to the CCM 14 or when the SSC 10 is attempting to recover from a fault condition, such as loss of flow through the CCM 14. The extinguished lights 82 indicate the SSC 10 will not respond to any push-button command during the time interval the lights 82 are extinguished.

The RESET switch 80 is used to verify the operability of an unused CCM 14 and to reset any alarm conditions that may have occurred. If an alarm condition occurs, as detected by alarm circuit 88, the SSC 10 will latch in the alarm relay unit until either the alarm condition has cleared and the front panel RESET switch 80 is depressed, or power is removed from the SSC 10. The RESET switch 80 may also be used to verify the correct operability of an unused CCM 14. During normal operation when a CCM 14 is replaced, the RESET switch 80 can be depressed to verify the replacement CCM 14 is operational and will be used after the CCM 14 in use has been exhausted. The RESET switch command verifies the SSC 10 can communicate with the unused CCM 14, the unused CCM 14 has a valid serial number assigned, and the unused CCM status flag is set to "NEW." The status of the unused CCM 14 is reported to the operator via the flat panel display 26 on the SSC 10. Failure to press the RESET switch 80 during CCM 14 change out will not prevent the CCM 14 from being used after the current CCM 14 is exhausted.

The CCM indicator lights 66 on the front of the control unit 12, directly above each CCM connector, indicate the CCM 14 currently in use. The CCM indicator 66 corresponding to the CCM 14 currently in use is illuminated while the other indicator 66 is not illuminated.

The flat panel display 26 on the front of the SSC 10 is used to provide operator feedback on the status of the SSC 10 and the CCM 14. The display 26 provides error messages, the current CCM chamber 54 being used, and, when the RESET switch 80 is depressed or the SSC 10 is first started, operating status of the CCMs 14. The front panel display 26 is also used in conjunction with the software utilities: SERIA.EXE, RECOVER.EXE, and 420CALIB.EXE.

7. Other Connections

A computer interface 84 is provided to connect the SSC 10 to an external computer 13, such as to facilitate data recovery and other uses. For instance, in the event a CCM 14 loses data, the data can be recovered from the SSC 10 by using the utility "RECOVER.EXE" and the interface 84. The control unit 12 preferably is able to print to the printer 28. A rear general purpose panel parallel port is provided to facilitate printing of information stored on the SSC 10 or to provide other communications.

8. Other Associated Hardware

The SSC 10 contains memory 24, which preferably comprises a static 1.44 Mbyte RAM drive manufactured by WinSystems, Inc. The memory 24 contains the ROM DOS operating system and the programs "TSC.EXE", "RECOVER.EXE," "420CALIB.EXE," "SERIA.EXE," "AUTOEXE.BAT," "CCM1.TXT," and "CCM2.TXT." The "TSC.EXE" file is the main sampling program and the other ".EXE" files include calibration and service utilities. The "TXT" files are files that mirror the most recently run CCM1 and CCM2 CCM data files and can be used to recover data in the event of a data logger failure in the modules 56. The static ram drive 24 contains a permanently mounted battery having a life expectancy of greater than five years and three static ram chips configured for a 1.44 Mbyte disk.

C. Software

1. Initial Startup

A main loop of processing for the control unit 12 will now be described with references to FIGS. 5A to 5D. When processing initially starts at step 100, the control unit 12 first executes the function "do defaults." The "do defaults" functions initialize global variables, sets the CCM selection solenoid valve 48 to CCM1, toggles the solenoid 52 that corresponds to the CCM chamber #1, and activates the CCM1 front panel indicator light 82. Additionally, the "do defaults" function establishes communications with the internal flow controller 44 and sends the flow controller 44 the default flow control rate. If an error occurs in establishing communications with the flow controller 44, an error condition is returned to the central processor 27, the central processor 27 reports a flow controller communications error, and operations cease.

After performing the "do defaults" function, the central processor 27 polls the function "read switch" at step 102 to see if the front panel START switch 80 has been depressed. If the STOP switch 80 is depressed, the central processor 27 will end the program at step 112 and return to the DOS operating system. Otherwise, the central processor 27 will wait indefinitely for the START switch 80 to be pressed. After the START switch 80 is pressed, as determined at step 104, the central processor 27 calls the function "toggle lights" to extinguish the front panel switch indicators 82. Next the central processor 27 calls the main function "check module" at step 110 to check the status of the CCM2 data module 56. The central processor 27 calls the "read module" function at step 114 to verify the status of the CCM1 unit 14 and to acquire the sampling rate and internal flow rate to be used for the duration of the CCM's 14 use. In the event CCM1 14 cannot be used, as determined at step 116, the central processor 27 increments to CCM2 14 at step 124 and attempts to use the CCM2 unit 14 for data collection. If no modules 14 are available, the central processor 27 terminates program operation at step 130.

After an available CCM 114 had been identified, the central processor 27 starts the pump 46, which is preferably a Gast diaphragm pump, by calling the function "start pump" with a value of one. A message is displayed telling the user that all systems have been checked out. The SSC 10 enters a 3 second delay before proceeding to ensure the SSC 10 is stable before sampling began. This delay is especially critical if very short duration sampling rates are used, such as 0.1 minutes per sample, to ensure that proper flow has been established and a loss of unit flow error doesn't occur due to startup transients.

The SSC 10 acquires the current time at step 122 and, based on the current sample rate, calculates the next time the SSC 10 needs to sample the data and the next time the CCM 14 needs to increment to the next available chamber 54. At this point, the central processor 27 enters a infinite loop. At step 140, the central processor 27 reads the front panel switches 80 through the "read switch" command, acquires the current time and compares the time against the next time to sample data/increment the CCM chamber 54.

If the time has expired to acquire a sample, the central processor 27 toggles the front panel switch indicators 82 to off via the function "toggle lights," calls the function "read stack flow" at step 142, "read unit flow," "read cabinet temp," "send module data," and "write to disk" at step 160. Between the calling of each function, a print command is issued that prints nothing to the screen. This command was done to insert a small amount of delay between each function call. After calling the above functions, the central processor 27 calculates the next time a sample will be acquired based on the sample rate and the current time. The front panel STOP and RESET switch indicators 82 are illuminated by calling the function "toggle lights."

If the time has expired to increment the CCM chamber 54, the central processor 27 increments the global variable "mod counter" and calls the "increment chamber" function at step 132. The "increment chamber" function increments to the chamber number corresponding to the "mod counter" variable. If the last chamber 54 has been used, the central processor 27 issues a switch CCM request at step 138 through an "increment chamber" function. The "increment chamber" function is responsible for updating the global variable "daytime" that indicates when the chamber 54 is to be incremented the next time.

2. Reading CCM Modules

Figure 6A:
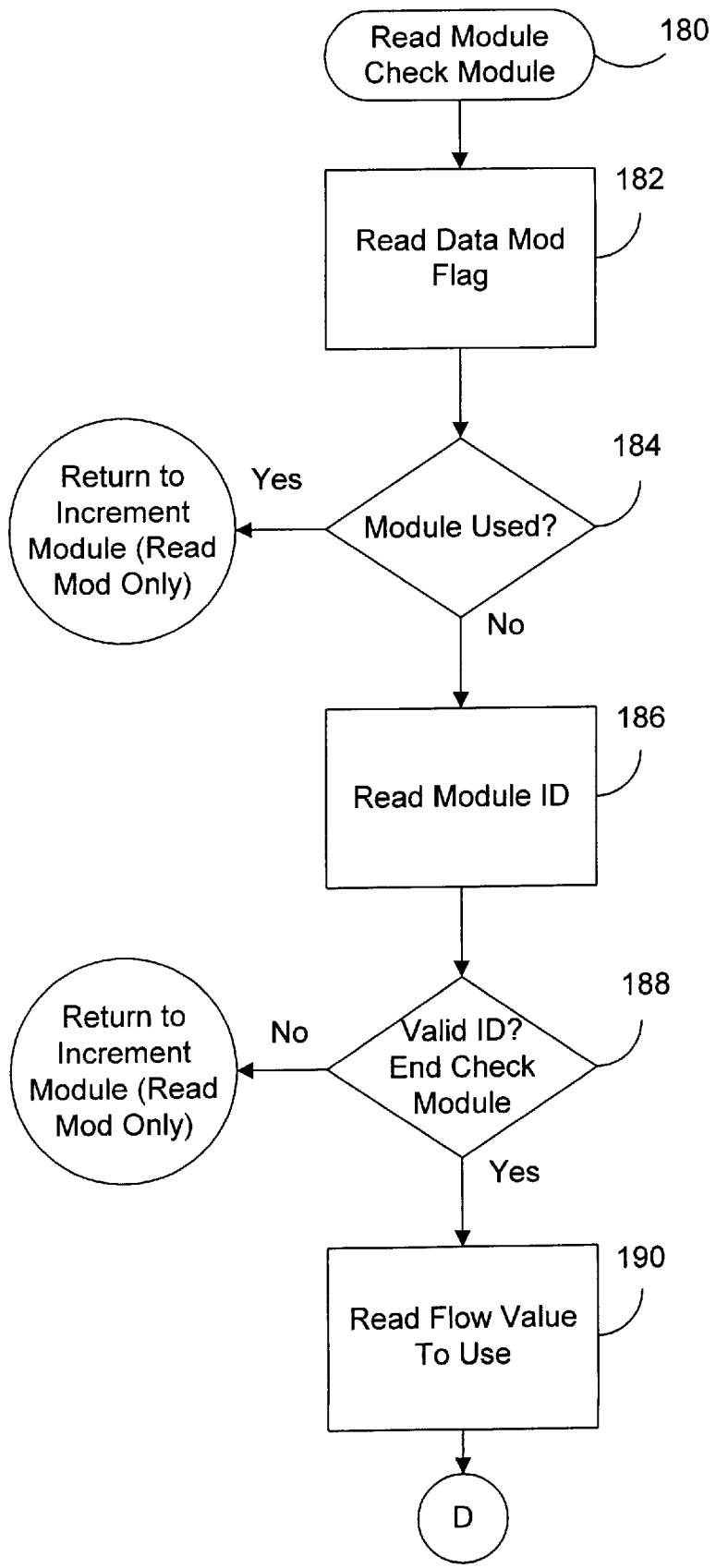
FIGS. 6A and 6B are flow charts depicting a read routine processing for the sampling system of FIG. 1.
Figure 6B:
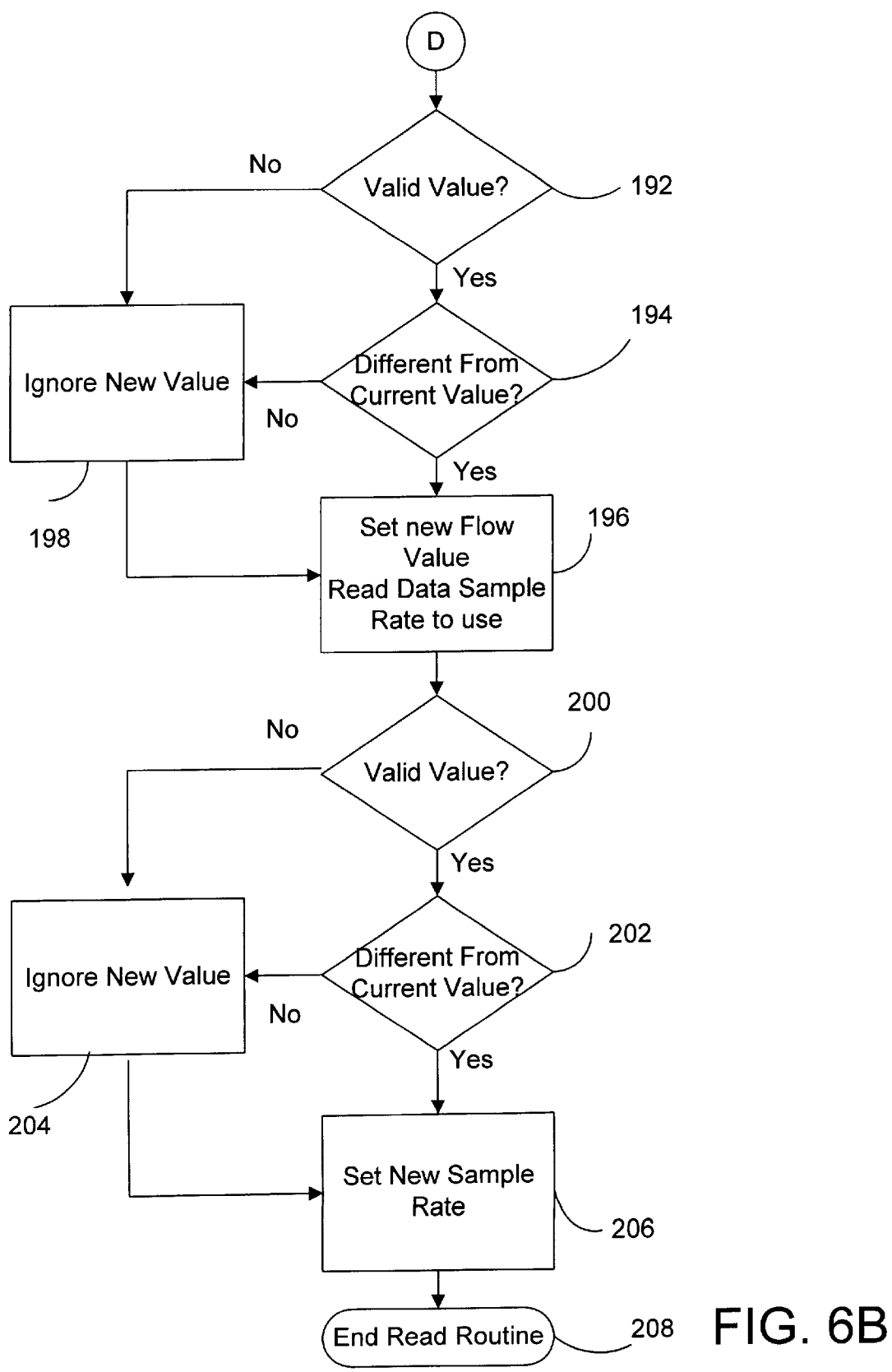
Figure 7:
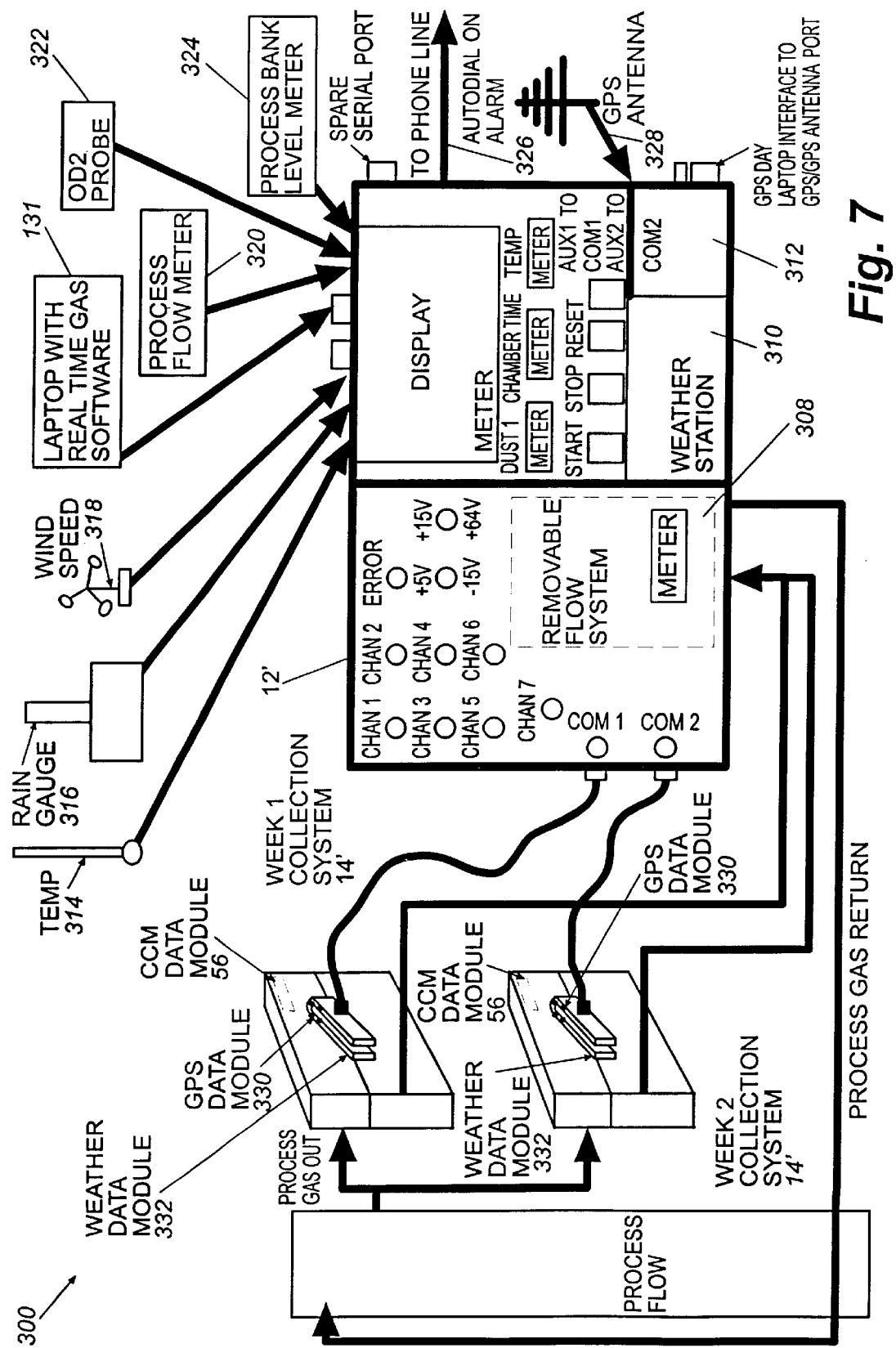
FIG. 7 is a block diagram of a sampling system according to a second preferred embodiment of the invention.

The process for reading data from a CCM 14 will now be described with reference to FIGS. 6A and 6B. The function "read module" is called at step 182 during initial startup by the central processor 27 through both the main program and through the "increment module" function. The "read module" function is called by the central processor 27 when the current CCM 14 is exhausted and the SSC 10 needs to switch CCMs 14 or when an error condition renders the current CCM 14 inoperable. The "read module" function is responsible for establishing communications with the data module 56, reading the data module ID, status flag, system sampling rate, and system flow rate.

The "read module" function calls the "toggle lights" function to extinguish the front panel switch indicators 82. Next the central processor 27 selects the appropriate communications port based on which CCM 14 the SSC 10 is trying to establish communications with COM3 for CCM1 or COM4 for CCM2. This value is contained in the global variable "module" and is valid for values "1" and not "1."

The "read module" sets up serial communications by calling the function "setserial." "Setserial" selects the I/O port corresponding to the COM4 port, sets the speed, parity, number of bits, and stop bits for correct communications using the functions "setport," "setspeed," and "setothers." If a failure occurs, a non zero value is returned indicating the software could not set the parameters for proper communications. If the function fails, an error message "Communications Problem on CCMX" is displayed, where X corresponds to the CCM 14 that failed. The failed communications channel is closed, and the function "increment module" is called to increment to the next CCM unit 14.

The "read module" next calls the "initserial" function. The "initserial" function sets a receive interrupt vector to store incoming data, turns the communications port receiver on, and initializes the receive buffer counter.

The "read module" function sends a "SI" command to the data module 56, corresponding to Send ID. This command is executed by the function "send command." The "send command" function enters a loop where it sends a command string one character at a time via the "serialout" function. After each character is sent out, the "send command" function reads the character echoed back, via the "getccb" function, from the Blue Earth module 56. If the character received does not match the character sent, a flag is set. The transmission/receive loop is terminated when a "\t" character is the string to be transmitted. If a failure occurred, the function attempts to re-send the string a second time. If an error occurs the second time, an error condition is returned by the "send command" function. If the "read module" function receives an error from the "send command" function, the function "increment module" is called and a communications error is displayed. If the "send command" function is successful, the function "read int" is called at step 186 to read the 16 bit serial number returned by the Blue Earth data module 56. If the serial number is greater than 32,000 or less than 100, as determined by step 188, an invalid serial number is displayed and the "increment module" function is called.

If the "read module" function receives a valid serial number, the central processor 27 next sends the "SC" command, corresponding to Send Clear Flag, by using the "send command" function. If the CCM data module 56 has been reset since its last use via the "CCMSET.EXE" utility, the Blue Earth module 56 should return a zero. This value is read by a call to the function, "getccb." If a non-zero value is returned, an error message indicating a used CCM 14 is displayed and the function "increment module" is called. Otherwise, the central processor 27 proceeds with the next command.

The next command the central processor 27 sends through the "read module" function to the Blue Earth module 56 is the "SF," corresponding to Send unit Flow rate. The value is read by the central processor 27 at step 190 by a call to the function "read 32." The "read 32" function reads a 32 bit floating point number by calling the "read int" function twice. If the value returned by "read 32" is greater than the maximum or less than the minimum flow rates, which are defined in "TSC.H" as MINFLOW and MAXFLOW, then the default flow rate, defined in "TSCH.H" as DEFLOW, is used. Otherwise, the flow rate read from the SSC 10 is assigned to the current flow rate. The flow control rate is passed to the Sierra flow controller 44.

The last command issued to the Blue Earth data module 56 by "read module" is the "ST" command, corresponding to Send Sampling Rate. The sampling rate is read by the central processor 27 at step 196 through the function "read 32." If the sampling rate is greater than zero, the central processor 27 updates the current sampling rate at step 206. The new sampling rate is reflected after the next data sample is acquired, when the next sample time is computed again.

The central processor 27 calls the function "write to disk" at step 206 to open a new data file corresponding to the current CCM 14. This function call in effect destroys any data that was saved by the previous CCM 14 operating on this CCM channel. The CCM selection solenoid valve 52 is set to the new CCM channel by a call to "set flow valve," the serial communications channel is closed by a call to "closeserial," and the front panel switch indicators 82 for STOP and RESET are illuminated by calling "toggle lights."

3. Checking CCM Modules

The function "check module" contains many of the same attributes as "read module." The "check module" function is used by the central processor 27 to verify a CCM data module 56 is present, the "used/new" flag is set to "new," and the module contains a valid serial number. This function is called by the central processor 27 upon initial startup and any time the "RESET" switch is depressed, called by the "read_switch" function. The function acts on the CCM 14 not currently in use and is intended to provide operator feedback as to the status of the unused CCM data module 56.

The "check_module" function first toggles the front panel switch indicators 82 to the off state by calling the function "toggle_lights." Next, the central processor 27 establishes communications with the unused CCM 14 by calling the functions "setserial" and "initserial." The data module 56 on the unused CCM 14 is requested to send its serial number and clear flag in the same manner as the "read module" function. A communications failure or invalid serial number results in an error message being posted to the operator and the function terminating. Unlike the "read_module" function, the "increment_module" function is not called in the event of a failure.

After the "check_module" function has completed, the lights 82 are toggled back to the on state by calling "toggle_lights." In the event the function failed, the function calling "check_module" is responsible for issuing the "toggle_lights" command to toggle the front panel indicators 82 to the on state.

4. Controlling Flow

Normal flow control is invoked by the central processor 27 through the main program by calling the functions "increment_chamber" at step 138 and "increment module" at step 136. During initial startup, the "do_defaults" function opens the CCM1 flow selection valve 48 as well as the first chamber 54 of the CCM 14 connected to CCM1. A loss of internal flow error, initiated from the "read_unit_flow" function, will result in the "read_unit_flow" function initiating calls to the "increment_chamber" and potentially the "increment_module" functions. A communications error with the data module 56 will result in a call to "increment_module" as well.

The "increment_chamber" function is responsible for incrementing solenoid valves 52 on the active CCM 14 and for illuminating the SSC front panel CCM light 82 for the active CCM 14. After all seven chambers 54 have been used, the "increment_chamber" function is responsible for zeroing the chamber count, closing all solenoid valves 52 on the used CCM 14, switching the SSC front panel CCM indicators 82, calling the "increment_module" function, and activating the first solenoid 52 on the new CCM 14. The "increment_chamber" function is called by the central processor 27 through the main program after the 24 hours has elapsed on the current chamber 54 during normal operation. If the sampling rate is less than 6.0 minutes per sample in the data module 56, the sampling rate is assumed to be an accelerated test rate and the chambers 54 are incremental at a rate that corresponds to 1680 sample records divided by 7 chambers, corresponding the maximum number of samples that would be obtained during normal operation. If a loss of flow is detected by the function "read_unit_flow," the "read_unit_flow" will delay for 5 seconds and read the unit flow rate again. This loop continues until all chambers 54 and CCMs 14 have been exhausted or until flow is reestablished. The "increment_chamber" function switches to the next CCM 14 by invoking the "increment_module" function when the chamber count exceeds 7 chambers.

The "set_flow_valve" function switches the solenoid valves 52 internal to the SSC 10 that are responsible for controlling air flow from the active CCM 14. The function also sets the first solenoid valve 52 on the active CCM 14 and the CCM light 66 on the front panel of the SSC 10 to the active CCM 14. Part of this function is redundant with the function "increment_chamber." The redundancy was permitted to prevent a CPU stack in the central processor 27 from becoming excessive during error conditions. In other words, certain error conditions could potentially result in functions calling other functions that call the invoking function thus causing the function calling process to become excessive and the central processor 27 not being able to recover after the error has been handled. The other task the "set_flow_valve" function performs is a call to "increment_module."

The central processor 27 calls the "increment_module" function at step 136 to increment communications and flow to the next CCM 14. The function accomplishes this by calling the "set_flow_valve" and "read_module" functions. A global counter, "mod_retrys" keeps track of the successive number of times the function has been called. If the function is called twice successfully, then the function knows all CCMs 14 have been tried and no CCMs 14 are available. If no CCMS 14 are available, the functions posts an error message to the display 26, writes the error message to the active temporary file on the SSC RAM drive 24, and calls the "do_error" function to sound the alarm and exit the program. The "mod_retrys" variable is zeroed after a successful completion of the "read_module" function or after a successful data transmission by the "send_module_data" function.

5. Regulating Flow

Flow regulation is accomplished via the Sierra brand flow controller 44 internal to the SSC 10. The flow controller 44 is intelligent and receives flow regulation rates from and, upon request, reports actual flow rates to the central processor 27.

The flow controller 44 is initialized by the "do default" function at startup. The desired flow rate is set in the "read_module" function each time the "read_module" function is invoked. The actual flow rate is read by the function "read_unit_flow." The "read_unit_flow" function is invoked by the central processor 27 through the main program after time has expired to acquire the next sample rate.

6. Reading Stack Flow

Stack flow is read by a call to the function "read_stack_flow." The "read_stack_flow" function is called by the central processor 27 through the main program after expiration of the sample rate time. The analog interface 34 responsible for reading stack flow and temperature measurements is initialized at the start of the program by the function "initialize_analog," called from the "do_defaults" function.

The analog interface 34 has a control and data register that is used to set up the card and acquire data. The individual channels of the interface 34 are programmed via the "initialize_analog" function for specific data acquisition, i.e. voltage, resistance, or current. In this example, channel 0 of the sensor input card is programmed for a type "E" thermocouple while channel 4 is programmed for a 4–20 milliamp acquisition. The remaining channels in this example are not programmed, although other programming options are available.

The "read_stack_flow" function is responsible for acquiring the 4–20 milliamp current value for stack flow measurements. The "read_stack_flow" function first polls a data register of the analog interface 34 to see if data is available to be read from the stack flow channel. If data is available, the function acquires the least significant bits of the 16 bit stack flow value from the data register. Next the "read_stack_flow" function polls the data register to see if the upper bits are available. When the upper bits become available, the function acquires the most significant bits from the data register of the analog interface 34.

If the stack flow value is outside of the expected integer value corresponding to a 4–20 milliamp signal, a stack flow failure flag is incremented. Two successive failures results in a stack flow error being generated. The alarm is sounded and remains active until the alarm condition is cleared and the RESET button 80 on the front panel of the SSC 10 is pressed. An error message is logged to the temporary data file on the SSC 10 and an error message is logged on the active CCM data module 56 on the next data logging interval.

7. Reading Cabinet Temperature

The cabinet temperature of the SSC 10 is read by a call to the function "read_cabinet_temp." The "read_cabinet_temp" function is called by the central processor 27 through the main program after expiration of the sample rate time. The analog interface 34 responsible for reading cabinet temperature is also used to read stack flow measurements.

The "read_cabinet_temp" function is responsible for acquiring the voltage value corresponding to the internal cabinet temperature of the control unit 12. The "read_cabinet_temp" function first polls the control register of the analog interface 34 to see if data is available to be read from the cabinet temperature channel. If data is available, the function acquires the least significant bits of the 16 bit cabinet temperature value from the analog interface 34. Next the "read_cabinet_temp" function polls the analog interface 34 to see if the upper bits are available. When the upper bits become available, the function acquires the most significant bits from the data register of the analog interface 34. In practice, the temperature value logged to the CCM data module 56 has an eight bit representation of the 16 bit temperature value and was done to conserve space on the data module 56. Since the cabinet temperature is not a critical parameter, an 8 bit representation is sufficient.

If the cabinet temperature exceeds 45 degrees Centigrade, a high temperature flag incremented. Two successive high temperature readings will result in a warning message being posted to the temporary data file for the active CCM 14, the data module 56 of the active CCM, and the SSC display 26. All error messages recorded to the temporary data files in memory 24 and to the CCM data modules 56 are recorded during the next time data is written.

8. Data Logging

Data is logged to a temporary data file in memory 24 via the function "write_to_disk" and to the CCM data module 56, via the function "send_module_data" after expiration of the sampling rate time and after acquisition of all data, i.e. stack flow, unit flow, and cabinet temperature. Both functions are called by the central processor 27 through the main program after all the data acquisition functions have been called.

The "send_module_data" function sends the command "RD" for Receive Data to the active CCM 14 via a call to the function "send_command." If the "send_command" function returns an error, the "send_module_data" function calls the "increment_module" function to advance to the next available CCM 14. Otherwise, the "send_module_data" function acquires the current day, hours, and minutes via the functions "gettime" and "getdate." The day, hours, and minutes are converted to 8 bit values to conserve space on the data module 56 and are sent to the CCM data module 56 via three successive calls to the function "send_char." The "send_char" function is a modified version of the "send_command" function. "Send_char" is designed to send only one character and compare the value echoed back by the CCM data module 56. It is preferable to implement a specialized version of "send_command" as the "send command" termination character '\t' overlaps with the valid data range that can be transmitted by "send_char." A failure returned by "send_char" causes the "send_module_data" function to post an error message and advance to the next CCM 14 via a call to "increment_module."

After sending the date and time information, the "send_module_data" function sends until flow and stack flow information via calls to the "send_int" function. "Send_int" receives a 16 bit integer value and calls the "send_char" function twice, once for the lower eight bits and once for the upper 8 bits. "Send_int" passes the same error as "send_char" and the "send_module_data" function handles the error in the same manner.

The next parameter passed is the cabinet temperature via a call to "send char." The current chamber count and any error codes are passed as the last parameter via a call to "send_int." The 8 bit "err msg" variable represents two four bit parameters. The upper 4 bits (4–7) correspond to error codes with bit 7 being set for a high temperature alarm, bit 6 being set for a no canisters available alarm, bit 5 being set for the loss of unit flow alarm, and bit 4 being set for a loss of stack flow alarm. The lower 4 bits (0–3) represent the active chamber, with values of 1 to 7 corresponding to chambers 1 to 7. The no canisters available error will not be recorded to the CCM data module 56 as the program has no CCMs data modules 56 to write when this alarm occurs. However, the no canister available error message is recorded to the temporary data file in memory 24 and the error message can be retrieved by using the "Recover.exe" utility on the SSC 10.

The "write_to_disk" function is called by the central processor 27 from the main program immediately after a call to the "send_module_data" function. Additionally, the function is called from the function "increment_module" in the event of a no canister available alarm so that the error code may be captured before the program terminates.

The "write_to_disk" function, when passed a value of zero, opens a new file for the current CCM, i.e. CCM1.txt or CCM2.txt, on the SSC 10. The "write_to_disk" function, when passed a value of one, writes a backup copy of the information sent to the CCM data module 56 to the CCMX.txt data file in memory 24. One exception is when the no canister available alarm is posted by the "increment_module" function, in which the information is not written to the data module 56 as no available module 56 could be found.

A purpose of creating temporary data files in memory 24 is to recover data in the event of a CCM data module 56 failure. The temporary data file, during normal operation, will remain intact for seven days after the corresponding CCM 14 has been exhausted. In the event of an active CCM 14 failing, the data file will be erased when the SSC 10 fails to the next CCM 14 channel, assuming an available CCM 14 is connected to the next CCM channel. If the CCM 14 fails and no CCM 14 is available, the temporary data files will not be erased.

The CCM data module 56 sets the NEW/USED flag to used on the first valid data transmission. In practice, the NEW/USED flag is the day field of the first record logged. As there are no zero days in the month, valid range 1–31, the recording of the first data transmission sets the module to the USED state. The module is set to the NEW state by the central processor 27 through the program "CCMSET.exe" with the command "RC" for Receive Clear.

9. Front Panel Controls and Indicators

The SSC front panel switches 80 are read by the central processor 27 through function "read_switch." The front panel switch indicators 82 are controlled by the central processor 27 through the function "toggle_lights" and the front panel CCM indicators 66 are controlled by the central processor 27 through functions "increment_chamber" and "set_flow_valves." The function "read_switch" is called by the main program during startup and during normal operation when data is not being acquired or written. The function "toggle_lights" is called during normal operation by the main program after the expiration of 24 hours or by the end of "read_unit_flow" function during error conditions. The function "set_flow_valves" is called by the function "increment_module" when a CCM failure occurs or when all chambers 54 have been exhausted in an active CCM 14.

The function "read_switch" returns the 16 bit value corresponding to the switch depressed. If the STOP switch 80 is depressed, the "read_switch" function performs cleanup activities and exits the program. If the RESET switch 80 is depressed, the "read_switch" function clears the alarm, zeroes any error messages present in the "err_msg" variable, and initiates a "check_module" function call for the unused CCM 14.

The "toggle_lights" function toggles the switch indicators 82 on the front panel of the SSC 10. The "toggle_lights" function receives a 16 bit value corresponding to the lights to be illuminated. In practice, only the three most significant bits of the 16 bit value are used for light control. The function is called prior to startup activities to illuminate the START switch 80 on the front panel, is called during startup to extinguish all front switch indicators 82, is called during normal operations to illuminate the STOP and RESET indicators 82, and is called during the data acquisition and data logging operations to extinguish all front panel switch indicators 82. The switches 80 preferably only respond to operator actions when they are illuminated. The only exception is during initial startup when the START light 82 is illuminated. During initial startup, the STOP switch 80 is a valid switch action to terminate the program.

The "increment_chamber" and "set_flow_valve" functions control the CCM indicators 66 on the front panel. The CCM indicators 66 are used to indicate the active CCM chamber 54. During normal operation, the "increment_chamber" function has control of the active CCM indicator 66. During error conditions, the CCM indicator 66 can be controlled by the "set_flow_valve" function, if necessary.

10. Setting CCM Modules

Before using a CCM 14, the data module 56 on the associated CCM 14 must first be initialized by the central processor 27 by using the utility "CCMSET.exe." The "CCMSET.exe" utility is used to assign the CCM data module 56 a valid serial number in the range of 100 to 32,000, set the CCM NEW/USED flag to NEW, record the sample rate and CCM flow rate to be used by the SSC 10 for the duration of the CCM's 14 use. The "CCMSET.exe" program can be run from any PC compatible computer 13 with an RS-232 serial port assigned to COM1 or COM2. A cable interfaces the PC 13 with the CCM 14 and supplies power to the data module 56 on the CCM unit 14.

The "CCMSET" utility requests the user to enter the serial port COM1 or COM2 to which the CCM 14 is connected. The utility opens the serial communication channel with a call to "setserial." A default data file is contained on the host PC 13 that contains the default sample and CCM flow control rates. The user can modify these values by using any word processing program and save the file as a text file. The sample rate should be included on the first two lines of the file. The values acquired for the default file are displayed to the user later in the program.

The utility attempts to set the NEW/USED flag in the CCM data module 56 by sending the command "RC" for Receive Clear flag. The utility verifies the flag is set to new by passing the command "SC" for Send Clear flag and reading the returned value. If the data module returns a non-zero value, the command sequence is repeated. If the return value is a non-zero number a second time, it is assumed the data module 56 is faulty and the "CCMSET.exe" program displays an error message and aborts operation. Otherwise, the program continues and requests the CCM data module's 56 current serial number with the command "SI" SEND ID. The "CCMSET" utility stores the module serial number and displays it to the operator. If the operator presses the <ENTER> key, the current serial number is retained, or else the serial number is updated to the new value in the "CCMSET.exe" program. Next the user is prompted with the default sampling rate. If the user wishes to change the value, the new value is entered at this point. Values less than a certain amount, such as 6.0 minutes per sample, may result in the warning message "THIS VALUE CAN ONLY BE USED FOR TESTING! ARE YOU SURE YOU WANT THIS VALUE?." Any keypress other than 'N' results in the value being accepted. If a 'N' is pressed, the user is again prompted for a valid sample rate. The "CCMSET.exe" program next displays the default CCM flow control rate. The operator is given an opportunity to change this value. If the value is changed, the internal CCM flow control rate is updated.

After all data parameters have been set, the "CCMSET.exe" program transfers the data to the CCM data module 56. The clear flag is sent via the command string "RC" for Receive Clear. The serial number is sent, via a call to the function "send_int", immediately after the command "RI" for Receive ID is issued to the central processor 27. The CCM flow rate is sent via the "send_float" function immediately after the command "RF" for Receive Flow is issued. The data sample rate is sent via the function call "send_float" after the command "RT" for Receive Sample Rate is issued. An operator message is displayed after each transmission letting the operator know the clear flag, the serial number, the flow rate, and the sample rate were sent. Additionally the actual flow and sample rates are displayed on display 26.

11. Reading CCM Data

The data contained on the CCM data module 56 is retrieved by using the PC based utility "CCMREAD.exe." The host PC 13 interfaces with the CCM 14 in the same manner as the "CCMSET.exe" utility. Upon starting the utility "CCMREAD.exe", the user is prompted for a file name in which to store the information. The operator should enter a file name corresponding to the DOS "8.3" format. An invalid file name or a failure to successfully open the specified file will result in the program terminating. Next the user is prompted for the conversion factor to use in converting the stack flow value to an actual flow rate. There are three conversions currently used: 3.125 for the Tank Farm, 1500 for the Offgas, and 1562.5 for the HVAC, although other conversions may be used. These conversions correspond to maximum flow stack rates of 50, 24000, and 25000 standard cubic feet, respectively.

The "CCMREAD.exe" program enters a loop in which it retrieves data from the CCM data module 56. The "CCMREAD.exe" utility issues the command "SD" for Send Data to the data module 56. The data module 56 sends the next record of data each time the command is issued. The data module 56 resets the record counter after the last record has been sent or when power is removed from the unit. After the last record is sent, the data module 56 sends a zero for the day variable signaling the "CCMREAD.exe" utility that the last record has been sent. As each record is received, the "CCMREAD.exe" utility records the information in the specified file with a tab between data and a line in return after each record entry. The unit flow is converted to a standard unit per liter value by using the conversion constant 1/375 and the stack flow is converted according to the conversion factor selected by the operator prior to writing the values to the file. The received variable "err_msg" variable is broken out into the active CCM chamber number and error messages. The error number is converted to a one character symbol, such as S for Stack Flow, U for Unit Flow, C for Canister Failure, and T for Temperature, and any error symbols are written to the file, preferably with no tabs between successive error codes. The program terminates when a zero is received in the day variable. The data written to the file is echoed to the PC 13 so that the user can verify that data transmission is occurring properly. A normal download sequence can take up to 1 to 2 hours. The resultant file is suitable for use in Excel and other spreadsheet programs capable of processing a tab separated value format. A normal acquisition may result in 1680 records.

12. Recovering Lost Data

In the event a CCM data module 56 fails, the data can be recovered from the SSC 10, provided the SSC 10 has not used the CCM channel the failed data module 56 used since the failed data module 56 was removed from service. The SSC utility "Recover.exe" transfers the specified temporary CCM data file to an available CCM data module 56 via the read RS-232 serial port on the SSC 10.

The utility "Recover.exe" is started from the SSC 10 by connecting the keyboard 29 to the control unit 12, pressing the front panel STOP button, and at the DOS prompt entering <RECOVER>. The utility "Recover.exe" prompts the user to connect an available CCM 14 to the rear panel of the SSC 10. Once the CCM 14 is connected, the operator specifies the file to download and the program verifies the NEW/USED flag is set to new by passing the command "SC" for send clear flag, the program downloads data to the CCM 14.

The utility "Recover.exe" opens the file specified by the user, CCM1.txt or CCM2.txt, and sends the command "RD" to the CCM data module 56. The utility sends data to the module 56 in the same manner as the "send_module_data" function in the main control program, "tsc.exe." The "Recover.exe" program continues the "RD" and data transmission sequence until an end of file is encountered in the CCMx.TXT file. Once the end of the file is encountered, the program closes the COM2 port, the temporary data file, and exits the program. During data transmission, the data sent is echoed to the display 26 so that the user can verify that data transmission is occurring properly. A normal download may take up to 2 to 3 hours. After the data has been recovered, the information is downloaded to a PC 13 via the utility "CCMREAD.exe."

13. Verifying Stack Flow Calibration

The SSC stack flow measurement accuracy can be verified by the central processor 27 by using the utility "420calib.exe." The software uses the same board level commands as the main sampling program, "tsc.exe", to setup and read measurements from the analog interface 34.

In order to use the "420calib.exe" utility, a calibrated 4–20 milliamp source is connected to the analog interface 34, via the associated SSC rear sensor input jack. Since the temperature can contribute to the error of the SSC 4–20 milliamp measurement equipment, the "420calib.exe" program reports the cabinet temperature of the SSC 10 at the beginning of the program and again at the end. After the program has been run multiple times over a period of months, this temperature data can be used to determine if any significant error results from temperature changes in SSC 10.

At the start of the "420calib.exe" program, the analog interface 34 is initialized by the central processor 27 by calling the function "initialize_analog." The "initialize_analog" function is a copy of the "initialize_analog" function used in the main sampling program "tsc.exe." The function is responsible for setting up the stack flow 4–20 milliamp channel and the internal temperature channel on the analog interface 34. The utility begins by calling the function "read_cabinet_temp" to report the internal cabinet temperature prior to taking the first current reading. The "read_cabinet_temp" is a copy of the "read_cabinet_temp" function found in the main SSC program, "tsc.exe" with the following exceptions. The "420calib.exe" version of "read_cabinet_temp" prints the read temperature to the display 26 and high temperature condition checking is removed.

Next the "420calib.exe" program enters a loop where it invokes the "read_stack_flow" function 5 times, corresponding to 4, 8, 12, 16, and 20 milliamp readings. Prior to each invocation of "read_stack_flow," the main program displays a message requesting the user to adjust the current source to its new value, pause for 5 seconds, and press the <ENTER> key. The "420calib.exe" "read_stack_flow" function is identical to the "read_stack_flow" function found in the "tsc.exe" program except that the "420calib.exe" version removes stack flow failure checking.

14. Verifying Unit Flow Calibration

The SSC internal flow controller 44 calibration can be verified by the central processor 27 by using the utility "seria.exe." A calibrated flow meter capable of measuring 0 to 2.0 Standard Liters per Minute is required to perform the calibration.

The "seria.exe" flow controller verification procedure checks the air flow rate on the CCM1 inlet port. Since the CCM1 and CCM2 inlets are joined together past their respective internal solenoid valves 52, verification of the CCM2 inlet is not required. The "860demo.c" program energizes the internal pump 46 and CCM1 solenoid valve 48 at the beginning of the program and de-energizes the internal pump 46 and CCM1 solenoid valve 48 at the end of the program.

II. SSC2

A. Overview

Proper management of environmental sampling information gleaned from a variety of measurement technologies provides end-users, managers, regulators, and other interested parties a more complete sampling picture from which to make informed decisions. A Sampling System Controller according to a second embodiment of the invention (SSC2) 300 is a programmable, flow controlled atmospheric sampling system that incorporates information-handling technologies to properly manage data collected by other small self-contained instruments.

The SSC2 300 directly measures real-time data such as weather conditions, such as wind speed, wind direction, and precipitation, as well as other data, such as geographic position, and time. The system simultaneously provides a calibrated, vacuum induced flow for ambient or process air sampling. The pollutant of interest in the flowing air stream might be directly measured by real-time sensors or selectively sampled using discriminating, preconcentration media. The SCC2 300 provides with enhanced programming capabilities for unique sampling applications.

The SSC2 300 can sample up to three analog instruments at user defined intervals and record this information to an associated data module 56 mounted on a CCM 14. The instrumentation signal can either be a 0 to 5 Volt signal or 4 to 20 mA signal. Additionally, the control unit 12' can sequence the data acquisition of a portable weather station 310, global positioning system 312, and one other serial device to custom designed data logging modules. For example a portable weather station 310 has a data logging module that has been designed to work with the control unit 12.' The data logger, on command from the control unit 12,' records the weather information from the portable weather station 310.

The SSC2 300 can be operated over, theoretically, an infinite flow range. The SSC2 300 has a removable flow system 308 that allows the user to select a pump and flow controller best suited for a particular application. The removable flow system 308 has jumpers that provide an electronic signature to the control unit 12' for identification of the installed pumping system 308.

The SSC2 300 software is stored on a PCMCIA solid state drive. This arrangement allows the user to configure multiple controller setups on different disk drives, therefore allowing the user to quickly change the operating characteristics of the control unit 12.' All control unit 12' operating parameters are set through a custom Microsoft Windows based application. These parameters are transferred to the control unit 12' either through a host computer PCMCIA drive bay or through a host computer serial link. The SSC2 300 can be configured to start, stop, or alarm on any process variable, including portable weather station parameters and GPS parameters. Additionally, the SSC2 300 can start, stop, or enunciate an alarm via an internal phone modem. The flexibility of the SSC2 300 gives it the unique ability to monitor process or environmental atmospheric contaminants under a wide variety of conditions.

B. Ambient and Process Air Sampling and Analysis

No analytical result regardless of the accuracy and precision of the procedure can be any better than the quality of the sample submitted for analysis. The CCM 14' is designed to be a series of nonobtrusive flow cells. Each flow cell can be selectively filled with a distinct sample collection media. The flow cell can then be actively introduced to, and actively isolated from, the sampled air stream. One skilled in the art can select the appropriate collection media and exposure time or sample volume.

C. Serial Communications

The control unit 12' has three serial channels available. Two of the serial channels tie directly to the controller collection data modules for logging of instrumentation data, error conditions, and time and date stamps. Additionally, these two channels are used to sequence the starting and stopping of data recording on other data modules, such as weather station data modules 310 or global positioning data modules 312. The third serial channel is available to interface with a laptop computer 13' for data acquisition or controller setup.

A total of six serial channels in the control unit 12' tie directly from a serial device, such as a global positioning system 312 or weather station 310, to the associated data collection module, but are not connected to the central processor 27. The channels can be configured to operate sequentially in groups of three, in which three serial devices are tied to the CCM1 and CCM2 channels, or concurrently, in which three serial devices are tied to CCM1 or three different serial devices tied to CCM2. In the first configuration, the user can configure the SSC2 300 to sample for a specified period of time on the CCM1 channel. After the expiration of the specified time, the SSC2 300 switches to the CCM2 channel for sample and data collection. In the second configuration, both CCM1 and CCM2 channels operate concurrently to allow for the sampling of multiple elements.

The six independent serial channels are terminated at the CCM1, CCM2, AUX1, and AUX2 connectors. If desired, the AUX 1 or AUX2 connector may be used to interface with a laptop computer 13.' The laptop computer 13' can communicate with any of the dedicated serial devices directly for real time data acquisition. For instance, if a global positioning system 312 is used in the control unit 12,' a laptop computer 13' could be interfaced through one of the AUX connectors. The laptop 13' could report current position information based on information provided by the connected global positioning system 312. The use of a laptop computer 13' does not interfere with the normal data acquisition of the global positioning data acquisition module 312 nor does it interfere with the control unit 12' operation.

D. Data Acquisition Modules

The data acquisition modules, except for the CCMs 14,' are designed to operate with or without the SSC2 300. The data acquisition modules contain a selector switch to allow for the unit to begin acquisition such as when requested by the controller, upon application of power, or when requested by the user via a push-button. The modules can physically be connected directly to the CCM connector on the control unit 12,' to the CCM connector on the CCM 14,' or directly to the data acquisition device, such as the global positioning system 312 or weather station 310. Each CCM 14' preferably includes a GPS data module 330 for acquiring location information and a weather module 332 for acquiring weather information. The location information and weather information are recorded in the data module 56 within the CCM 14' and in a temporary file in the SSC 300.

E. Remote Control Functions

The SSC2 300 contains a modem giving it remote dial-in utilities. The modem gives the user the ability to start and stop the controller remotely as well as inquire about the SSC2 300 status or request data transmission, such as process instrumentation data, weather data, global positioning data. Coupled with a cellular phone and DC only operation, the SSC2 300 can be operated in any remote area within the coverage area of a local cellular provider.

F. Equipment Bays

The SSC2 300 contains bays for the portable weather station 310, the global positioning system 312, and the pump/flow control assembly 308. The bays eliminate much of the external cabling that would otherwise be required. The pump/flow control assembly 308 allows for easy interchange if there is a need to switch to a flow rate that is outside the range of the current pump/flow controller 308. Jumpers on the pump/flow control assembly 308 allow the SSC2 300 to detect and adjust operating parameters as required.

An additional advantage of the SSC2 300 is that the pump/flow control assembly 308 is an isolated subsystem of the entire SSC2 300. Contamination or failure of the pump/flow control system 308 does not compromise the entire SSC2 300. The subsystem of the pump flow control system 308 can be easily removed for servicing or disposal and the SSC2 300 can be restarted with a replacement subsystem 308.

G. Controller Alarm, Start and Stop

The SSC2 300 controller can be programmed to start, stop, or alarm on any input variable or variables. This feature includes weather station data as well as instrumentation input values. Additionally, the SSC2 300 can be programmed to start or stop upon user request via the controller front panel start and stop buttons or remotely through modem control. The alarm circuit 88 can enunciate locally, remotely via cables or remotely via the modem. All parameters are set through the setup program.

H. Other System Attributes

Data from the data modules, which may be the CCMs 14,' weather station 310, or global positioning system 312, can be simultaneously retrieved through the use of a custom Windows based application. The data modules are interconnected through their respective Bendix style connectors. The host computer 13 used to retrieve the data records sequentially requests a single record from each data module. After all records have been retrieved, the user has a chronological file listing all attributes of the acquired sample. This file is accessible through Microsoft Excel or through any text editor.

The host PC 13 is used to configure data modules as required. In certain controller operating modes, different controller flow rates and data sampling rates may be used for different CCMs 14.' The CCM 14' can record process variables to be used for specific run sequences and report these values to the control unit 12' for use with the specified CCM 14.' It is also possible to program other data modules, such as the weather station 310 or global positioning system 312, to operate as standalone units. Using the same Windows based program, the user can specify the number of records to record and the frequency at which to record the data. The data module can then be interfaced directly to its respective operating device for data acquisition.

I. Specifications

In the preferred embodiment, the SSC2 300 has a 2.8 l pm, double diaphragm pump with 0–2 l pm flow control and has a 40–50 l pm contrifugal blower pump with 0–100 l pm flow control. The SSC2 300 has a real-time clock with an accuracy of 1 sec/month and a non-volatile PCMCIA solid state storage device. The SSC2 300 has four independent instrumentation channels, each channel configurable as 0–5 volt or 4–20 mA input which allows for the configuration of process instrumentation signals such as flow, temperature, or pressure or for the connection of real-time contaminant monitoring probes, such as carbon monoxide detectors or radon detectors. The SSC2 300 has both consecutive serial data acquisition and concurrent serial data acquisition capabilities. The SSC2 300 can receive data from a portable weather station 310, such as rain, temperature, wind speed, wind chill, and direction, from a global positioning system 312, such as latitude, longitude, current track, speed, date, and time, from CCMs 14', such as date, time, controller flow rate, process, instrumentation data, logging, active collection chamber, and error codes, and from an additional serial data acquisition channel. The SSC2 300 also has similar concurrent serial data acquisition capabilities.

The SSC2 300 has other enhanced capabilities. For instance, with regard to sampling frequency selection, the SSC2 300 has a user defined interval from 1 minute to 99 hours and 59 minutes in 1 minute intervals, random time interval, and non-uniform time intervals in elapsed minutes or clock time. With regard to operating modes, the SSC2 300 can begin or end acquisition based on any combination of the following parameters: event driven—such as process instrumentation notification and weather station event notification; remote modem request—such as via the controller at 14.4 Kbits/s; or time or volume—such as samples acquired for a specified time duration or for a specified total flow volume. With regard to alarm modes, the SSC2 300 can enunciate an alarm via modem or locally based on any combination of the following parameters: instrumentation setpoints, including weather station and GPS values, controller malfunction/discontinuance of operation, or loss of power. With regard to data retrieval, data can be retrieved through a host computer 13 serial connection or modem, either real-time or at the completion of a run cycle. The resultant file is a chronological listing of all attributes of the acquired sample. The file is accessible through any text editor. With regard to controller software, separate Microsoft Windows based applications are utilized for data retrieval and controller setup. The controller setup is accomplished via the controller PCMCIA disk drive either through a host computer PCMCIA adapter or a serial communication link. The SSC2 300 also has other support software, such as Global Positioning software in any NMEA format and weather station software which may download weather data daily, weekly, or monthly.

J. Removable Flow System

Due to accuracy limitations on flow controllers 44, it is difficult to obtain a flow controller 44 that will operate over the entire flow range the SSC2 300 may be required to use, such as from 0.5 Liters per minute to 50 Liters per minute. The SSC2 300 advantageously can quickly exchange flow controller assemblies 44 with minimum operator interface.

Figure 8:
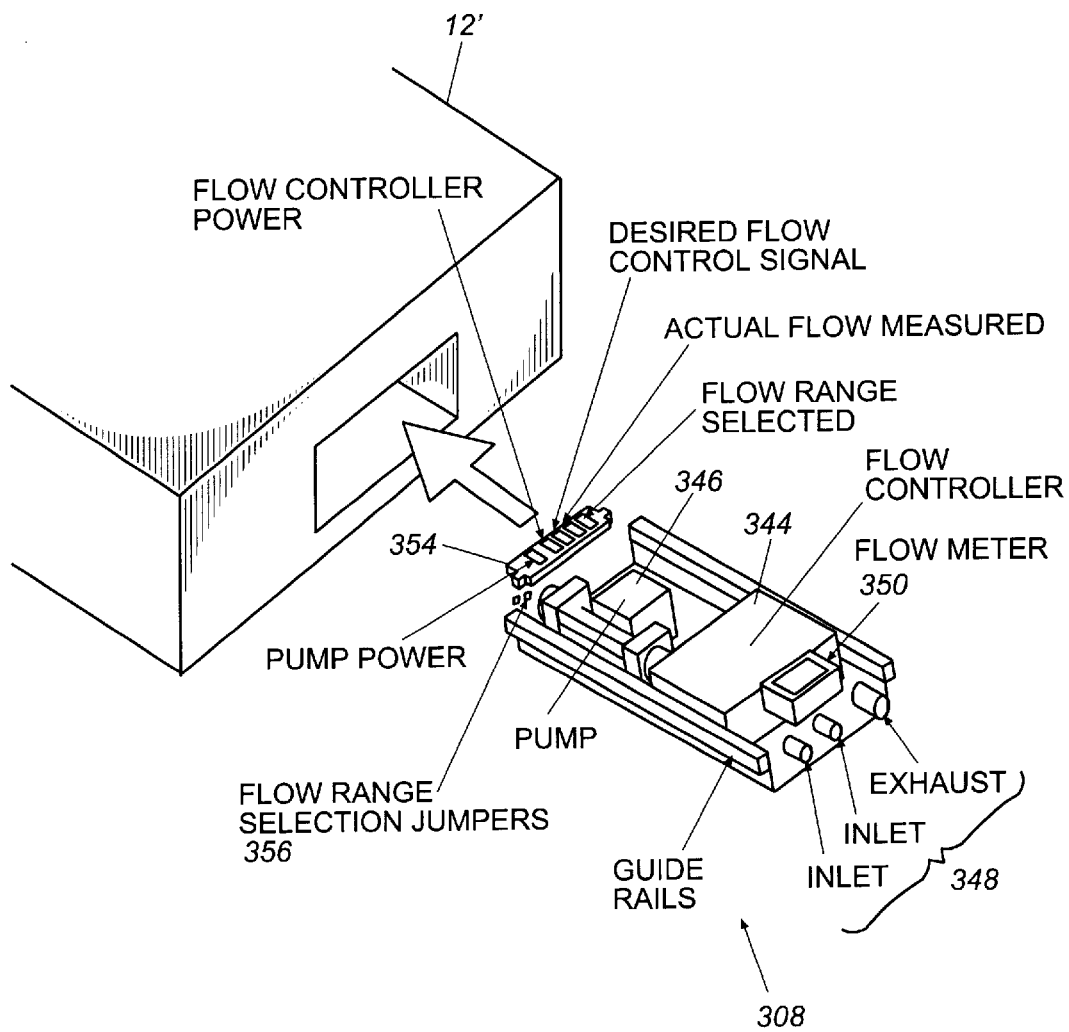
FIG. 8 is a diagram of a removable flow assembly for use with the sampling system of FIG. 7.

With reference to FIG. 8, a removable flow system 308 is comprised of a flow controller 344, a pump 346, the inlet and exhaust piping 348, and a flow meter 350 mounted on a rigid frame. The end of the frame terminates with a edge finger type electrical connector 354, similar to those found on PC based computer cards. The electrical connector feeds power to the pump 346 and flow controller 344, control and data signals to the flow controller 344, and a jumper 356 selectable "signature" for the specific card.

During process sampling operations at flow ranges from 0.5 to 2.0 Liters per minute, the SSC2 300 reads a desired flow rate and data sampling rate from the active CCM 14' at startup. If the CCM 14' contains invalid rates, the SSC2 300 reverts to default values stored in the SSC2 300. During emergency response operations at flows in the range of 50 Liters per minute, the SSC2 300 reads the digital signature associated with the removable flow system 308 and adjusts its operating parameters, such as run duration, data sampling rate, and flow rate, to predefined values stored in the SSC2 300. The use of predefined emergency response controller values eliminates the need for the operator to reprogram an available CCM 14' to the emergency response values or to have spare CCMs 14' available dedicated to emergency response activities.

The use of a card edge connector 354, wing nuts, and self contained piping 348 significantly reduces the change out time of the flow system 308 for the operator. The operator need only remove the wing nuts, slide the current flow system 308 out of the SSC2 300, insert the new flow system 308, and resecure the wing nuts. Piping connections to the external CCMs 14' and the process exhaust are make through Swagelok Quick Connect type couplings. The SSC2 300 can be equipped for process flow rates at 0.5 to 2.0 Liters of flow to one equipped for emergency response at 50 Liters per minute flow rate in less than five minutes.

III. SSC3

A. Overview

Figure 9:
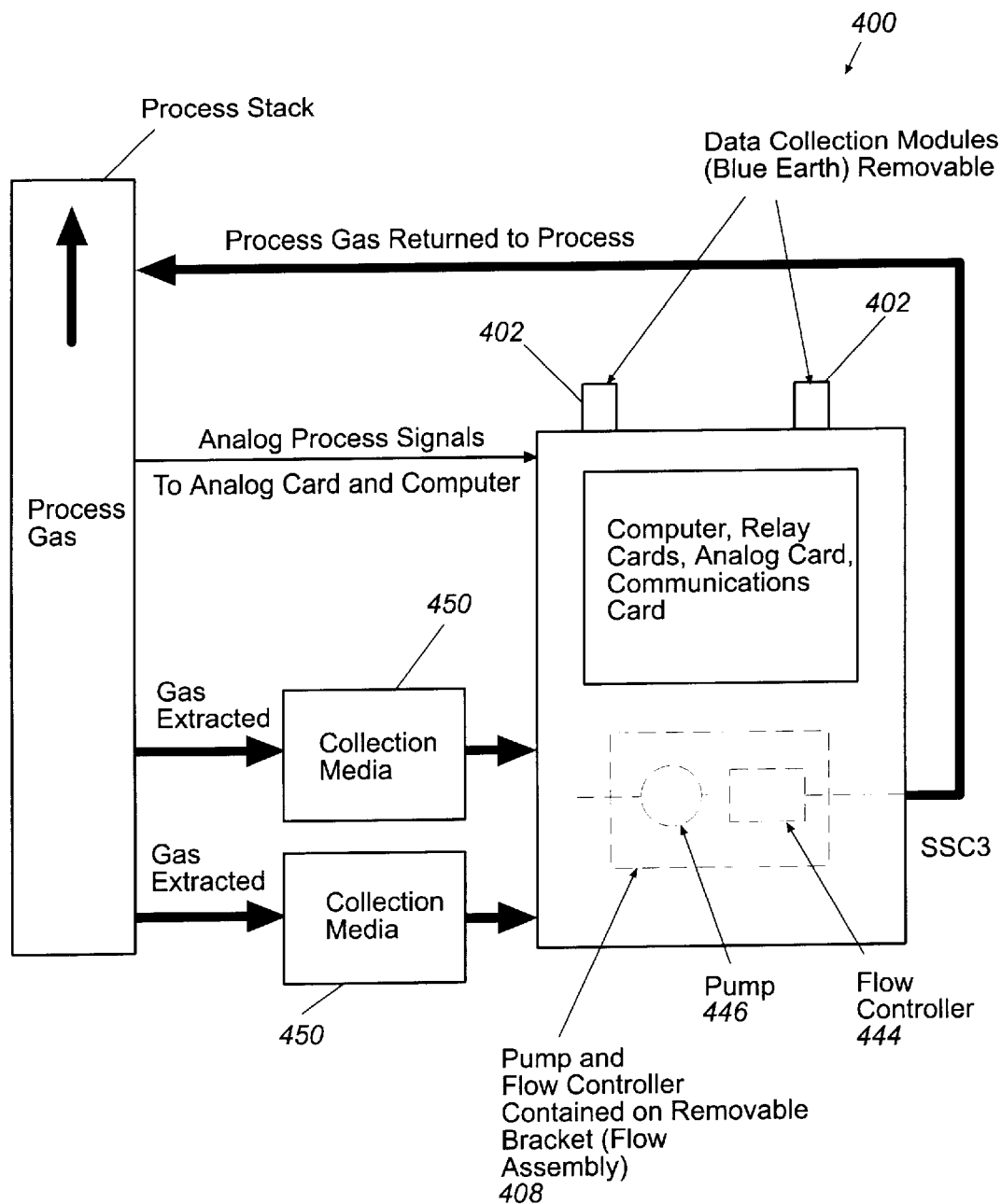
FIG. 9 is a diagram of an application of a sampling system according to a third embodiment of the invention.
Figure 10A:
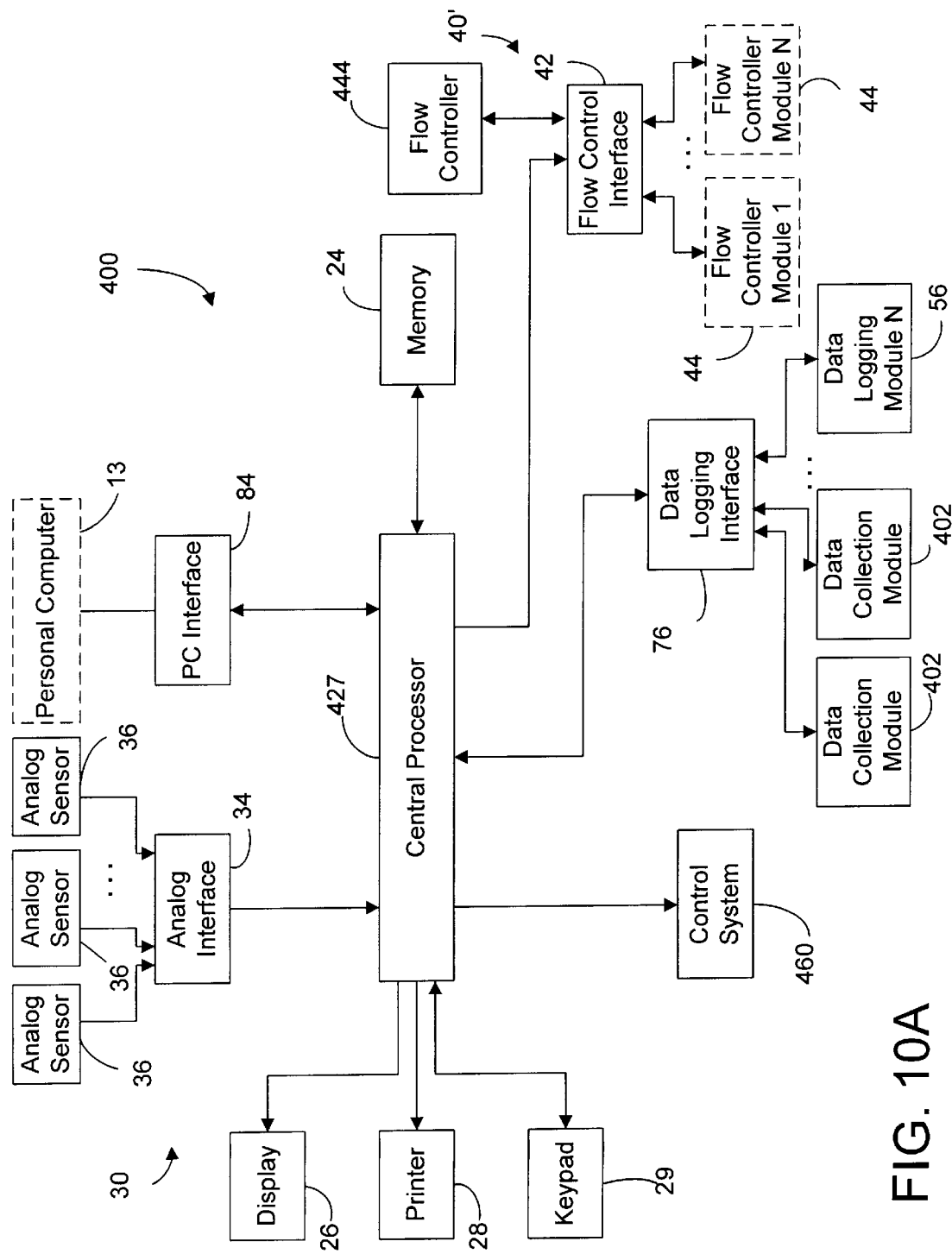
FIGS. 10A and 10B are block diagrams of the sampling system of FIG. 9.
Figure 10B:
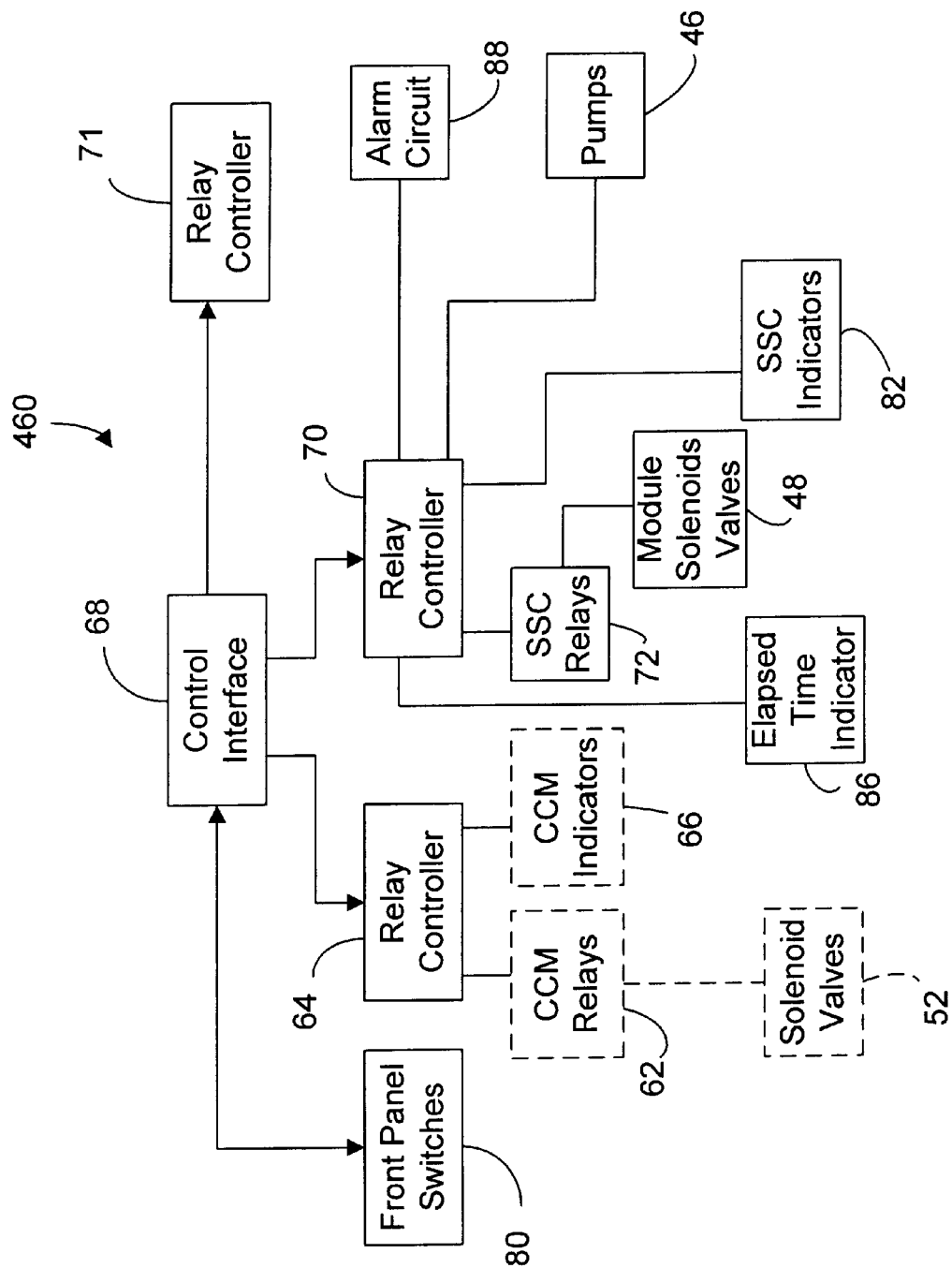
Figure 11A:
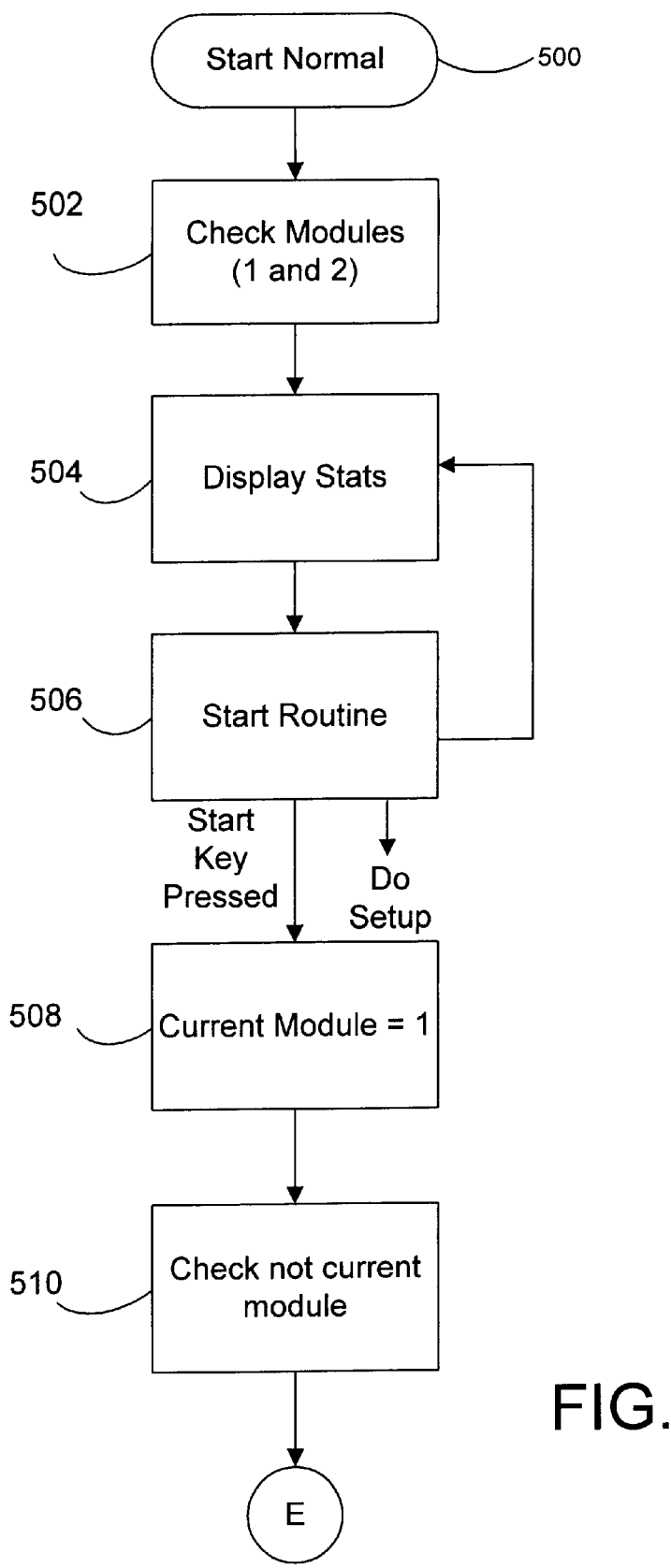
FIGS. 11A to 11E are flow charts illustrating a main processing loop of the sampling system of FIG. 10.
Figure 11B:
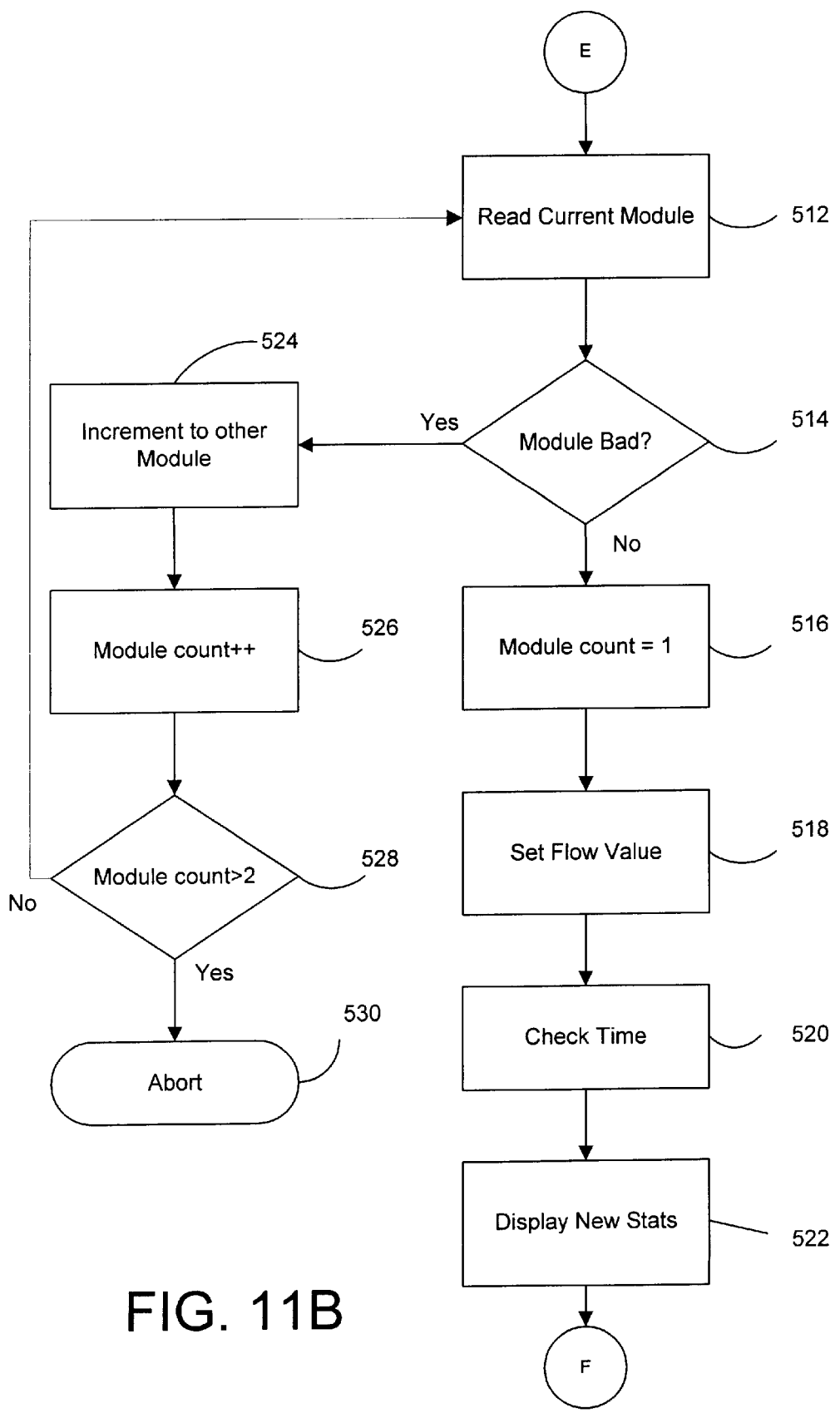
Figure 11C:
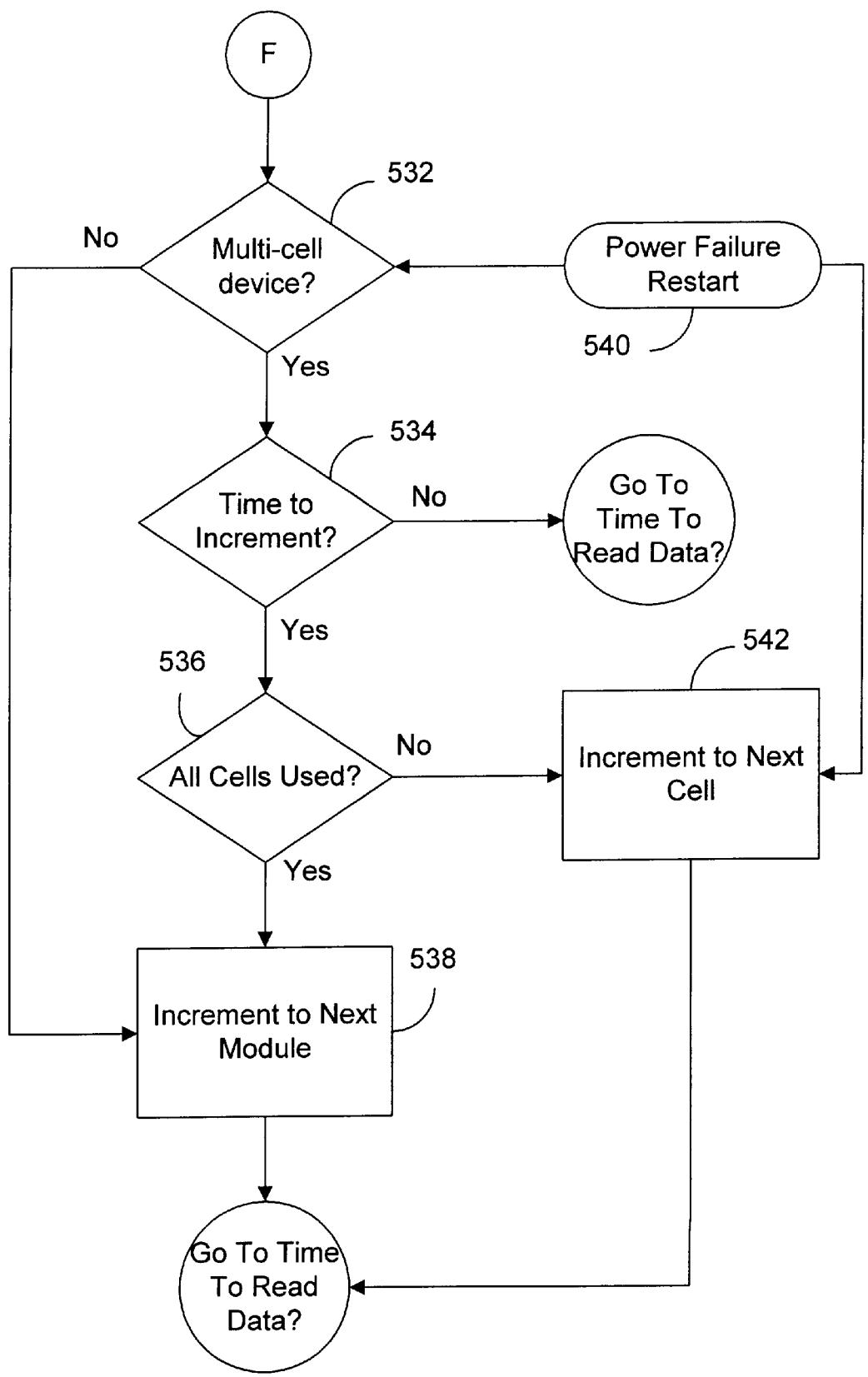
Figure 11D:
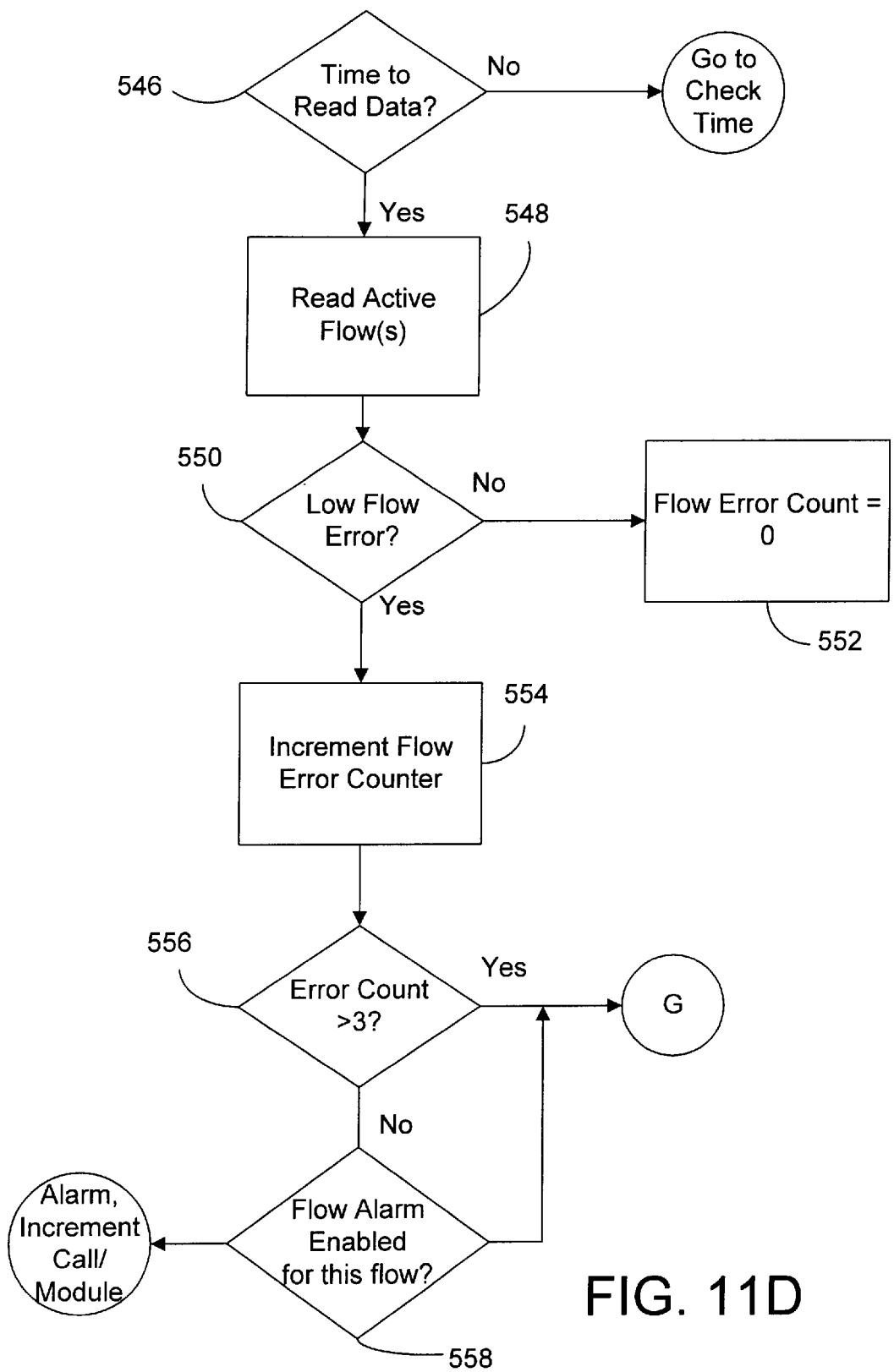
Figure 11E:
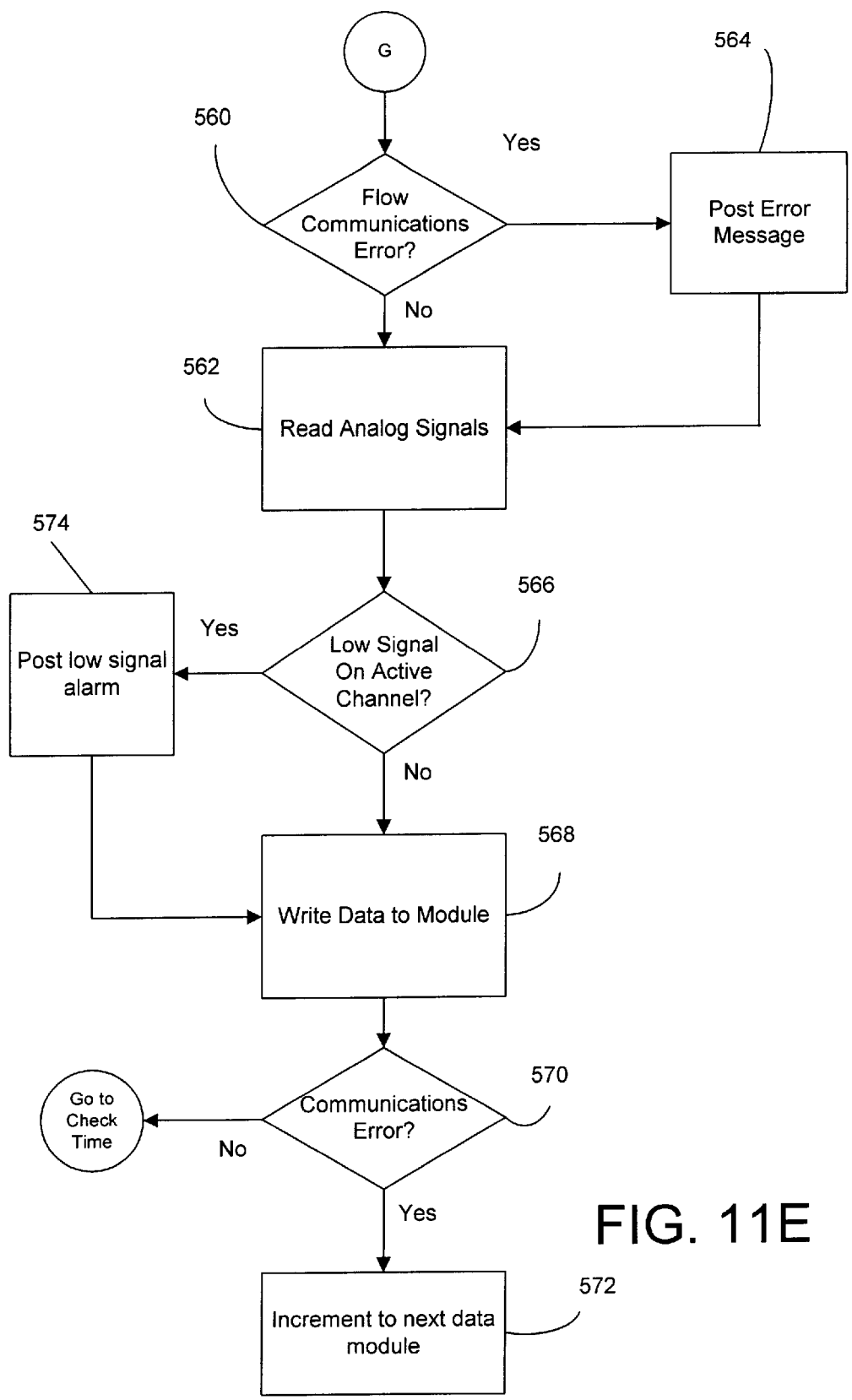
Figure 12A:
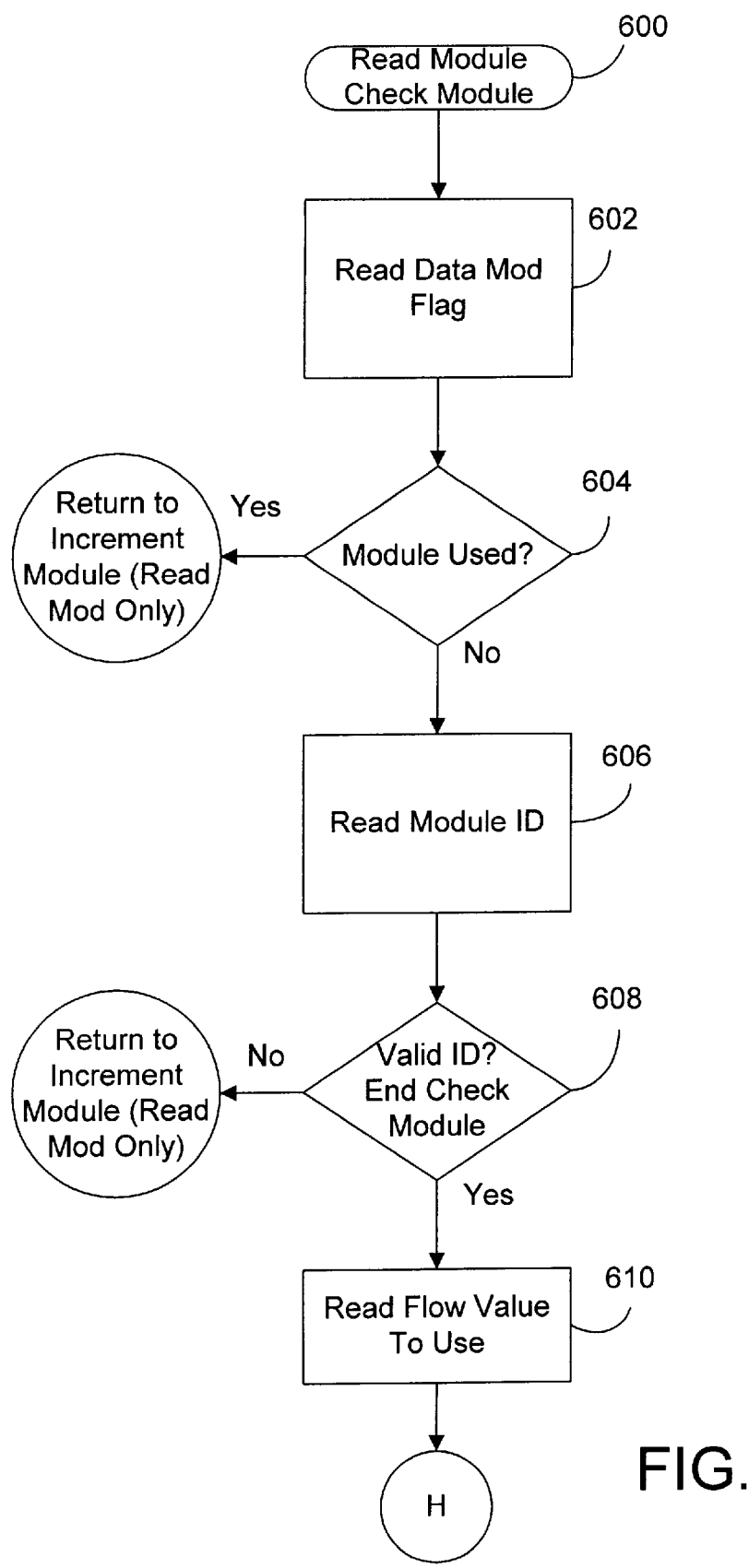
FIGS. 12A and 12B are flow charts depicting read routine processing for the sampling system of FIG. 10.
Figure 12B:
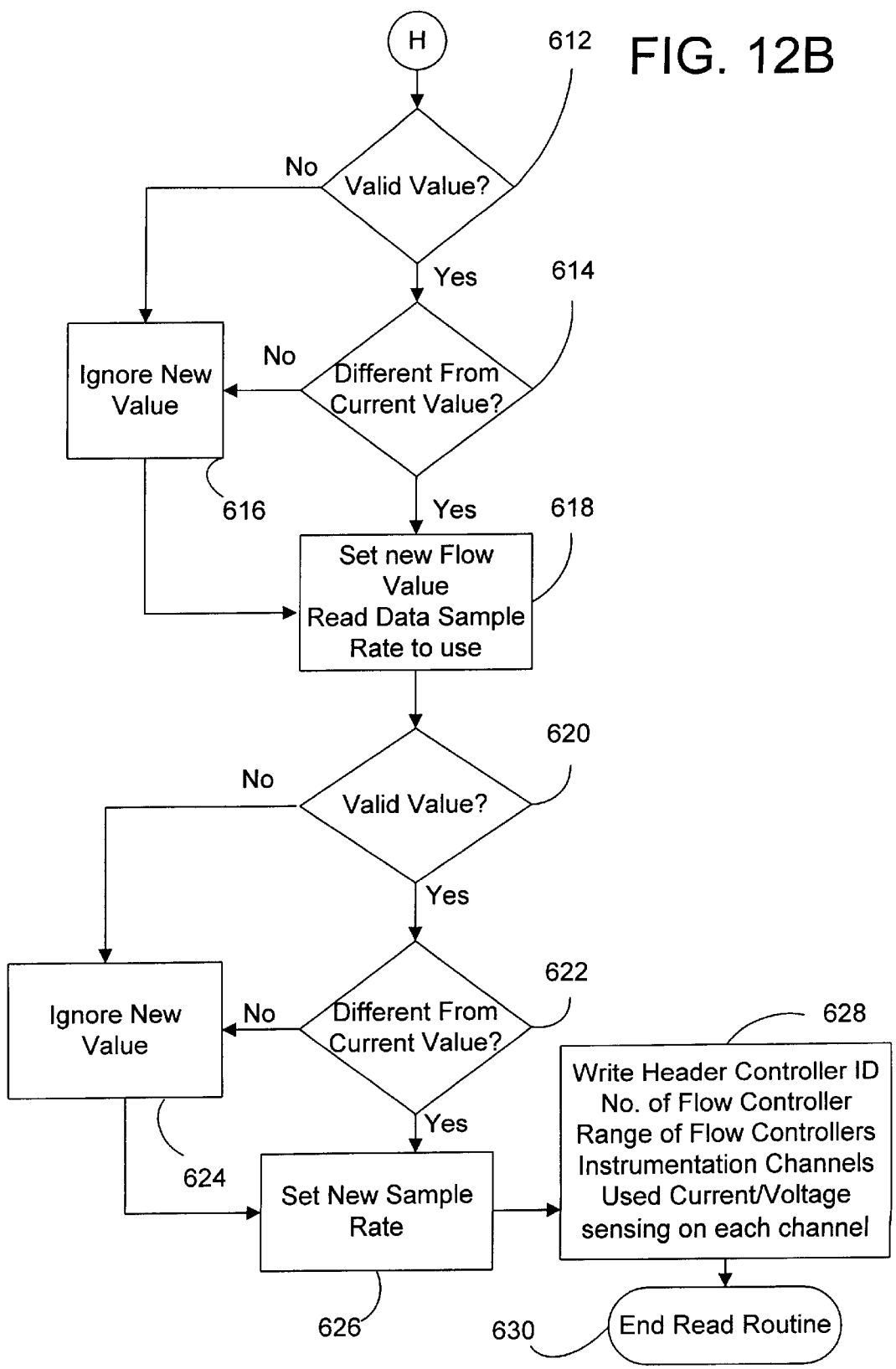
Figure 13A:
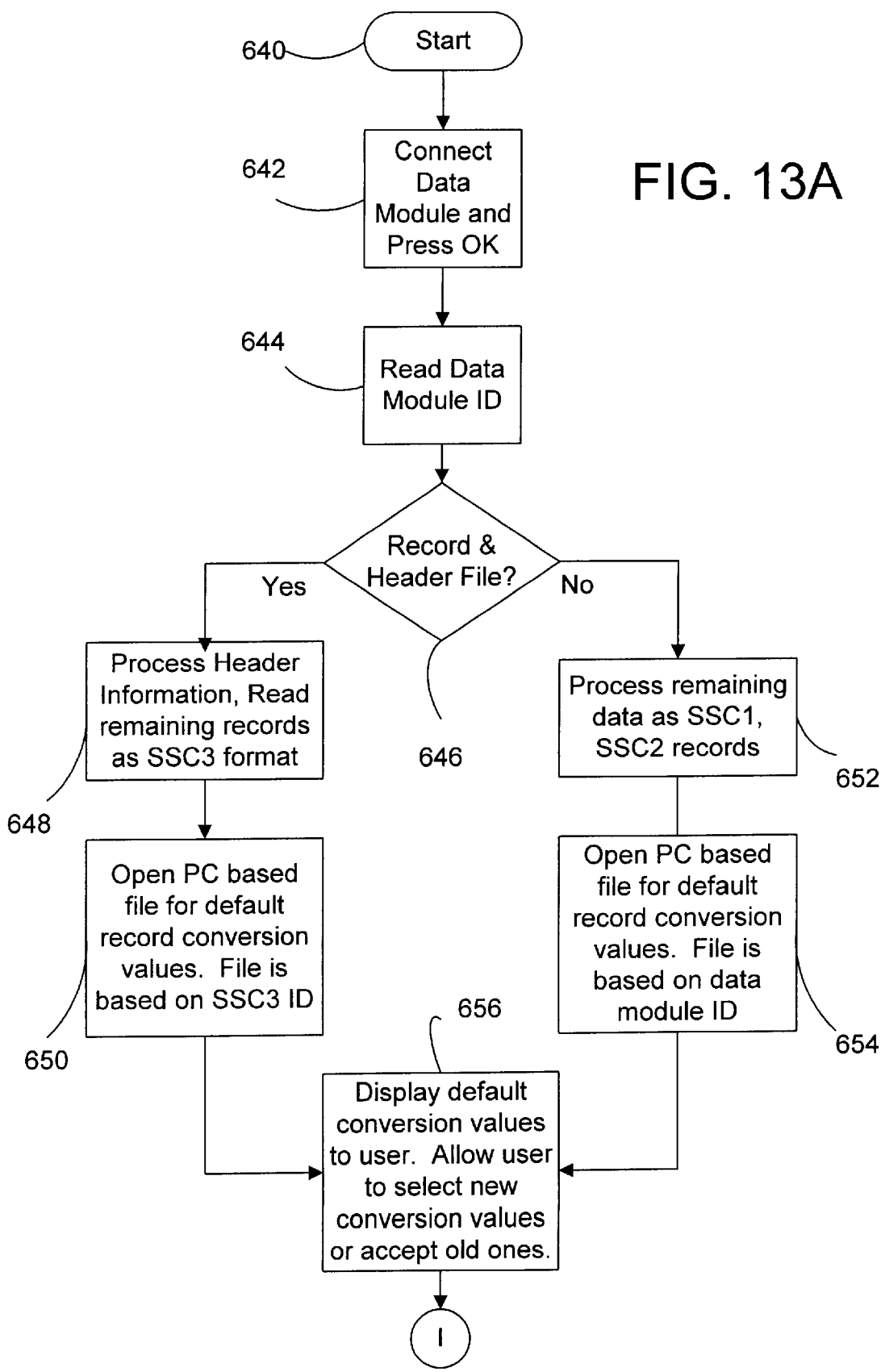
FIGS. 13A and 13B are flow charts depicting a CCM read routine.
Figure 13B:
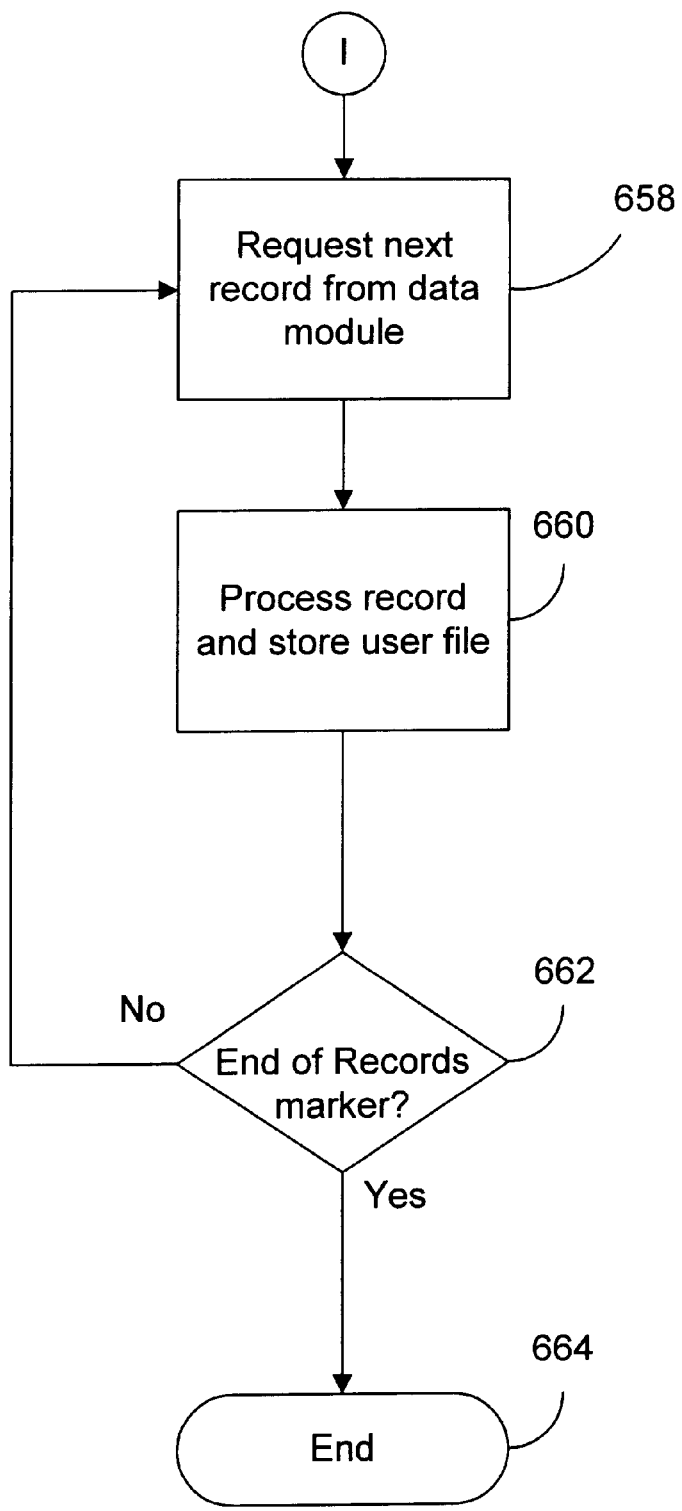
Figure 14A:
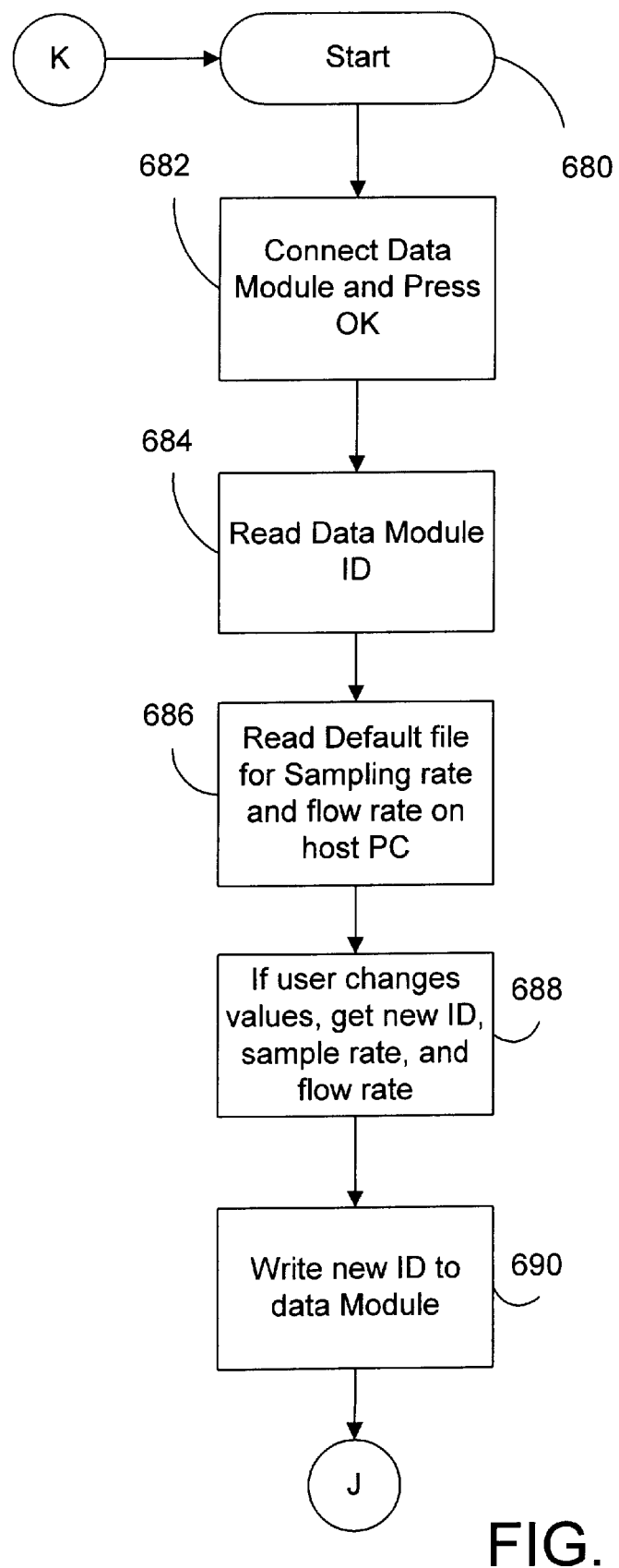
FIGS. 14A and 14B are flow charts depicting a CCM set routine.
Figure 14B:
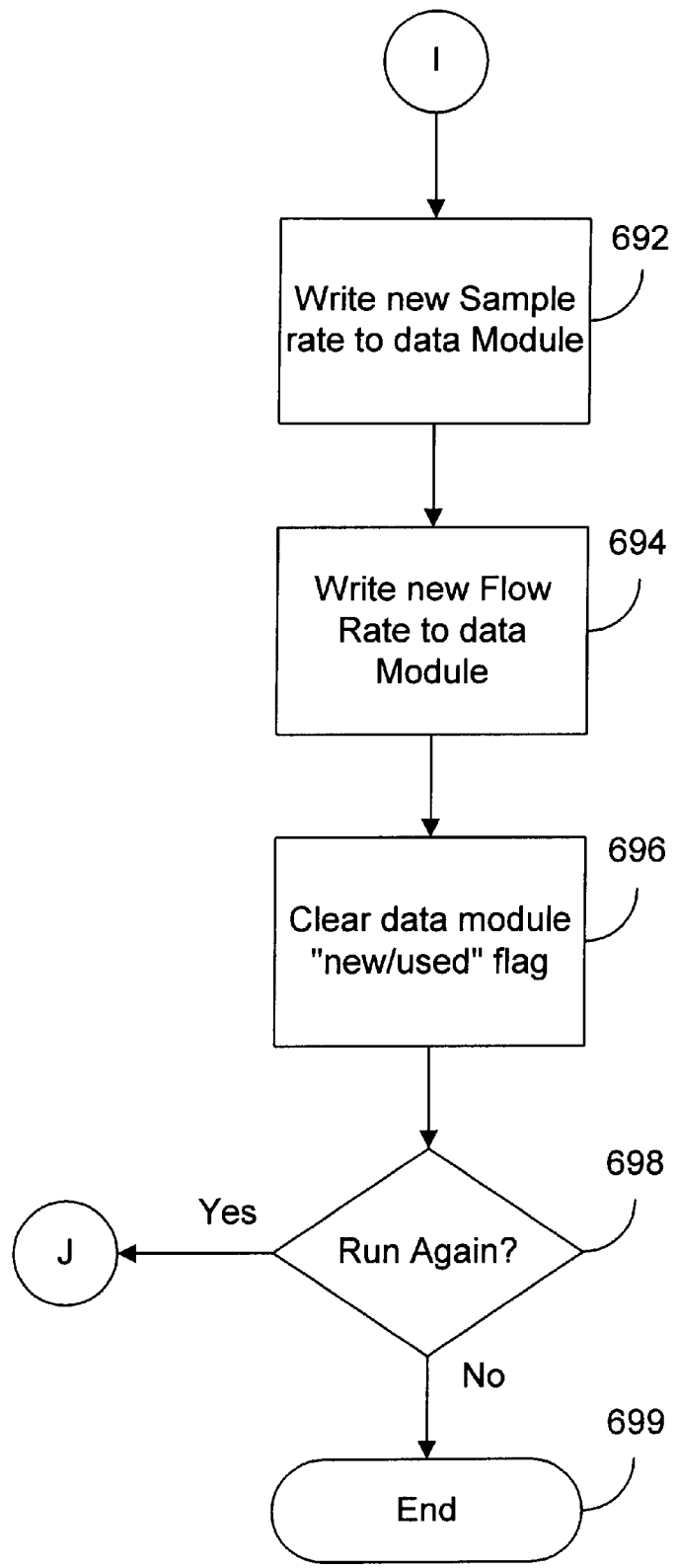
Figure 15:
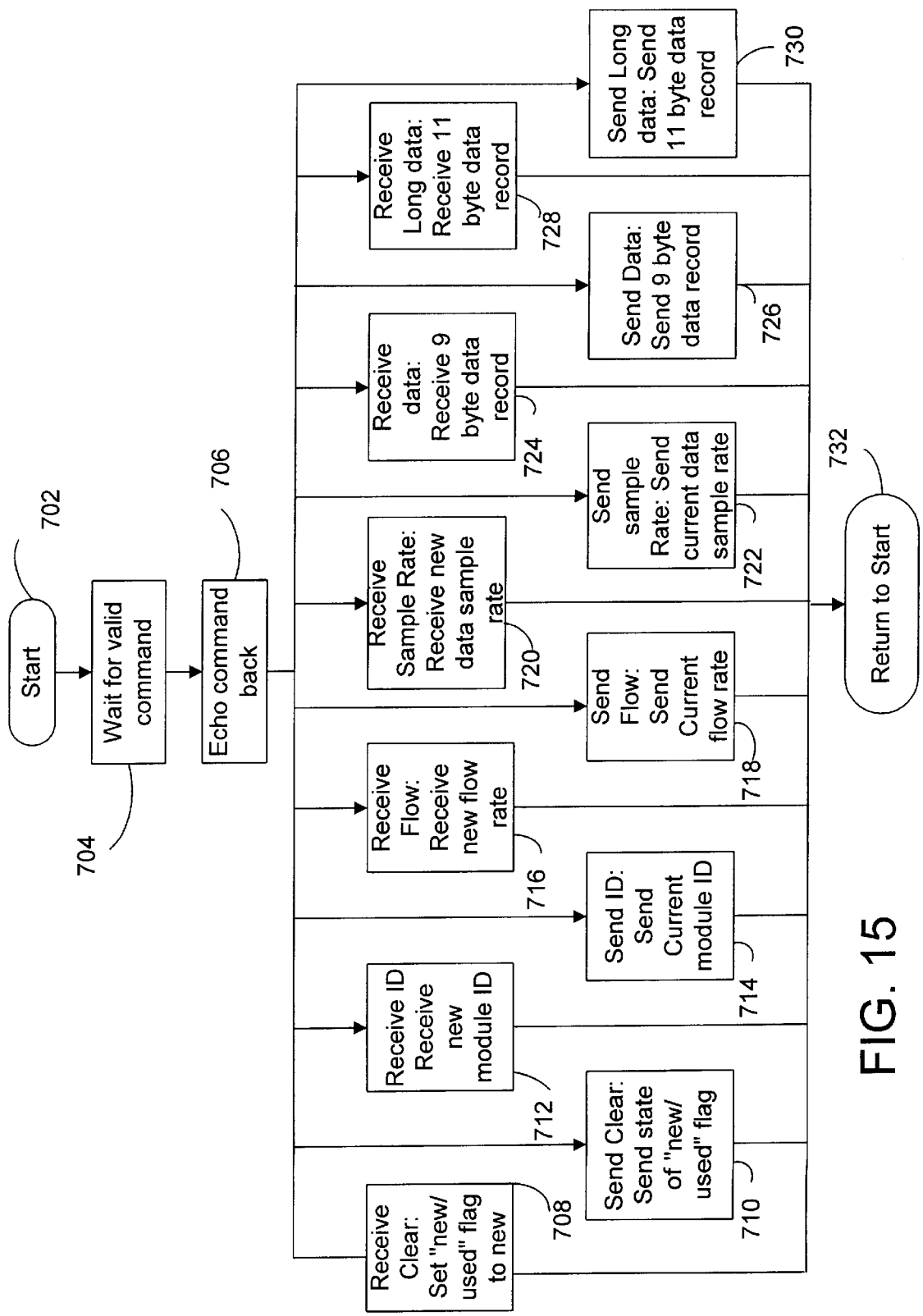
FIG. 15 is a flow chart of a data logging module routine.

With reference to FIGS. 9 and 10, a Sampling System Controller according to a third embodiment (SSC3) 400 aids in the collection and analysis of air borne particulates. The SSC3 400 aids sample collection and analysis by performing the following functions: gas extraction through sample collection media at a regulated rate, periodic logging of pertinent sample collection data to an onboard data collection device, and automatic cycling of same type sample collection media.

The SSC3 400 has a built in mass flow controller 444 and double diaphragm pump 446. The pump 446 and flow controller 444 are mounted on a removable bracket to facilitate exchange for repairs or different operating ranges. The operating range is determined by the range of the mass flow controller 444 installed, by the air extraction capabilities of the pump 446, and the operating pressure of the system being sampled. Two data collection modules 402 are installed on the SSC3 400. One of the two modules 402 is active at any given time, corresponding to the active sample collection media, and is used to record pertinent data. The active data collection module 402 also reports the desired flow rate for the SSC3 mass flow controller 444 to the SSC3 400. The user sets the desired flow rate by attaching a data collection module 402 to a host computer 13 and running the Windows based program "Data Module Setup." The mass flow controller rate may be adjusted each time a new data collection module 402 is activated on the SSC3 400.

The SSC3 400 has power and communications ports to allow the connection of one or more SSC3 Auxiliary Flow Systems (SSC3 AFS) 450. The AFS 450 provides up to three independent sample streams for additional sample collection media. The sample streams are controlled indepently of each other allowing for concurrent and/or sequential operation of the sample streams. In other words, the SSC3 400 may have sample streams operated in parallel with each other with the streams sampling the same or different fluid flows for the same or different material of interest. The AFS 450 includes up to three flow controller assemblies, each assembly with a pump and mass flow controller. Presently the AFS 450 consists of two auxiliary flow systems. The operating range of the two AFS flow assemblies 450 is determined by their respective pump and mass flow controller arrangement. The AFS 450 is connected to the SSC3 400 by two cables, one for power and one for communication signal. The operator specifies the desired flow value for each AFS flow assembly 450 through a setup menu on the SSC3 400. Unlike the flow assembly 408 internal to the SSC3 400, the AFS flow systems 450 do not receive desired flow information from the active SSC3 400 data collection module. The AFS flow assemblies 450 may be equipped with automatic cycling ports to cycle between primary and backup collection media. The cycle time for the AFS sample media are the same as the cycle time specified for the primary sample device installed on the SSC3 400.

Actual flow values are periodically read from all active flow assemblies, both in the SSC3 400 and in the AFS 450. Theses values are recorded to the active data collection module 402 on the SSC3 400 and are monitored for low flow conditions. A low flow condition is declared if three successive readings are less than 80% of the desired value. If this occurs, the alarm contacts are closed on the SSC3 400 and an error message is displayed on the SSC3 400 for the affected flow assembly. If the SSC3 400 is configured to take action on a flow assembly that is registering a low flow value, the SSC3 400 will attempt to reestablish flow after a low flow has been detected. The low flow action is configured by the user through the SSC3 setup menu via the SSC3 keypad 29 and display 26, which will be described in further detail below.

The SSC3 400 records, at programmable intervals, pertinent sampling information to an attached data collection module 402. Each entry consists of the day of the month, hour, minute, flow rates for each active flow assembly, any instrumentation signals being recorded, and error codes. The data recording rate is set by the operator by connecting the data collection module 402 to a host computer 13 and running the program "Data Module Setup." Each data collection module 402 can retain up to 1680 records and the data rate can vary between 20 seconds and 1 hour. The SSC3 400 can operate up to four flow assemblies 450 or receive up to three instrumentation signals or a combination of both. The SSC3 data collection module 402 storage space is divided such that the flow controller measurements and instrumentation data occupy the same space and are mutually exclusive. In other words the data collection module 402 can record up to four different items, such as flow or instrumentation. Table 1 below shows the space allocation of a data collection module 402.

TABLE 1

| Sample Data Record | | | | | | | |
| --- | --- | --- | --- | --- | --- | --- | --- |
| Day of Month | Hour | Minute | Flow 1 Value | Flow 2 Value or Instrument 1 | Flow 3 Value or Instrument 2 | Flow 4 Value or Instrument 4 | Error Codes |

The data records stored in the data collection module 402 are retained through a lithium battery internal to the data collection module 402. Once information has been stored on the device 402, a central processor 427, under normal operating conditions, will not reuse the data collection module 402 until all information has been retrieved via a host computer 13 by the Windows based program "Module Download" and the program "Module Set" has been executed to reset the internal data flag. Alternatively, the SSC3 keypad 29 can be used to reset a connected data collection module data flag. If this option is chosen, all data previously stored in the device 402 is lost.

The SSC3 central processor 427 has two ports to allow the connection of primary and backup sample media. Solenoids 48 in the control system 460 alternate between the primary and backup sample collection ports on a user defined frequency. The dual ports allow the user to run continuous sampling operation uninterrupted by changing out the used or inactive sample collection media and associated data collection module 402 while the alternate port is operating. Additionally, the SSC3 400 has connections to allow the operation of multicell collection devices such as a Canister Collection Module (CCM) 14 or other custom device. The CCM 14, as described above, includes seven independent cells, each cell cycled into the air stream via a dedicated solenoid valve 52. The SSC3 400 can accept up to two CCMs 14 which are cycled on a user-defined frequency. Other multicell devices may be installed on the SSC3 400. The user, via the Setup menu, specifies the number of consecutive cells in the device with a preferred range of 2 to 7 cells.

The AFS flow assemblies 450 are currently fabricated as two types. The first type contains one inlet and one exhaust port. This type of flow assembly 450 is used in applications where it is not necessary, or desirable, to cycle between two inlet ports or two sample collection media. The second type of AFS flow assembly 450 contains two inlet ports with dedicated solenoid valves 52. The cycle rate of the inlet ports on the AFS flow assembly 450 is the same as the cycle time specified for the inlet ports on the SSC3 central processor 427.

B. Setup

Figure 16:
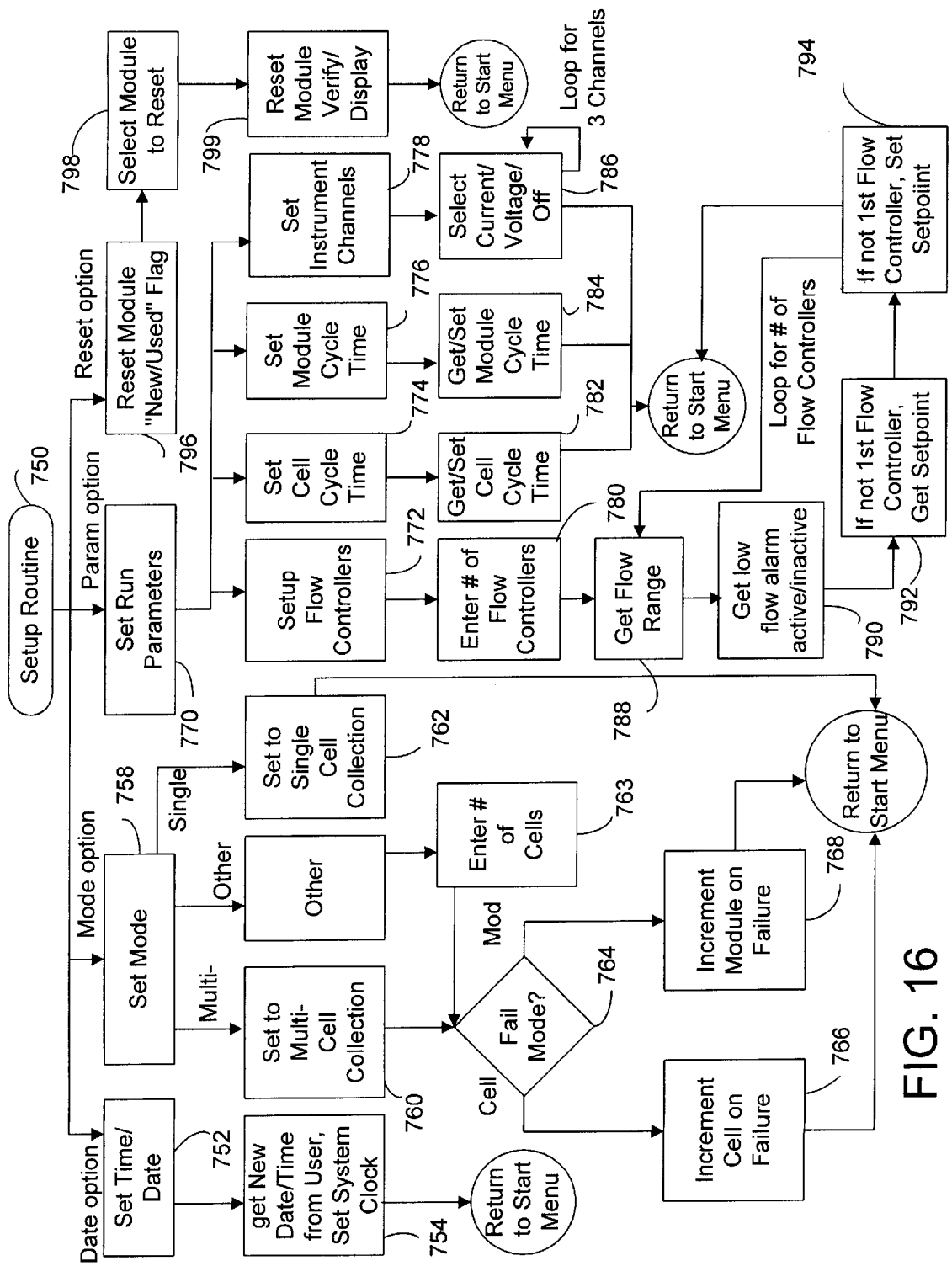
FIG. 16 is a setup routine for the sampling system of FIG. 10.

With reference to FIG. 16, the "SETUP" option is a tiered menu with additional submenus. One submenu under the "SETUP" option is: "FLOW PARAMS," "OPERATING PARAMS," "INSTRUMENTS," and "RESET MOD." The "FLOW PARAMS" option at step 772 requests the user to specify the number of flow assemblies 408 to be used at step 780, the operating range for each assembly 408 at step 788, the error recovery of each assembly 408 at step 790, and the desired value for flow assemblies in the AFS 450. The central processor 427 calculates the desired flow rate as the ratio of the desired flow to the operating range for a given assembly. Because of this, it is possible and even desirable to scale the operating range and desired flow values for maximum accuracy due to round off errors in the SSC3 400. For maximum accuracy, the entered values should be greater than 0.5 but less than 50. Each flow assembly 408 or 450 can have the error recovery feature active or inactive. If the error recovery feature is active for a given flow assembly, then the central processor 427 will automatically cycle to the backup sample collection media in the event a low flow condition is detected on that assembly 408 or 450.

The "INSTRUMENTS" option at step 778 under the "SETUP" menu allows at step 786 each available instrumentation channel to be turned off or selected to monitor current, 4 to 20 milliamps, or voltage, 0 to 5 Volts. As described above, some flow assemblies and instrumentation channels in the analog system 30 occupy the same space on the data collection module 402. Instrumentation channels that are not available due to overlap with the flow assemblies are not displayed in the "INSTRUMENTATION" menu. Jumpers corresponding to individual current or voltage measurements must be inserted or removed on the analog interface 34 inside the SSC3 400.

The "RESET MOD" option at step 796 under the "SETUP" menu at step 750 allows the data flag to be reset on either of the two data collection modules 402 connected to the SSC3 400 at step 799. After the desired module has been selected, the data flag is reset and verified. If the flag does not reset on the first try, attempt to reset the flag two more times. If the flag still does not reset, the module 402 should be returned for repairs or replacement.

The "OPERATING PARAMS" option at step 770 under the "SETUP" menu contains the following options: "MODE," "CELL TIME," "MODULE TIME." The "MODE" option at step 758 selects the option to operate the central processor 427 in a multicell collection mode at step 760, single cell mode at step 762, or "other" at step 761. The "other" mode allows the user to specify the number of cells in a custom multicell device, preferably a valid range of 2 to 7 cells. In practice, the central processor 427 automatically accepts the outputs of the Kaman connectors even in the single cell operating mode. However, if a multicell operating mode is selected, the device will revert to the next cell in a loss of flow recovery condition or in a loss of power recovery condition. Therefore, the selection of the operating mode should be determined by the desired recovery action to be taken in a loss of flow or a loss of power.

The "CELL TIME" option at step 774 under the "OPERATING PARAMS" submenu allows the user to specify at step 784 the amount of time each cell in a multicell device will be exposed to the air stream. The SSC3 400 is designed to cycle through all available cells in a multicell device at the user defined cycle rate and then switch to the next canister or collection device 402. If the device is being operated in a single cell collection mode, the cell time should be set to ⅐ the module time or greater.

The "MODULE TIME" option at step 776 under the "OPERATING PARAMS" submenu allows the user to specify at step 784 the amount of time each single cell collection device is exposed to the air stream. If the SSC3 400 is operating in a multicell mode, the module time should be set to 7 times the cell cycle time or greater.

C. Sampling

During operation, a red LED indicator of the active data collection module will be illuminated. This indicator also indicates the active sampling tubes on the SSC3 flow assembly and the AFS flow assemblies 450 with multiple ports. An elapsed time meter 86 on the SSC3 400 indicates the elapsed time in hours and one one-hundredth of an hour that the present sample collection media has been operating. The elapsed time indicator will automatically reset to zero when the cell or module cycles. The time remaining for the active cell and or module are shown on the SSC3 display 26. The meters above the elapsed time indicator show the relative intensity of any connected instrumentation signals (0 to 100%). This same information is shown on the SSC3 display 26.

The SSC3 display 26 rotates through a series of messages as the central processor 427 operates. Information displayed includes: current date and time, active module, flow rates, desired flow rates, system configuration, instrumentation values (0 to 100%), remaining time on the active cell and or module, and errors. The error field is reset when the SSC3 keypad 29 "C" key is pressed.

D. Hardware

The SSC3 400 is based on a Motorola eight bit embedded central processor 427. The central processor 427 is preferably a New Micros NMIX-0020 version containing a Motorola 68HC11A8 variation processor. The PC or Data Module interface 84 comprises a New Micros NMIL-5002 dual serial communication card, the control system 460 includes three New Micros NMIL-7022 relay cards, and the analog interface 34 comprises a New Micro NMIL-4004-4 12 bit 4 channel analog card.

The central processor 427 contains both RS232 and RS485 serial driver chips dedicated to a common serial channel. The jumper used to select the communication 485 or 232 has been replaced by a connector with wires routing over to a toggle switch on the interconnect board. The 232 serial mode is used to communicate with the SSC3 400 for maintenance activities via an external laptop computer 13. The 485 mode is used during operation to communicate with attached flow controllers. In the 232 serial mode, the host computer 13 can download special maintenance code to the central processor 427 for various activities including: setting/verifying flow controller addresses, calibrating analog instrumentation channels, and resetting erroneous operating parameters on the central processor 427. Additionally, special run code can be loaded into the central processor 427 to allow tailored operation for special sampling needs. In the 485 mode, the central processor 427 automatically executes the main sampling program. The 485 serial driver can communicate with up to four flow controllers through a single chip, such as in a daisy chain operation.

The data module interface 76 includes two independent RS232 communication channels. Each channel is dedicated to one of the data collection modules 402 connected to the SSC3 400. Transmit and receive lines are preferably the only communications lines used between the interface 76 and data modules 402. Additional data collection devices may be used for expanded operations. Additional data sets that may be desired include the following: weather station information, GPS information, Krypton monitoring. The limited storage space of the current data collection modules do not allow for the storage of expanded information sets. However, it is possible to connect more than one data module per channel and allow each module to acquire different, but synchronized, data sets.

The control system 460 includes three relay controllers with one relay controller operating the solenoids 52 associated with a first CCM 14, the second relay controller operating the solenoids 52 associated with the second CCM 14, and the third relay controller 71 responsible for all other relay driven outputs. The third relay controller 71 is responsible for such functions as alarm output contact closure, pump operation, sample 1 and sample 2 solenoid operation, and elapsed timer start/stop and reset. The third relay controller 71 also controls the two solenoids 48 designed to switch between primary and backup single cell collection devices. In the event of an alarm condition, the third relay controller 71 closes to provide an alarm circuit current path. The SSC3 400 preferably does not posses an annunciation device but is connected to a device in the facility.

The analog interface 34 includes a New Micros NMIL-4004-4 4 channel, 12 bit analog-to-digital converter for receiving analog signals from the three instrumentation signal inputs. The analog interface 34 provides an RC lowpass filter for each channel to reduce high frequency noise that may be present in the signal. Associated with each instrument channel on the analog interface 34 is a voltage/current selection jumper. Due to the RC network, the instrument signal levels are slightly lower than the actual signals present at the instrument input jacks. The most effective method of compensating for this is to adjust the slope and offset parameters in the host download program "Module Download."

In the preferred embodiment, the display 26 is an LCD display 26, such as AND model 721 ST, having a 4 line by 20 character display with backlighting. The keypad 29 is a Grayhill model 86JB2-203 4 row by 5 column keypad. The pump 446 is a Brailsford model TD-4X2 double diaphragm 24 Volt DC pump which can sustain greater than a 5 Liters per minute flow rate in ambient conditions. Other pumps can be substituted for greater flow rates or for liquid media if desired. The flow controller 444 is a Sierra model 860-L-2-OV1-SV1-V1-S1 with a 0.020 orifice, air media, 15 PSIG inlet and 12 PSIG outlet pressures. Four different flow ranges have been successfully tested in the SSC3 controller 444: 0–200 ml per minute, 0–500 ml per minute, 0–2.0 Liter per minute, and 0–5.0 Liter per minute. The data collection module 402 used in the current design is a Blue Earth model BE-01. The data collection module 402 contains an RS232 serial port, battery backed memory, and a Basic operating system. Data storage on the Blue Earth 402 is limited to approximately 32 Kbytes, although an expansion module is available that will increase the memory size to approximately 1 Mbyte.

E. Main Operation

With reference to FIGS. 11A to 11D, the central processor 427 begins operation by enabling the interrupts and clearing the LCD display 26. Next the central processor 427 checks the status of the watch dog flag. The watch dog flag is set if the central processor 427 terminated abnormally during its last operation, such as from loss of power.

If the flag is clear, the central processor 427 checks and displays the status of the two data modules at step 502, displays the current controller operating parameters at step 504, and enters the main menu at step 506. The main menu allows the user to view the operator selectable parameters of the controller, set the operating parameters, or start the controller operation. If the user selects the 'start' option, the initial state of the third relay controller 71 is set, the state of the second data module CCM 14 is checked, and the first Blue Earth data module 402 is activated. In the event the first data module 402 is unusable, the central processor 427 automatically reverts to the second data module 402. The function, "check_time," is called with a one in the first parameter to initialize the counter for the next data read cycle. The data read cycle is the frequency at which the central processor 427 stores flow and analog data to the active Blue Earth data module 402.

If the watch dog flag "wd_flag" is set, it indicates an abnormal restart condition, such as loss of power. An error message is displayed, "Abnormal Restart," and the 'COPF' bit of the misc_flag is set. The misc_flag is a flag used to display error messages to the display 26 and is used to write error codes to the active Blue Earth controller 402. During a power failure restart at step 540, the state of both modules 402 are checked with the function "check_module." Next the data read cycle is initialized through the function "check_time" with a one passed in the first parameter. The "cell_on" flag determines if the power failure results in an increment to the next cell at step 542 for multicell sampling devices, or increments to the next sampling port and module at step 538. If the "cell_on" flag is set to one, the central processor 427 increments to the next cell at step 542 in a multicell device. If the "cell_on" is set to zero, the central processor 427 increments to the next collection port and module at step 538. The assumption behind the loss of power recovery routine is that the sample is removed from the process air stream during the power outage. If the sample collection device is reintroduced to the process air stream, there will be a discontinuity in the collected sample. This discontinuity is avoided by switching to the next cell in a multicell device or the next sample collection port in a single cell device.

After the central processor 427 has performed all initialization and executed the appropriate startup sequence, either power fail restart or normal start, the watch dog flag "wd_flag" is set to one. The "wd_flag" remains a one unless the central processor 427 exits program execution through an operator "Stop" request or the central processor 427 exhausts all available modules 402. The central processor 427 is now ready to enter the main sampling loop.

The main sampling loop is a continuous loop that terminates if one of the two following conditions are met: "Stop" key is pressed by the operator or all available modules 402 or sample ports are exhausted. In the main sampling loop, the central processor 427 checks the data cycle time ("check_time"), the module cycle time ("check_mod_time"), the cell cycle time ("check_cham"), and keypad inputs ("kphit"). The data cycle time function returns a one if it is time for the central processor 427 to write data to the active Blue Earth data module 402 and a zero if it is not time. If the central processor 427 needs to write data to the Blue Earth module 402, the central processor 427 first reads the average flow and instrumentation values from the data structure contained in the module "flowlib.c" through the function "rd_flows" at step 548. The function "rd_flows" returns a one if a flow failure has occurred that requires the central processor 427 to take action. If "rd_flows" returns one, the central processor 427 writes the data to the active Blue Earth data module 402 through the function "send_data" and increments to the next active collection cell or collection port depending upon the state of the "cell_on" flag. The function "rd_flows" returns a one if the following conditions are present: three consecutive data read cycles produce an average flow that is less than 80% of the desired flow and the "take low flow action" status flag is set for the affected flow controller 44. The assumption in the flow failure action is that a large particle may be blocking the air flow to the active cell or collection port, thus switching to the next available port will reestablish flow to the sample device.

If the "rd_flow" function returns a zero, the central processor 427 writes the collected data, along with error codes, time, date, and active cell to the active Blue Earth data module 402 via the function "send_data." The function "send_data" returns a zero if the data transfer was successful and a one if the data transfer was not successful. If the function "send_data" returns a one, the central processor 427 increments to the next sample port regardless of the state of the "cell on" flag as well as the next data collection module.

The functions "check_mod_time" and "check_cham" increment to the next module and cell respectively when their time counters expire or when the maximum number of records have been written to the data collection module.

The function "get_srate" is used to convert the data sample rate read from the Blue Earth data module 402 from a floating point number to an integer. The central processor 427 tracks data collection cycle time to the nearest 10 seconds. The number received by "get_srate" is a floating point number expressed in minutes and 1/100 minutes. The number is converted to an integer expressed to the nearest 10 seconds for use by the "check_time" function. The "get_srate" function is called by the "read_module" function in "serial.c." It is necessary to handle as much data as possible in integer form since floating point numbers increase the amount of memory required for storage and significantly decrease the program execution time. The resultant number calculated by "get_srate" is stored in the global variable, 'dtime.' The value to be converted by "get_srate" is passed to the function as an integer. The data collection sample time is stored in the Blue Earth data module 402 as a floating point number in order to maintain compatibility with the SSC 10.

The desired flow rate written to the flow controllers 44 used in the SSC3 400 is preferably a proportion of the desired flow to the maximum flow rate for a given controller 44. The maximum flow rate for any controller 44 is the decimal number 750. If the decimal number 375 were written to a flow controller, for instance, the flow would be regulated at ½ the maximum flow range of the flow controller 44. The function "scale flow" produces the decimal value written to each controller 44. The function is called by the central processor 427 with the desired flow and maximum flow values passed as parameters. The desired and maximum flows are often in Liters or milliliters but may be in any unit as long as the desired and maximum are of the same units for a specific controller 44. Based on the maximum range, the central processor 427 determines the multiplication factors that must be used in order to stay within the integer bounds in order not to have overflow and loss of data during the multiplication. Maximum accuracy is achieved when the desired and maximum flows are between 0.1 and 5.0. The desired and maximum flows should be scaled to stay within these bounds. An example of data that may be passed to this function: desired flow 1.0 Liters, maximum flow 2.0 Liters, flow setpoint returned by the function 375. The desired flow and maximum flow are passed to the "scale_flow" function as integers multiplied by 100.

The startup routine, "do_start," is called by the central processor 427 at startup to display the initial operator choices: start controller sampling, set controller operation parameters, display current controller configuration. If the operator elects to set operating parameters or view the current configuration, the function executes the desired action and returns to the initial operator choice menu. The function will return only when the start option is selected. If the setup option is selected, the function calls the setup routines in the module "setup.c." If the current status option is chosen, the central processor 427 calls the "dsp_data" function repetitively until all setup information is displayed. The "dsp_data" function will display run time data as well, but this data set is not called unless the central processor 427 is operating. The "dsp_data" function is contained in the "setup.c" module.

For multicell devices, it is necessary to cycle through each of the cells in the collection device on an operator defined cycle time. The function "increment_chamber" is called by the central processor 427 when it is necessary to cycle to the next cell in a collection device.

When the "increment_chamber" function is called by the central processor 427, the function cycles the reset pins on the elapsed time indicator via the third relay controller 71. If the active sample port is one, "increment_chamber" sets the cell solenoid bit indicated by the variable "cham_cnt" on the "CCM1" relay board and sets all bits on the "CCM2" relay board to zero. If the active sample port is two, the function sets the cell solenoid bit indicated by the variable "cham_cnt" on the "CCM2" relay board and sets all bits on the "CCM1" relay board to zero. If the variable "cham_cnt" exceeds the total number of cells defined for the multicell device (contained in the variable "cell_count"), then the "increment_chamber" calls the function to switch sample ports, "increment_module." Otherwise, the cell count variable, "cham_cnt," is incremented and the function returns.

The exit function, "do_exit" is called by the central processor 427 to terminate sampling operation. The "do_exit" function is called when the operator requests the sampler to stop operation or whenever a condition occurs that prevents continued operation, such as no modules available or unable to recover flow on a flow controller 44 with the flow failure action selected. The function receives a status parameter that indicates whether the alarm contacts should be closed or open with it being closed for abnormal termination and being open for normal termination. If the status parameter is set to a one, the third relay controller 71 is called with the request to close the alarm contacts. The remaining sequence of events is initiated regardless of the alarm status.

The "do_exit" function clears the power failure flag from the "misc_flag" error indicator and sets the "wd_flag" to zero to indicate the central processor 427 requested operations to be stopped. The pump 446, port solenoids 48, and elapsed timer 86 are placed in the OFF state. Messages are displayed indicating the operation has stopped and any error codes that have occurred. After the shut down sequence has been completed, the central processor 427 enters a hold state until the controller power has been cycled.

The data cycle time routine, "check_time" is used to track when the SSC3 440 should write data to the active Blue Earth data module 402. The function passes three parameters: new/old state, time left on active module, and time left on active cell. The new/old state parameter informs the function if it is being called for the first time after startup or is being called at some point in time during sampling operation. The module time left and cell time left parameters are not directly used by "check_time" but are passed in the call to "dsp_data" as parameters. The "check_time" returns 1 if it is time to write data to the Blue Earth data module 402, else it returns 0.

If the new/old state is set to "new," the routine sets the "oldtime" variable equal to the current tens of seconds read from the real time clock. The "oldtime" is used to track when 10 seconds or greater has expired on the real time clock since the last update. The "timecnt" variable tracks how may 10 second intervals has expired since the last data write.

If the new/old state is set to "old," the routine checks the "oldtime" value against the current 10 seconds read from the real time clock. If the value is different, the routine calculates the number of 10 seconds that has expired, increments the "timecat" variable by the number of 10 seconds that has expired, and sets the "oldtime" variable equal to the current 10 seconds. If the "timecnt" variable equals the "dtime" variable, the cycle time in tens of seconds equals or is greater than the number of tens of seconds elapsed, "timecnt" is decremented by "dtime" amount, and a one is returned. If "timecnt" does not equal "dtime," a value of zero is returned.

Independent of whether it is time to write data to the Blue Earth module 402 or not, the "check_time" routine calls "dsp_data" each time "check_time" is called, except when called with a "new" status. A static counter increments the data set to be displayed up to the last data set, number of data sets defined by the "RUNCOUNT" define. Once all sets of data have been displayed, the static counter is reset and the initial data set is displayed on the next call to "check_time."

The elapsed cell time for multicell devices is tracked with the function "check_cham." The function receives a new/used status flag parameter and returns the time remaining for the active cell. The new/used status flag is set to "new" upon initial startup of the central processor 427. The "new" status flag initializes the static and global counters used to track elapsed time since the last cell was cycled.

If "check_cham" is passed a "new" status flag, the function sets the elapsed time counter, "timecntc," to zero, sets the last read time counter, "oldtimec," equal to the current minutes as read from the real time clock, and returns the cell cycle time as the time remaining on the active cell.

If the "check_cham" is passed a "used" status flag, the function reads the real time clock minutes and checks the current minutes against the minutes stored in "oldtimec." If the times are equal, then less than one minute has transpired. The function calculates the difference between the cell cycle time, "cham_time" and the time expired on the active cell, "timecntc," and returns the difference as the time remaining on the active cell.

If the times are not equal, one minute has transpired since the last time the "check_cham" variable "oldtimec" was updated. The function increments the expired time counter "timecntc" and sets the old time variable, "oldtimec," equal to the current minutes in the real time clock. If the "timecntc" variable equals the cycle time of the cell, "cham_time," the function calls "increment_chamber" to increment to the next cell and zeros the elapsed cell time variable "timecntc."

The "check_cham" function tracks the cell time to the nearest minute. It is assumed in the routine that less than one minute will elapse between calls to the function, unlike "check_time." As a safety precaution, the module count is checked in the routine to prevent more than 1685 records being written to an active data module 402. The data module 402 has limited storage capacity and exceeding the limits of the data module 402 could result in the loss of all data stored on the active module 402.

The "read_module" routine in the "Serial.c" software module is used to both read operating SSC3 parameters from the active Blue Earth data module 402 and to check the status of an inactive data module 402. The function receives the "state" parameter to determine which action is being requested, with a state equaling one for an inactive module check and zero for an active module read. The "read module" function returns a zero if successful and a one if not successful.

In both the "read" state and "check" state, the "read_module" function requests and checks the state of the current Blue Earth data module 402. It is the responsibility of the calling function to ensure the correct module 402 is selected in the global "module" variable prior to calling "read_module." If the module state is "used", the function posts an operator message and returns to the calling function with a one. If the state is "new", the "read_module" function checks to see if the "state" parameter passed to it was a one for "check module" or a zero for "read module." If "read_module" was requested to check the current module, then the function displays a "module OK" message to the operator and returns with a zero.

If the "read_module" function was called with it's "state" variable set to zero, the function requests the Blue Earth data module ID. In the current version of the SSC3 400, the ID is stored but not used by the central processor 427. After the ID is read, the function requests data sample rate and the internal flow controller setpoint from the data module.

The data sample rate is the frequency at which the central processor 427 writes data to the active Blue Earth data module 402. The Blue Earth data module 402 stores this value as a floating point representation of minutes and 1/100 minutes. The function "get_srate" is called to convert the minutes number to an integer based number representing the sampling rate in tens of seconds. In addition to setting the data collection rate, the data sample rate is also used to determine the interrupt frequency at which analog and flow controller data points are read. On average, the analog and flow data points are read eleven times between Blue Earth data write cycles. This interrupt frequency is set by a call to the function "SetScanPeriod."

The internal flow controller desired flow rate is also retrieved from the Blue Earth data module 402 a floating point number. The desired flow and maximum flow for a given controller should be specified in like units. Once the "read_module" function receives the desired flow rate from the active Blue Earth data module 402, the functions "get_frate" and "scale_flow" are called by the central processor 427. The function "scale_flow" uses the desired flow read from the Blue Earth data module 402 and the maximum flow rate, specified by the user through the SSC3 keypad 29, to calculate the setpoint value sent to the internal flow controller. The new setpoint value for the internal flow controller, along with previously calculated setpoints for any auxiliary flow controllers, is sent to the flow controller unit through the functions "StopScan," "SetFlow," and "StartScan."

The last function called by the "read_module" function is the "send_header" call. The "send_header" function writes controller setup information to the Blue Earth data module 402. This information includes the following: SSC3 controller ID, number of flow controllers installed, flow ranges for each controller, instrumentation channel configurations. If "send_header" returns an error, the module failure flag is set in the error variable and the function returns a one to the calling routine.

The Blue Earth data module 402 has a set of commands that define its operating characteristics. All commands are two bytes long, the first command letter always specifies if the Blue Earth module 402 will be receiving data, first command letter 'R,' or sending data, first command letter 'S.' The Blue Earth module 402 echoes back each character as it receives it, both command and data, for flow control purposes. The current data set for the Blue Earth module 402 is listed below in Table 2.

TABLE 2

| COMMAND | DESCRIPTION | ACTION TAKEN |
|---|---|---|
| RC | Receive Clear Command | Reset 'new/used' flag to new state, reset memory storage pointer to start position |
| RI | Receive ID | Receive and store integer ID value that follows |
| RT | Receive Sample Rate | Receive and store floating point data sample rate value that follows |
| RF | Receive Desired Flow Rate | Receive and store floating point desired flow rate value that follows |
| RD | Receive Short Data Set | Receive 9 byte data record that follows and store in memory, then increment to next memory storage location |
| RL | Receive Long Data Set | Receive 11 byte data record that follows and store in memory, then increment to next memory storage location |
| SC | Send Clear Command | Send state of "new/used" flag |
| SI | Send ID | Retrieve and send integer ID value |
| ST | Send Sample Rate | Retrieve and send floating point data sample rate value that follows |
| SF | Send Desired Flow Rate | Retrieve and send floating point desired flow rate value |
| SD | Send Short Data Set | Retrieve and send 9 byte data record that follows and store in memory, then increment to next memory storage location |
| SL | Send Long Data Set | Retrieve and send 11 byte data record that follows and store in memory, then increment to next memory storage location |

The SSC3 400 operating parameters are written to the Blue Earth data module 402 prior to any data being recorded to the module 402 by the function "send_header." The information sent to the module includes the number of flow controllers, flow range for each controller, status of each instrumentation channel (on/off; current/voltage), and controller ID. This information is used by the download utility to format the data storage file and for operator information.

The SSC 10 only stored 9 byte data records whereas the SSC3 400 preferably stores 11 byte data records to the Blue Earth data module 402. The download utility preferably works with either the SSC 10 or SSC3 400. The "send_header" writes the first two stored files to the Blue Earth data module 402 as two 9 byte header files. The first header file differs from the 9 byte data file in that the first byte stored is the day of the month plus hex value 40. Since the day of the month is a range of 1 to 31, the download utility can check the first byte to see if the 9 byte record that follows is a header or data. If the first record is a header record, the download utility knows to expect a second header file, date plus hex 60, followed by 11 byte data records (RL) command.

The function issues an 'RD' command to the Blue Earth module 402 to inform it that the SSC3 400 will be sending 9 bytes of information for storage. The first byte of information sent to the Blue Earth module 402 is the day of the month plus hex 40 followed by the hour and minute the module 402 was first activated and the sample port activated. Next the instrument 'on/off' status is sent along with the number of flow controllers 44 active. The next two bytes are the flow range of the internal flow controller 44 sent as the integer value multiplied by 100. The seventh and eighth bytes are the flow controller range for the first external flow controller and the last byte of the first record is the voltage or current status of the instrumentation channel.

Prior to sending the second record, the function issues an 'RD' command to inform the Blue Earth module 402 a second 9 byte data record is about to be transmitted. The second record of the header file is sent with the day of the month plus hex 60. The second through 5 bytes are the flow ranges for the auxiliary flow controllers 2 and 3, sent as an integer value multiplied by 100. The voltage/current status for the three instrument channels is compressed into a single byte and transmitted as byte 6. Bytes 7 and 8 are the SSC3 controller ID. The ID is used by the download program to load key default download parameters, such as slope and offset for active instrumentation channels, labels for flow or instrumentation channels, and location identifier. A blank character is sent as the last byte to fill out the record.

For each byte transmitted by the "send_header" function, the actual transmit routine checks for an echo from the Blue Earth data module 402. If the echoed character is not the same as the transmitted character, the "send_header" function terminates and returns a one to the calling routine. If the function is successful, a zero is returned.

The "read_module" performs the dual function of reading a newly activated module 402 as well as checking the status of an inactive module 402. In order to check the inactive module 402, a routine is needed, "check_module," that temporarily swaps the active module number stored in the variable "module." The "check_module" saves the number of the active module, calls the "read_module" function with the inactive module set in the "module" variable and the state parameter of the "read_module" set to one. If the module 402 is not useable, the "check_module" posts a failure message to the operator. The "read_module" function posts a "module OK" message otherwise. After checking the module 402, the function restores the current active module 402 to the "module" variable and returns a zero. The return value from this function is not used by the calling function.

The active sample port and active data module 402 cycle at a time period specified by the operator through the SSC3 setup routines. The active port and data module 402 may also cycle due to flow failures, module communications failures, expiration of active cells on multicell devices, or expiration of the maximum number of records for the active module. The "increment_module" function is called by the central processor 427 for any condition where it is necessary to swap active sample ports and data modules.

The "increment_module" function receives no calling parameters and returns no value. If the function is unsuccessful, it directly calls the exit procedure. The function clears the elapsed time on the active module counter "tmecntm," sets the number of records written to the active module "mcount," and clears the current cell counter "chamcnt." The function sets the new active module number in the active module variable "module," closes the newly inactive sample port and opens the newly active sample port by a call to the third relay controller 71, "relay_bd1." Next, "increment_module" calls the "read_module" function to check the status of the new module 402, retrieve controller flow and data sample parameters, and write the header files. If the "read_module" function returns a failure, "increment_module" sets the "NO MODULE AVAILABLE" flag in the "misc_flag" register and requests an exit with the alarm active. If the "read_module" is successful, the chamber count is zeroed and a call to increment chamber is initiated to advance to the first cell in a multicell device.

At the expiration of the data cycle period, the SSC3 400 reads all active instrumentation and flow channels and writes the information, along with the current time and date, to the Blue Earth data module 402. Each Blue Earth data module 402 can receive up to 1680 records with each record being 11 bytes long. The function "send_data" is used to transmit individual 11 byte records to the Blue Earth data module 402.

"Send_data" issues the 'RL' command to the Blue Earth module 402 to inform it the SSC3 400 will be sending an 11 byte record. The day of the month is read from the real time clock and transmitted as the first byte of information. Similarly, the hour and minute are read and sent as the second and third bytes of data. The internal flow controller 444 value, data range of 0 to 750, is sent as three nibbles of an integer, the upper most nibble being occupied by the active cell number for multicell collection devices.

The SSC3 400 can operate with either single cell collection devices or multiple cell collection devices. The function "mode_params" allow the user to specify the operating mode of the SSC3 400. In practice, the central processor 427 always exercises the multiple cell relays and thus will cycle multiple cell devices even if se t in the single cell operating mode. However, the failure mode, recovery from loss of flow or loss of power, differs depending upon the mode setting. If the central processor 427 is set for single cell collection, the SSC3 400 will always increment to the next sample port and module 402 in the event of a loss of power or loss of flow. If the central processor 427 is set for multiple cell, the operator chooses the failure mode.

The "mode_params" function main menu allows the operator to select the controller operating mode from the following: multiple cell operating mode for the CCM 14, single cell collection device, or a multiple cell collection device with the operator specifying the number of collection cells. If the CCM operating mode is selected, the operator selects the failure mode as either failing to the next module or failing to the next cell. The single cell collection mode forces the SSC3 400 to always fail to the next collection port in the event of a power or flow failure. The custom multiple cell mode is just like the CCM mode except the user specifies the number of cells in the collection device.

The function "run_params" is used to set the number of flow controllers 44, the failure mode for the flow controller 44, the active flow controller ranges and desired flows except the internal flow controller, instrumentation states, module cycle time, and chamber cycle time.

The "set flow" option in the "run_params" function sets the number of flow controllers 44, the flow ranges, desired flow values, and flow failure mode. The routine first requests the number of flow controllers 44 that are active. If a number is entered that is out of range, the function aborts. If the number of flow controllers 44 entered is valid, the routine requests the flow range for the internal flow controller 444. For maximum accuracy, this value should be scaled to be between 0.01 and 6. Next, the routine requests if action should be taken for a loss of flow on the flow controller 44 being set up. A loss of flow action causes the central processor 427 to switch to the next cell or collection device, depending upon mode setup options, if three successive flow reading are less than 80% of the desired value for a flow controller with the flow failure flag active. The routine cycles through the remaining active flow controllers 44 requesting the same data, namely flow range and flow failure state. The auxiliary flow controllers 408 also require the desired flow values to be entered. As with the flow range, the desired flow rate should be scaled between 0.01 and 6.00. If invalid data is entered at any point in the routine, the routine returns. For the auxiliary flow controllers 408, the desired set points are calculated after the data is entered for each controller unit with a call to "scale_flow."

If the module time option is chosen in the "run_params" function, the operator is requested to enter the number of hours each sample port will be active. If no data is entered, the function returns and retains its old settings. If data is entered, the module cycle time is converted to minutes and stored in the global variable "motime."

If the cycle time option is chosen in the "run_parms" function, the operator is requested to enter the number of minutes each cell in the multicell device will be active. If no data is entered, the function returns and the old cycle time is retained. If new data is entered, the global variable "cham_time" is set equal to the chamber time entered.

If the instruments option is chosen in the "run_params" function, the operator selects the state of the three instrumentation input jacks. The display scrolls through each instrumentation channel displaying the following setup options: instrumentation channel off, instrumentation channel set for 0 to 5 Volts, instrumentation channel set for 4 to 20 milliamps. If the instrumentation channel is set to off, the instrumentation status variable for the current instrumentation channel is set to 0 and a message is posted to the operator informing them of the selection. If the instrumentation channel is set to voltage, the value is entered into the instrumentation status variable and the operator is instructed to remove the jumper corresponding to the channel on the instrumentation board. If the instrumentation channel is set to current, the value is entered into the instrumentation status variable and the operator is instructed to install the jumper.

The main controller menu, displayed during normal central processor 427 startup, has three options: start, setup, and display current statistics. The setup option calls the "do_setup" function in "Setup.c." The "do_setup" routine has sub menus layered underneath: run parameter and mode parameter menus, as well as top level menus for setting the real time clock and resetting an inactive data module flag.

The "do_setup" function displays the following options upon initial call: set time, set run parameters, set mode parameters, reset module. The function waits for a keypress and processes the keypress according to the appropriate selection. An invalid selection causes the function to return to the main controller menu immediately. Completion of the selected task also causes the function to return to the main menu. If the set time option is chosen, the setup routine calls the "set_time" function in "RTC.c." If the mode parameters option is chosen, the "mode_params" function is called in "Setup.c." If the run parameters setup option is chosen, the "run_params" function is called in "Setup.c." If the reset module option is chosen, the function "reset_mod" is called in "Setup.c."

IV. Service Module

A. Overview

Figure 17:
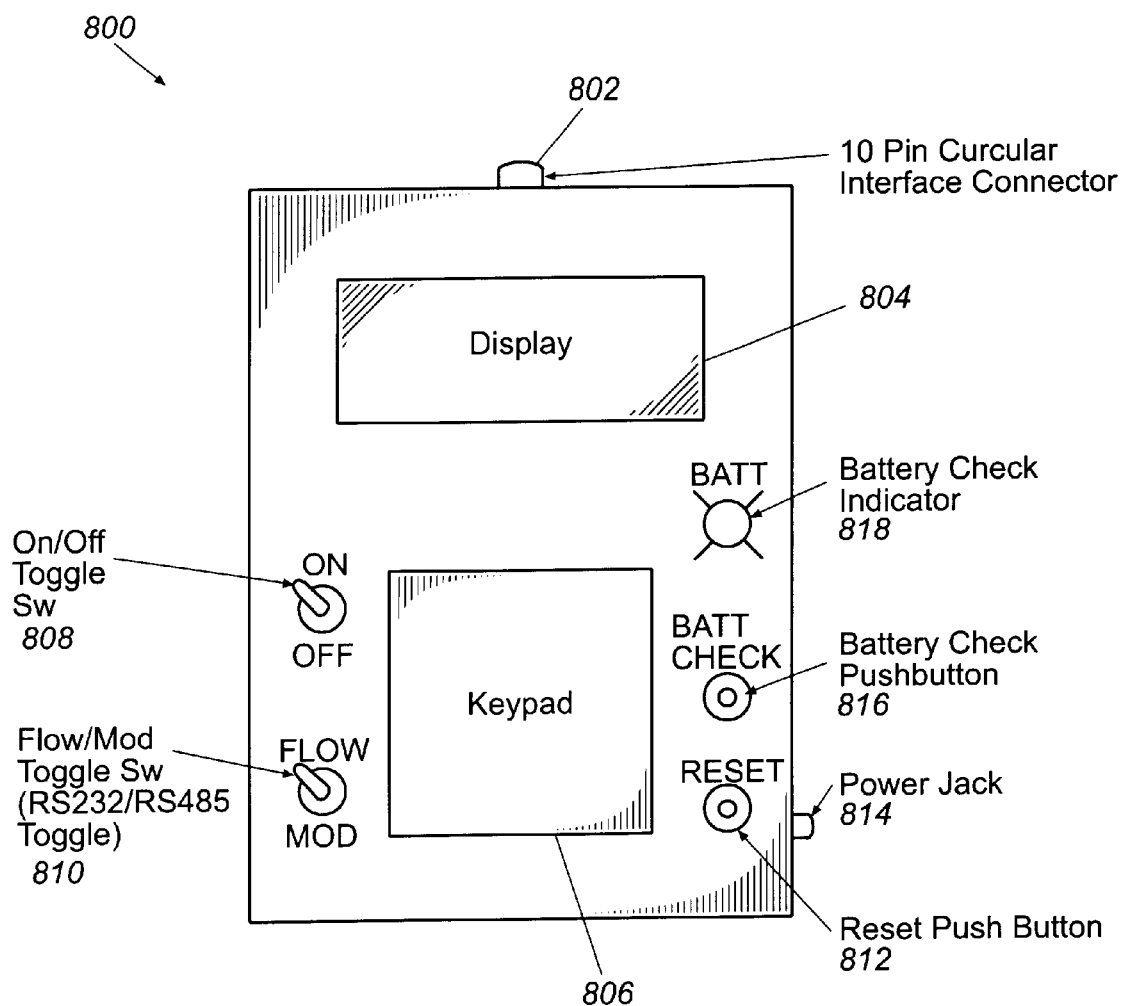
FIG. 17 is a front diagrammatic view of a service module according to a preferred embodiment of the invention.
Figure 18:
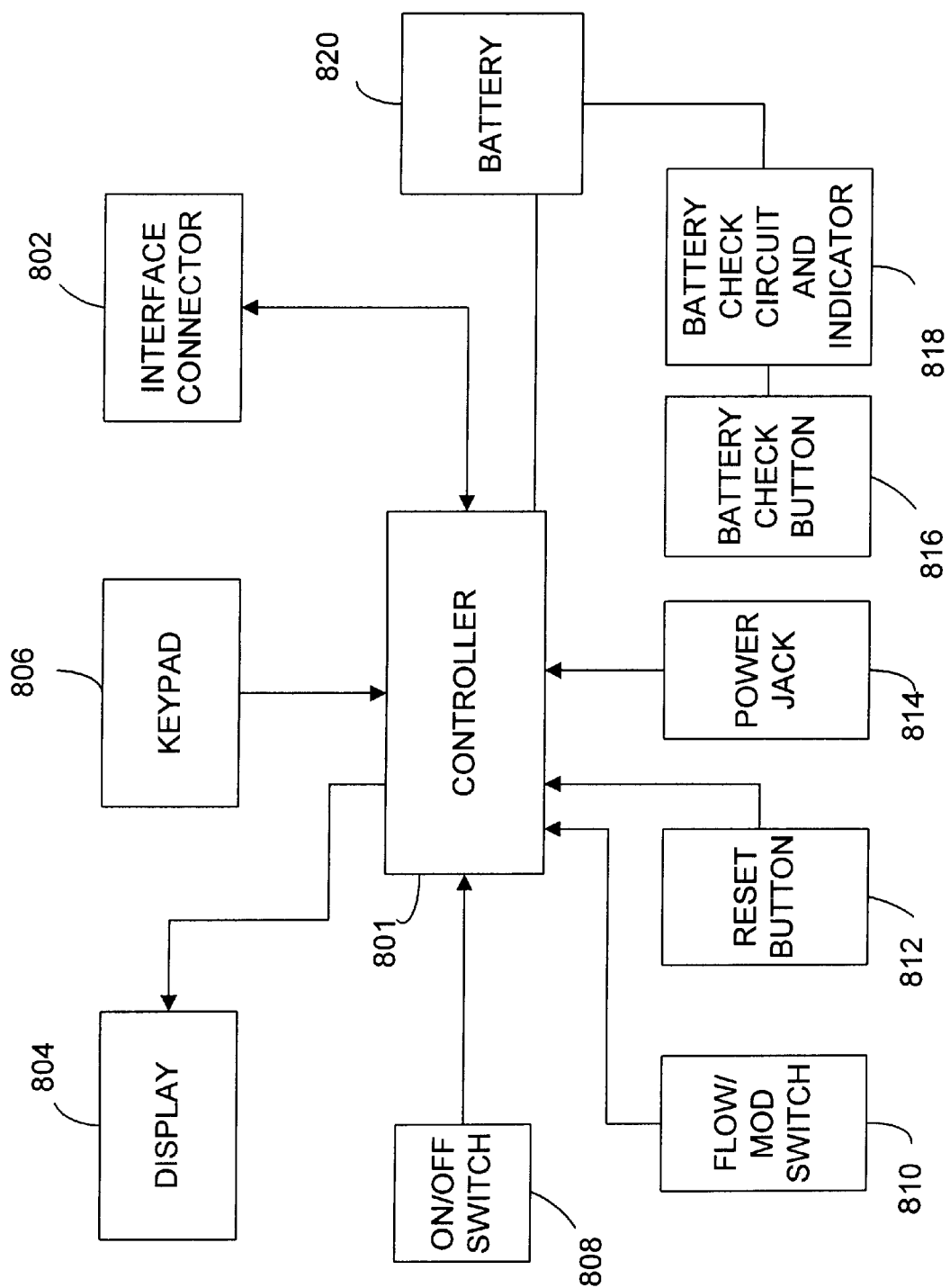
FIG. 18 is a block diagram of the service module of FIG. 17.

A service module 800 according to a preferred embodiment of the invention is shown in FIGS. 17 and 18. The service module 800 is a hand held device used to perform routine service activities to the SSC3 400 and related equipment. The actions the service module 800 performs include at least setting of the data collection module operating parameters, setting of the flow range value and units on flow controllers 444 or 44, setting the serial address of a flow controller 44 or 444, reading the flow range and unit of installed or uninstalled flow systems 408 or 450, and resetting default operating parameters on the SSC3 400.

B. Hardware

The service module 800 is comprised of a controller 801, interface 802, display 804, keypad 806, and on/off switch 808. The controller preferably comprises a New Micros NMIX0020, the display 804 preferably comprises a 4 line by 20 character display AND model 721-ST, and the keypad 806 preferably comprises a Grayhill 4 by 5 20 key keypad. The interface 802 allows an easy connection to the control unit 12' in the SSC3 400 and preferably comprises a 10 pin circular connector which interfaces to the various service cables required for each specific task. In addition to the display 804 and keypad 806, the face of the service module 800 contains a 'RESET' switch 812, a battery check button 816, a battery power indicator and circuit 818, and a mode switch 810 for selecting between RS485 and RS232 serial communications. The RS485 communications are preferred for flow controller communications while the RS232 is preferred for data module and SSC3 400 communications. The service module 800 can be powered from an external power supply through power jack 814, such as a wall mounted power supply 10 Volts DC output at 300 milliamps, or from an internal power source 820, such as two 9 Volt batteries.

C. Software

The service module 800, upon power up, displays three options for the operator to select: "Module Setup," "Flow Setup", and "SSC3 Setup." The "Module Setup" option allows the user to connect a data module 402 or 56 to the service module 800 through the interface connector 802 which may also provide power to the data module 402 or 56. Once the module 402 or 56 is connected, the operator can view the following information stored on the data module: module flag status (new or used), data recording rate, data module ID, desired flow value for the flow controller 444 contained in the SSC3 400. The operator may change any or all of the parameters stored on the data module 402 or 56. Each time a parameter is changed, the data module 402 or 56 is reread and the new information displayed to the operator. The service module "MOD" switch 810 must be in the "MOD" position for this operation.

If the user selects the "Flow Setup" option, the service module 800 must know if the flow controller is installed in the SSC3 444 or is an uninstalled unit 450. If the unit is installed, the operator must connect the service module 800 to the interface 84 in the SSC3 400 and prompt the service module 800 to turn the pump power to 'ON,' thus supplying power to any flow controllers 44 in the Auxiliary Flow System 450. Once this action has been performed, the service module 800 "MOD" switch 810 is placed in the "FLOW" position and the module 800 is connected to an available flow communications port on one of the installed flow systems 450. The user now has the option to read the flow range of a selected flow system 450 or write a new flow range to a selected flow system 450. The operator selects the desired action and the unit prompts the operator for the address of the flow controller 450 to perform the desired action. Once the operator enters the desired address, the desired action is initiated. If a flow range is being read, the service module 800 displays the flow range and units for the selected flow controller 44. If a new range and units are being entered, the operator enters the desired values and the service module 800 writes the desired values to the selected flow controller 44.

If the flow controller is not installed in the SSC3 400, the operator is not required to connect the service module 800 to the SSC3 400. However, an external power source must be supplied and a mechanism must be supplied to actuate the solenoid valves on the flow frame if a calibration is being performed. With the exception of the SSC3 400 related tasks, reading the flow range and setting the flow range are performed as described above. Additionally, uninstalled flow controllers can be calibrated or have the serial address changed. If a calibration is being performed, the operator enters a desired flow value, the service module 800 sets the desired flow value, and then periodically reads and displays the actual flow value. The operator can set a new desired flow value or exit the routine at any time by pressing the appropriate key on the service module keypad 806. If an address is being set, the service module 800 requests the new address for the flow controller from the operator, with a valid range being 1 to 4. The service module 800 initiates the appropriate command sequence to the flow controller using the universal flow controller address of 250 and sets the device specific address to the value specified by the operator.

D. Summary

The service module 800 is a hand held device designed to query or program most commonly required functions to the SSC3 400 and related equipment. Some primary advantages of the service module 800 are that it has a small size, is portable, has RS232 and RS485 serial communications, and has a low cost. The interface 802 is designed to work with the service module 802 allow it to perform the desired functions with a minimal effort.

V. Future Considerations/Modifications

The SSC 40, SSC2 300, or SSC3 400 may have various changes or modifications. These changes may be implemented in part or whole, depending on the level of design effort funded or upon other factors. For instance, some modifications may be to conserve weight or space. The SSC3 400 is a portable device in that it weighs less than 35 pounds. The SSC3 400 therefore has a substantial advantage over existing sampling systems which are typically fixed and cannot be moved and are also heavy. To reduce weight even further, the existing diaphragm pump and flow controller may be replaced with a DC motor and blower assemble, variable DC supply circuit, and flow meter. The control computer can be used to regulate the voltage to the DC motor thereby eliminating the need for a flow controller. Replacement of the Blue Earth Data Collection modules 402 with PCMCIA memory cards would be a preferred upgrade since the PCMCIA cards are available in a wide array of sizes, such as from 32 Kbytes up to 16 MBytes. This enhancement would greatly improve the data storage capability of the SSC3 400. An embedded controller and turbine flow meter may be used to replace the existing mass flow controller system. This replacement should operate from the existing Sierra flow command set. The embedded controller replacement would significantly reduce cost while allowing the controller to sample water as well as gas based media.

While the foregoing specification teaches the principles of the present invention, with examples provided for the purpose of illustration, it will be understood that the practice of the invention encompasses all of the usual variations, adaptations, or modifications, as come within the scope of the following claims and their equivalents.

We claim:

1. A sampling system for use with a collection chamber module having at least one collection chamber for obtaining a sample of a fluid flow and at least one valve for controlling fluid flow into the chamber, the sampling system comprising:

a pump for passing the portion of the fluid flow through the collection chamber when the valve is in a first state;

a flow controller for controlling a rate at which the portion of the fluid flow passes into the collection chamber;

an interface for receiving a desired rate at which the portion of the fluid flow should enter the collection chamber; and a central processor for being programmed to have the desired rate from the interface and for communicating with the flow controller so that the rate at which the portion of the fluid flow passes into the collection chamber is the desired rate.

2. The sampling system as set forth in claim 1, further comprising a data module and a sensor for detecting the rate at which the portion of the fluid flow enters the collection chamber, wherein the central processor records the rate in the data module.

3. The sampling system as set forth in claim 1, further comprising a data module and a sensor for detecting a flow rate for the fluid flow, wherein the central processor records the flow rate in the data module.

4. The sampling system as set forth in claim 1, wherein the collection chamber module includes a plurality of collection chambers and the central processor is for controlling fluid flow through each of the collection chambers.

5. The sampling system as set forth in claim 4, wherein the central processor independently activates each of the collection chambers.

6. The sampling system as set forth in claim 4, wherein the interface is for receiving an order out of plurality of possible orders in which the collection chambers are to sample the fluid flow and the central processor is programmed to control valves associated with the collection chamber to achieve the desired order.

7. The sampling system as set forth in claim 1, wherein the flow controller and the pump are detachably mounted to the central processor and the flow controller is for sampling a first analyte of interest, the system further comprising a second flow controller and second pump for sampling a second analyte of interest wherein the central processor controls the flow controllers so that sampling of the first analyte and the sampling of the second analyte occur simultaneously.

8. The sampling system as set forth in claim 1, wherein the collection chamber module comprises a first collection chamber module and a second collection chamber module has at least one collection chamber and wherein the central processor is for switching to the second collection chamber module after each collection chamber in the first collection chamber module has been used.

9. The sampling system as set forth in claim 1, further comprising a weather station for detecting at least one weather condition and a data module for recording the at least one weather condition.

10. The sampling system as set forth in claim 9, wherein the valve is controlled by the central processor in response to an output of the weather station.

11. The sampling system as set forth in claim 1, further comprising a global positioning system for determining a geographic position of the collection chamber and a data module for recording the geographic position.

12. The sampling system as set forth in claim 11, wherein the valve is controlled by the central processor in response to an output of the global positioning system.

13. The sampling system as set forth in claim 1, wherein the sampling system weighs less than 40 pounds.

14. The sampling system as set forth in claim 1, further comprising a data module for collecting data while the sample of the fluid flow is being obtained and wherein the data is capable of being retrieved during sampling of the fluid flow.

15. The sampling system as set forth in claim 1, further comprising a data module for collecting data while the sample of the fluid flow is being obtained and wherein the data module is removable from the sampling system.

16. The sampling system as set forth in claim 1, further comprising a plurality of collection chambers with each collection chamber being associated with one of a plurality of valves and wherein the central processor controls the valves so that a first set of collection chambers are receiving portions of the fluid flow and a second set of collection chambers are prevented from receiving any fluid flow.

17. The sampling system as set forth in claim 16, wherein the central processor controls the plurality of valves so that at least two of the collections chambers are concurrently activated.

18. The sampling system as set forth in claim 16, wherein the interface is for indicating the first set of valves and the second set of valves to the central processor.

19. The sampling system as set forth in claim 16, wherein the flow controller comprises a plurality of flow controllers and the central processor is programmed to independently set the flow controllers to desired rates of flow.

20. The sampling system as set forth in claim 1, further comprising means for detecting a power failure and wherein the central processor recovers from the power failure in a user-defined manner.

21. The sampling system as set forth in claim 1, further comprising means for detecting a flow failure in the collection chamber and wherein the central processor recovers from the flow failure in a user-defined manner.

22. A sampling system for use with a collection chamber module having at least one collection chamber for obtaining a sample of a fluid flow, at least one pump for pumping fluid into the collection chamber and at least one valve for controlling fluid flow into the chamber, the sampling system comprising:

a first interface for receiving an operational command;

a central processor for receiving the operational command from the interface and for placing the operational command in memory, wherein the central processor is for receiving a desired flow rate from the first interface;

a flow controller for regulating fluid flow through the sampling system; and a second interface for communications between the central processor and flow controller wherein the central processor sends commands to the flow controller to control fluid flow in accordance with the operational command.

23. The sampling system of claim 22, wherein the central processor is for setting a desired flow rate for the flow controller through the second interface.

24. The sampling system of claim 23, wherein the central processor communicates with the flow controller, through the second interface, and wherein the flow controller receives feedback on an actual flow rate and adjusts the actual flow rate so that the actual flow rate is at the desired flow rate.

25. The sampling system of claim 22, wherein the central processor is for controlling the valve through the second interface.

26. The sampling system of claim 22, wherein the central processor is for controlling a solenoid through the second interface.

27. The sampling system of claim 22, wherein the central processor is for communicating with a plurality of flow controllers through the second interface.

28. The sampling system of claim 27, wherein the central processor assigns a unique identifier to each flow controller and communicates independently with each of the plurality of flow controllers.

29. The sampling system of claim 22, further comprising a plurality of valves, wherein the central processor independently controls each valve through the second interface.

30. The sampling system of claim 22, further comprising a plurality of solenoids, wherein the central processor independently controls each solenoid through the second interface.

31. A sampling system for use with a collection chamber module having at least one collection chamber for obtaining a sample of a fluid flow, at least one pump for pumping fluid into the collection chamber and at least one valve for controlling fluid flow into the chamber, the sampling system comprising:

a first interface for receiving an operational command;

a central processor for receiving the operational command from the interface and for placing the operational command in memory;

a flow controller for regulating fluid flow through the sampling system; and a second interface for communications between the central processor and flow controller; and a plurality of pumps, wherein each pump is associated with a different flow controller and the central processor independently controls each pump through the second interface;

wherein the central processor sends commands to the flow controller to control fluid flow in accordance with the operational command.

* * * * *